US009580386B2

(12) United States Patent
Nolte et al.

(10) Patent No.: US 9,580,386 B2
(45) Date of Patent: *Feb. 28, 2017

(54) SUBSTITUTED 4-AMINOCYCLOHEXANE DERIVATIVES

(71) Applicant: GRÜNENTHAL GMBH, Aachen (DE)

(72) Inventors: Bert Nolte, Aachen (DE); Wolfgang Schröder, Aachen (DE); Klaus Linz, Wachtberg (DE); Werner Englberger, Stolberg (DE); Hans Schick, Berlin (DE); Heinz Graubaum, Berlin (DE); Birgit Braun, Berlin (DE); Sigrid Ozegowski, Berlin (DE); József Bálint, Berlin (DE); Helmut Sonnenschein, Berlin (DE)

(73) Assignee: GRÜNENTHAL, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/459,540

(22) Filed: Aug. 14, 2014

(65) Prior Publication Data
US 2014/0357634 A1 Dec. 4, 2014

Related U.S. Application Data

(60) Division of application No. 13/454,256, filed on Apr. 24, 2012, now Pat. No. 8,835,689, which is a
(Continued)

(30) Foreign Application Priority Data

Mar. 27, 2008 (EP) ..................... 08005748

(51) Int. Cl.
| C07C 211/00 | (2006.01) |
| C07D 209/20 | (2006.01) |
| C07C 211/40 | (2006.01) |
| C07C 215/14 | (2006.01) |
| C07C 215/42 | (2006.01) |
| C07C 217/74 | (2006.01) |
| C07C 223/04 | (2006.01) |
| C07C 229/16 | (2006.01) |
| C07C 233/36 | (2006.01) |
| C07C 233/40 | (2006.01) |
| C07C 233/41 | (2006.01) |
| C07C 233/62 | (2006.01) |
| C07C 233/79 | (2006.01) |
| C07C 235/54 | (2006.01) |
| C07C 237/06 | (2006.01) |
| C07C 275/24 | (2006.01) |
| C07C 311/07 | (2006.01) |
| C07C 311/18 | (2006.01) |
| C07D 209/12 | (2006.01) |
| C07D 209/14 | (2006.01) |
| C07D 211/62 | (2006.01) |

(Continued)

(52) U.S. Cl.
CPC .......... *C07D 209/20* (2013.01); *A61K 31/135* (2013.01); *A61K 31/136* (2013.01); *A61K 31/165* (2013.01); *A61K 31/18* (2013.01); *A61K 31/404* (2013.01); *A61K 31/53* (2013.01); *A61K 31/5377* (2013.01); *A61K 45/06* (2013.01); *C07C 211/40* (2013.01); *C07C 211/54* (2013.01); *C07C 215/14* (2013.01); *C07C 215/42* (2013.01); *C07C 217/74* (2013.01); *C07C 223/04* (2013.01); *C07C 229/16* (2013.01); *C07C 233/36* (2013.01); *C07C 233/40* (2013.01); *C07C 233/41* (2013.01); *C07C 233/62* (2013.01); *C07C 233/79* (2013.01); *C07C 235/54* (2013.01); *C07C 237/06* (2013.01); *C07C 237/24* (2013.01); *C07C 275/24* (2013.01); *C07C 311/07* (2013.01); *C07C 311/18* (2013.01); *C07C 311/37* (2013.01); *C07D 209/12* (2013.01); *C07D 209/14* (2013.01); *C07D 211/62* (2013.01); *C07D 213/12* (2013.01); *C07D 213/82* (2013.01); *C07D 231/14* (2013.01); *C07D 251/48* (2013.01); *C07D 251/54* (2013.01); *C07D 295/135* (2013.01); *C07D 309/08* (2013.01); *C07D 333/20* (2013.01); *C07D 403/08* (2013.01); *C07D 409/08* (2013.01); *C07C 2101/08* (2013.01); *C07C 2101/14* (2013.01); *C07C 2101/16* (2013.01)

(58) Field of Classification Search
None
See application file for complete search history.

(56) References Cited

U.S. PATENT DOCUMENTS 3,328,412 A  6/1967 Atkinson et al.
4,065,573 A  12/1977 Lednicer
(Continued)

FOREIGN PATENT DOCUMENTS

AR  071066  5/2010
AR  071067  5/2010
(Continued)

OTHER PUBLICATIONS

Regitz et al, Chem. Ber., No. 101, 1968, pp. 3734-3743.
(Continued)

*Primary Examiner* — Clinton Brooks
(74) *Attorney, Agent, or Firm* — Norris McLaughlin & Marcus, P.A.

(57) ABSTRACT

The invention relates to compounds that have an affinity to the μ-opioid receptor and the ORL1-receptor, methods for their production, medications containing these compounds and the use of these compounds for the treatment of pain and other conditions.

8 Claims, No Drawings

Related U.S. Application Data continuation of application No. 12/410,801, filed on Mar. 25, 2009, now abandoned.

(51) Int. Cl.

| | | |
|---|---|---|
| *C07D 213/12* | (2006.01) | |
| *C07D 213/82* | (2006.01) | |
| *C07D 231/14* | (2006.01) | |
| *C07D 251/54* | (2006.01) | |
| *C07D 295/135* | (2006.01) | |
| *C07D 309/08* | (2006.01) | |
| *C07D 333/20* | (2006.01) | |
| *C07D 403/08* | (2006.01) | |
| *C07D 409/08* | (2006.01) | |
| *A61K 31/135* | (2006.01) | |
| *A61K 45/06* | (2006.01) | |
| *A61K 31/136* | (2006.01) | |
| *A61K 31/165* | (2006.01) | |
| *A61K 31/18* | (2006.01) | |
| *A61K 31/404* | (2006.01) | |
| *A61K 31/53* | (2006.01) | |
| *A61K 31/5377* | (2006.01) | |
| *C07C 211/54* | (2006.01) | |
| *C07C 237/24* | (2006.01) | |
| *C07C 311/37* | (2006.01) | |
| *C07D 251/48* | (2006.01) | |

(56) References Cited

U.S. PATENT DOCUMENTS

| | | | |
|---|---|---|---|
| 4,113,866 A | 9/1978 | Lednicer | |
| 4,115,589 A | 9/1978 | Lednicer | |
| 4,239,780 A | 12/1980 | Wallach | |
| 4,291,039 A | 9/1981 | Van Dyke, Jr. et al. | |
| 4,366,172 A * | 12/1982 | Lednicer | A61K 31/135 514/546 |
| 4,447,454 A | 5/1984 | Lednicer | |
| 4,575,508 A | 3/1986 | Steiner et al. | |
| 5,328,905 A | 7/1994 | Hamminga et al. | |
| 5,631,265 A | 5/1997 | Audia et al. | |
| 5,760,051 A | 6/1998 | Audia et al. | |
| 5,869,691 A | 2/1999 | Audia et al. | |
| 6,998,409 B2 | 2/2006 | Sundermann et al. | |
| 7,183,436 B2 | 2/2007 | Sundermann et al. | |
| 7,276,518 B2 | 10/2007 | Sundermann et al. | |
| 7,332,519 B2 | 2/2008 | Hinze et al. | |
| 7,485,634 B2 | 2/2009 | Martin et al. | |
| 7,507,758 B2 | 3/2009 | Sundermann et al. | |
| 7,547,707 B2 | 6/2009 | Hinze et al. | |
| 7,595,311 B2 | 9/2009 | Busch et al. | |
| 7,678,834 B2 | 3/2010 | Sundermann et al. | |
| 7,799,931 B2 | 9/2010 | Hinze et al. | |
| 7,960,404 B2 | 6/2011 | Schunk et al. | |
| 7,977,370 B2 | 7/2011 | Zemolska et al. | |
| 8,053,576 B2 | 11/2011 | Hinze et al. | |
| 8,133,992 B2 | 3/2012 | Martin | |
| 8,143,257 B2 | 3/2012 | Choi et al. | |
| 8,288,406 B2 | 10/2012 | Frormann et al. | |
| 8,835,689 B2 * | 9/2014 | Nolte | C07C 211/40 564/462 |
| 2003/0236250 A1 | 12/2003 | Castro Pineiro et al. | |
| 2004/0023947 A1 | 2/2004 | Martin et al. | |
| 2004/0147741 A1 | 7/2004 | Sundermann et al. | |
| 2004/0162287 A1 | 8/2004 | Sundermann et al. | |
| 2004/0229872 A1 | 11/2004 | Friderichs et al. | |
| 2004/0236104 A1 | 11/2004 | Sundermann et al. | |
| 2005/0054634 A1 | 3/2005 | Busch et al. | |
| 2005/0192333 A1 | 9/2005 | Hinze et al. | |
| 2005/0267107 A1 | 12/2005 | Sundermann et al. | |
| 2005/0267218 A1 | 12/2005 | Sundermann et al. | |
| 2005/0277674 A1 | 12/2005 | Hinze et al. | |
| 2006/0004034 A1 | 1/2006 | Hinze et al. | |
| 2006/0235012 A1 | 10/2006 | Davidson et al. | |
| 2007/0149557 A1 | 6/2007 | Collins et al. | |
| 2007/0213351 A1 | 9/2007 | Sundermann et al. | |
| 2008/0125475 A1 | 5/2008 | Linz et al. | |
| 2008/0221141 A1 | 9/2008 | Friderich et al. | |
| 2008/0261956 A1 | 10/2008 | Choi et al. | |
| 2008/0280942 A1 | 11/2008 | Diaz-Fernandez et al. | |
| 2009/0042866 A1 | 2/2009 | Lennox et al. | |
| 2009/0156626 A1 | 6/2009 | Hinze et al. | |
| 2009/0163716 A1 | 6/2009 | Hinze et al. | |
| 2009/0203577 A1 | 8/2009 | Baik et al. | |
| 2009/0247505 A1 | 10/2009 | Zemolka et al. | |
| 2009/0247530 A1 | 10/2009 | Nolte et al. | |
| 2009/0247561 A1 | 10/2009 | Zemolka et al. | |
| 2009/0247573 A1 | 10/2009 | Zemolka et al. | |
| 2009/0247591 A1 | 10/2009 | Zemolka et al. | |
| 2009/0326218 A1 | 12/2009 | Martin | |
| 2010/0009986 A1 | 1/2010 | Zemolka et al. | |
| 2010/0048553 A1 | 2/2010 | Schunk et al. | |
| 2010/0048554 A1 | 2/2010 | Schunk et al. | |
| 2010/0173824 A1 | 7/2010 | Busch et al. | |
| 2011/0015220 A1 | 1/2011 | Linz et al. | |
| 2011/0059999 A1 | 3/2011 | Frormann et al. | |
| 2012/0202810 A1 | 8/2012 | Nolte et al. | |
| 2013/0197095 A1 | 8/2013 | Nolte et al. | |

FOREIGN PATENT DOCUMENTS

| | | |
|---|---|---|
| AR | 071068 | 5/2010 |
| AR | 073841 | 12/2010 |
| AR | 074615 | 2/2011 |
| AU | 2002 312883 | 9/2007 |
| AU | 2009 228648 | 10/2009 |
| AU | 2009228637 | 10/2009 |
| AU | 2009228642 | 10/2009 |
| AU | 2009228643 | 10/2009 |
| AU | 2009228645 | 10/2009 |
| AU | 2009228647 | 10/2009 |
| AU | 2012 258481 A1 | 12/2012 |
| AU | 2012 258484 | 12/2012 |
| CA | 2446461 A1 | 11/2002 |
| CA | 2550868 A1 | 7/2005 |
| CA | 2658376 A1 | 1/2008 |
| CA | 2658379 A1 | 1/2008 |
| CA | 2718209 | 10/2009 |
| CA | 2719735 | 10/2009 |
| CA | 2719736 | 10/2009 |
| CA | 2719739 | 10/2009 |
| CA | 2719742 | 10/2009 |
| CA | 2719743 | 10/2009 |
| CA | 2446461 C | 4/2011 |
| CN | 1533374 | 9/2004 |
| CN | 1735619 | 2/2006 |
| CN | 1922189 | 2/2007 |
| CN | 1307158 C | 3/2007 |
| CN | 102046591 | 5/2011 |
| CN | 102046595 | 5/2011 |
| CN | 102046596 | 5/2011 |
| CN | 102046597 | 5/2011 |
| CN | 102083790 | 6/2011 |
| CO | 6251240 | 2/2011 |
| CO | 6251244 | 2/2011 |
| DE | 28 39 891 | 4/1979 |
| EC | SP 10010533 | 11/2010 |
| EC | SP 11010529 | 11/2010 |
| EP | 2257526 | 12/2010 |
| EP | 2260021 | 12/2010 |
| EP | 2260022 | 12/2010 |
| EP | 2260042 | 12/2010 |
| EP | 2271613 | 1/2011 |
| EP | 2280941 | 2/2011 |
| GB | 1 055 203 | 1/1967 |
| JP | S 5459263 A | 5/1979 |
| JP | 2003 533509 | 11/2003 |
| JP | 2004 528374 A | 9/2004 |
| JP | 2004 533439 | 11/2004 |
| JP | 2004 534858 A | 11/2004 |
| JP | 2006 508114 A | 3/2006 |
| JP | 2007 515446 A | 6/2007 |

(56) References Cited

FOREIGN PATENT DOCUMENTS

| | | |
|---|---|---|
| JP | 2011515430 | 5/2011 |
| JP | 2011515431 | 5/2011 |
| JP | 2011 517668 | 6/2011 |
| JP | 2011 517669 | 6/2011 |
| JP | 2011517670 | 6/2011 |
| JP | 2012 188457 A | 10/2012 |
| JP | 2012 254987 A | 12/2012 |
| KR | 20100132048 | 12/2010 |
| KR | 20100136521 | 12/2010 |
| MX | 2010009955 | 9/2010 |
| MX | 2010010337 | 10/2010 |
| MX | 2010010339 | 10/2010 |
| MX | 2010010407 | 10/2010 |
| MX | 2010010446 | 11/2010 |
| MX | 2010010448 | 11/2010 |
| PE | 16502009 | 11/2009 |
| PE | 16892009 | 11/2009 |
| PE | 18222009 | 12/2009 |
| PE | 18232009 | 12/2009 |
| PE | 16572009 | 11/2011 |
| TW | 200940541 | 10/2009 |
| TW | 200944501 | 11/2009 |
| WO | 00 25770 | 5/2000 |
| WO | 01 74844 A2 | 10/2001 |
| WO | 01 87838 | 11/2001 |
| WO | 02 18437 A2 | 3/2002 |
| WO | 02 90330 | 5/2002 |
| WO | 02 089783 A1 | 11/2002 |
| WO | 02 090317 | 11/2002 |
| WO | 02 090317 A1 | 11/2002 |
| WO | 03 008370 | 1/2003 |
| WO | 03 008371 | 1/2003 |
| WO | 03 008731 | 1/2003 |
| WO | 03 080557 | 1/2003 |
| WO | 2004 043899 | 5/2004 |
| WO | 2004 043900 | 5/2004 |
| WO | 2004 043902 | 5/2004 |
| WO | 2004 043909 | 5/2004 |
| WO | 2004 043949 | 5/2004 |
| WO | 2004 043967 | 5/2004 |
| WO | 2005 063769 | 7/2005 |
| WO | 2005 066183 | 7/2005 |
| WO | 2005 110970 | 11/2005 |
| WO | 2005 110971 | 11/2005 |
| WO | 2005 110973 | 11/2005 |
| WO | 2005 110974 | 11/2005 |
| WO | 2005 110975 | 11/2005 |
| WO | 2005 110976 | 11/2005 |
| WO | 2005 110977 | 11/2005 |
| WO | 2006 018184 | 2/2006 |
| WO | 2006 058088 | 6/2006 |
| WO | 2006 065479 A2 | 6/2006 |
| WO | 2006 065480 | 6/2006 |
| WO | 2006 108565 | 10/2006 |
| WO | 2007 062175 A2 | 5/2007 |
| WO | 2007 079927 | 7/2007 |
| WO | 2007 079928 | 7/2007 |
| WO | 2007 079930 | 7/2007 |
| WO | 2007 079931 | 7/2007 |
| WO | 2007 124903 | 11/2007 |
| WO | 2008 009416 | 1/2008 |
| WO | 2009 118173 | 1/2008 |
| WO | 2008009415 | 1/2008 |
| WO | 2008 040481 | 4/2008 |
| WO | 2008 040481 A1 | 4/2008 |
| WO | 2008 077597 A1 | 7/2008 |
| WO | 2008 101659 | 8/2008 |
| WO | 2008 101660 | 8/2008 |
| WO | 2009 118163 | 10/2009 |
| WO | 2009 118168 | 10/2009 |
| WO | 2009 118171 | 10/2009 |
| WO | 2009 118174 | 10/2009 |
| WO | 2009118163 | 10/2009 |
| WO | 2009118169 | 10/2009 |
| WO | 2009118171 | 10/2009 |
| WO | 2009118173 | 10/2009 |
| WO | 2009118174 | 10/2009 |

OTHER PUBLICATIONS

Sandmeyer, "Ueber Isonitrosoacetanilide und deren Kondensation zu Isatinen", Helv. Chima. Acta; 2; 1919; 234-242.
Gaspar et al., "Mild Cobalt-Catalyzed Hydrocyanation of Olefins with Tosyl Cyanide", Agnew. Chemie. Int. Ed. 2007, vol. 46, pp. 4519-4522.
Mashkovskij, M.D., Pharmaceuticals, vol. 1, Moscow, 2002, p. 11.
Rose et al, Can J. Chem., 74, 1996, 1836.
Meunier, et al, "Isolation and structure of the endogenous agonist of opioid receptor-like ORL1 receptor", Nature, vol. 377, Oct. 12, 1995, pp. 532-535.
Reinscheid, et al, "Orphanin FQ: A Neuropepetide that Activates an Opioidlike G Protein-Coupled Receptor", Science, vol. 270, Nov. 3, 1995, pp. 792-794.
Mogil, et al, "Orphanin FQ is a Functional Anti-Opioid Peptide"; Neuroscience, vol. 75, No. 2, 1996, pp. 333-337.
Jenck, et al, "Orphanin FQ acts as an anxiolytic to attenuate behavioral responses to stress"; Proc. Natl. Acad. Sci. USA, vol. 94, Dec. 1997, pp. 14854-14858.
King et al, "Spinal analgesic activity of orphanin FQ/nociceptin and its fragments", Neuroscience Letters 223 (1997), pp. 113-116.
Abdulla et al, "Axotomy Reduces the Effect of Analgesic Opioids Yet Increases the Effect of Nociceptin on Dorsal Root Ganglion Neurons"; The Journal of Neurosciene, Dec. 1, 1998, 18 (23), pp. 9685-9694.
Manabe et al, "Facilitation of long-term potentiation and memory in mice lacking nociceptin receptors"; Nature, vol. 394, Aug. 6, 1998, pp. 577-581.
Nishi et al, "Unrestrained nociceptive response and disregulation of hearing ability in mice lacking the nociceptin/orphaninFQ receptor"; The EMBO Journal, vol. 16, No. 8, 1997, pp. 1858-1864.
Calo, et al, "Pharmacology of nociceptin and its receptor: a novel therapeutic target"; British Journal of Pharmacology (2000) 129, pp. 1261-1283.
Patani et al Chem rev. 1996, vol. 96, p. 3147-3176.
Dorwald, F. A., Side reactions in Oranic Synthesis, 2005, Wiley: VCH, Weinheim p. IX of Preface.
Ardati et al. Interaction of [3H]Orphanin FQ and 125I-Tyr14-Orphanin FQ with the Orphanin FQ Receptor: Kinetics and Modulation by Cations and Guanine Nucleotides. Mol. Pharmacol., 51, 1997, p. 816-824.
Finlayson K, Pennington AJ, Kelly JS. Eur J Pharmacol. Feb. 2, 2001;412(3):203-12.
Maddox et al., J. Med. Chem., 1965, 8, 230-235.
Hashmi et al.Org. Lett. 6, 2004, 4391-4394.
Bignan, et al.; "Recent advances towards the discovery of ORL-1 receptor agonists and antagonists"; Expert Opinion, Ther. Patents (2005) 15 (4); pp. 357-388.
Rice, et al; "Spirans XVIII (I). gem-Dialkyl and Spirotetrahydrocarbazoles (2)"; Oct. 1971; vol. 8, pp. 751-754.
Katritzky et al., Synthesis 1989, 66-69.
Shiner et al. J. Am. Chem. Soc. 1981, 103, 436-442.
Xia et al. Organic Letters 2005, vol. 7, No. 7, 1315-1318.
Messina, F. et al.; Tetrahedron: Asymmetry 11 (2000) 1681-1685.
Green et al, Protective Groups in Organic Synthesis; Wiley Interscience Publication; 3rd Edition 1999.
Jirkovsky et al., J. Heterocycl. Chem., 12, 1975, pp. 937-940.
Beck et al., J. Chem. Soc. Perkin 1, 1992, pp. 813-822.
Shinada et al., Tetrahedron Letters, vol. 39, 1996, pp. 7099-7102.
Garden et al., Tetrahedron, 58, 2002, pp. 8399-8412.
Lednicer et al., J. Med. Chem., 23, 1980, pp. 424-430.
Williams et al., J. Org. Chem. 1980, 45, pp. 5082-5088.
Bandini et al. J. Org. Chem. 67, 2002, pp. 5386-5389.
Davis et al., J. Med. Chem. 35, 1992, pp. 177-184.
Yamagishi et al., J. Med. Chem. 35, 1992, pp. 2085-2094.
Gleave et al.; Bioorganic & Medicinal Chemistry Letters 8, 1998, pp. 1231-1236.

(56) References Cited

OTHER PUBLICATIONS

Sandmeyer, Helv.Chim.Acta; 2; 1919; 239.
Katz et al.; J. Med. Chem. 31, 1988; pp. 1244-1250.
van Bac et al. Tetrahedron Letters, 1988, vol. 29, pp. 2819-2822.
Kato et al. J. Fluorine Chemistry, 99, 1999, pp. 5-7.
Kim et al., J.M, Pain, 50 (1992) 355-363.
Piper, et al; Journal of Medicinal Chemistry, US American Chemical Society, Washington, No. 9, Jan. 1, 1966; pp. 911-920.
Gilbert, et al; Journal of the American Chemical Society, 1950, No. 72, pp. 2411-2417.
Chu, et al.; Tetrahedron, Elsevier Science Publishers, Amsterdam, NL, No. 62, 2006, pp. 5536-5548.
Bavetsias et al., "Design and Synthesis of Cyclopenta[g]quinazoline-Based Antifolates as Inhibitors of Thymidylate Synthase and Potential Antitumor Agents", J. Med. Chem, No. 43, pp. 1910-1926, (2000).
Catterall et al., "Binding of Batrachotoxinin A 20-α-Benzoate to a Receptor Site Associated with Sodium Channels in Synaptic Nerve Ending Particles", The Journal of Biological Chemistry, vol. 256, No. 17, pp. 8922-8927, Sep. 10, 1981.
Dirat et al., "Expeditious systhesis of novel NK1 antagonists based on a 1,2,4-trisubstituted cyclohexane", Tetrahedron Letters, No. 47, pp. 1295-1298, (2006).
Elliot et al., "NK1 antagonists based on seven membered lactam scaffolds", Bioorganic & Medicinal Chemistry Letters No. 16, pp. 2929-2932, (2006).
Hamze et al., "Systhesis of Various 3-Substituted 1,2,4-Oxadiazole-Containing Chiral B3- and α-Amino Acids from Fmoc-Protected Aspartic Acid", J. Org. Chem. No. 68, pp. 7316-7321, (2003).
Hashmi et al., "Gold Catalysis: Mild Conditions for the Synthesis of Oxazoles from N-Propargylcarboxamides and Mechanistic Aspects", Organic Letters, vol. 6.
Katritzky et al., "The Chemistry of N-Substituted Benzotriazoles; Part 11.1 The Preparation of Tertiary Amines Containing Tertiary-Alkyl Groups from Ketones, Secondary Amines and Organometallic Reagents", Communications, pp. 66-69, Jan. 1989.
Kudzma et al., "4-Phenyl- and a 4-Heteroaryl-4-anilidopiperidines. A Novel Class of Analgesic and Anesthetic Agents1", J. Med. Chem. No. 32, pp. 2534-2542, (1989).
Layer, Robert W. "The Chemistry of Imines", B.F. Goodrich Co., Research Center, pp. 489-510; Dec. 7, 1962.
Lednicer et al., "4-Amino-4-arylcyclohexanones and Their Derivatives, a Novel Class of Analgesics. 1. Modification of the Aryl Ring", The Upjohn Company, Research Laboratories, Aug. 7, 1979.
Lee et al., "Introduction of Heterocycles at the 2-position of Indoline as Ester Bioisosteres", Bull. Koren Chem. Soc. vol. 25, No. 2 pp. 207-212, (2004).
Maddox et al., "The Synthesis of Phencyclidine and Other 1-Arylcyclohexylamines", Research Laboratories, Parke, Davis and Company; vol. 8, pp. 230-232, 1985.
Morwick et al., "A Practical Approach to the Synthesis of 2,4-Disubstituted Oxazoles from Amino Acids", Organic Letters, vol. 4, No. 16, pp. 2665-2668, (2002).
Thompson et al., "Structure-Based Design of Cathepsin K Inhibitors Containing a Benzyloxy-Substituted Benzoyl Peptidomimetic", Journal of Medical Chemistry, vol. 41, No. 21, 1998, pp. 3923-3927.
Regitz et al.; Chem. Ber., No. 101, 1968, pp. 3734-3743.
Ma et al. J. Org. Chem. 2001, 66, 4525-4542.
Finalyson, et al., European Journal of Pharmacology, 412 (2001), pp. 203-212.
Prashad et al., "1,2,3-triazole as a safer and practical substitute for cyanide in the Bruylants reaction for the synthesis of tertiary amines containing tertiary alkyl or aryl groups"; Tetahedron Letters, No. 46, 1005, pp. 5455-5458, 2005.
D'Amour et al., The Biological Research Laboratory, Jan. 27, 1941, pp. 74-79.
Katritzky et al., Synthesis, Dec. 1992, pp. 1295-1298.
Corey et al.; Tetrahedron Letters, No. 36, 1972, pp. 3769-3772.
Harned et al.; Tetrahedron, No. 61, 2005, pp. 12093-12099.
Carnmalm, Antidepressant Agents—VI. 4, 4-Diphenyl-1-methylcyclohexaylamines, Acta Pharm. Suec. 12, pp. 205-208, 1975.
CAS RN 757893-37-1, American Chemical Society, pp. 1-3, 2013.
Lednicer et al., "4-(p-Bromophenyl)-4-(dimethylamino)-1-phenethylcylohexanol, an Extremely Potent Representative of a New Analgesic Series", Journal of Medicinal Chemistry, vol. 22, No. 10, pp. 1157-1158, 1979.
Mashkovkij, M.D. Pharmaceuticals, vol. 1, Moscow, 2001, p. 11-12.

\* cited by examiner

SUBSTITUTED 4-AMINOCYCLOHEXANE DERIVATIVES

This application is a division of U.S. patent application Ser. No. 13/454,256, filed Apr. 24, 2012, now allowed, which is, in turn, a continuation of U.S. patent application Ser. No. 12/410,801, filed Mar. 25, 2009, now abandoned, which, in turn, claims priority of European Patent Application No. 08005748.2, filed Mar. 27, 2008, the entire contents of which patent applications are hereby incorporated herein by reference.

The invention relates to substituted cyclohexane derivatives that have an affinity to the μ-opioid receptor and the ORL 1-receptor, methods for their production, medications containing these compounds and the use of these compounds for the production of medications.

Cyclohexane derivatives that have an affinity to the μ-opioid receptor and the ORL 1-receptor are known in the prior art. In this context, reference can be made, for example, to the following documents in their full scope WO2002/090317, WO2002/90330, WO2003/008370, WO2003/008731, WO2003/080557, WO2004/043899, WO2004/043900, WO2004/043902, WO2004/043909, WO2004/043949, WO2004/043967, WO2005/063769, WO2005/066183, WO2005/110970, WO2005/110971, WO2005/110973, WO2005/110974, WO2005/110975, WO2005/110976, WO2005/110977, WO2006/018184, WO2006/108565, WO2007/079927, WO2007/079928, WO2007/079930, WO2007/079931, WO2007/124903, WO2008/009415 and WO2008/009416.

However, the known compounds are not satisfactory in every respect and there is a need for further compounds with comparable or better properties.

Thus, in appropriate binding assays the known compounds occasionally exhibit a certain affinity to the hERG ion channel, the L-type calcium ion channel (phenylalkylamine, benzothiazepine, dihydropyridine binding sites) or to the sodium channel in the BTX assay (batrachotoxin), which can be respectively interpreted as an indication of cardiovascular side-effects. Moreover, many of the known compounds exhibit only a slight solubility in aqueous media, which can adversely affect the bioavailability, inter alia. In addition, the chemical stability of the known compounds is often merely inadequate. Thus, the compounds occasionally do not exhibit an adequate pH, UV or oxidation stability, which can adversely affect the storage stability and also the oral bioavailability, inter alia. Moreover, the known compounds have an unfavourable PK/PD (pharmacokinetic/pharmacodynamic) profile in some instances, which can be displayed, for example, in too long a duration of effect.

The metabolic stability of the known compounds also appears to be in need of improvement. An improved metabolic stability can point to an increased bioavailability. A weak or absent interaction with transporter molecules that participate in the absorption and excretion of medicinal substances should be considered an indication of an improved bioavailability and possibly low interactions of medications. Moreover, the interactions with the enzymes involved in the breakdown and excretion of medicinal substances should also be as low as possible, since such test results also indicate that low interactions of medications or none at all are possibly to be expected.

Moreover, the known compounds at times exhibit only a low selectivity with respect to the kappa-opioid receptor, which is responsible for side-effects such as e.g. dysphoria, sedation, diuresis. In addition, the known compounds at times exhibit a very high affinity to the μ-opioid receptor, which appears to be associated with other side-effects, in particular respiratory depression, constipation and addiction dependence.

WO 01/87838 discloses NK-1-receptor antagonists.

J. Med. Chem. 1996, 9, 911-920; J. Am. Chem. Soc. 1950, 72, 2411-2417; and Tetrahedron 2006, 62, 5536-5548 respectively disclose, inter alia, geminally substituted cyclohexyl-1,4-diamines, in which the amino groups are, however, substituted with hydrogen atoms throughout.

DE 28 39 891 A1 discloses, inter alia, 4-(dimethylamino)-1-methyl-4-p-tolyl cyclohexyl acetate.

The object forming the basis of the invention is to provide compounds that are suitable for pharmaceutical purposes and have advantages over the compounds of the prior art.

This object is achieved by the compounds described hereinbelow.

It has been surprisingly found that substituted cyclohexane derivatives can be produced that have an affinity to the μ-opioid receptor and the ORL 1-receptor.

The invention relates to compounds of the general formula (1),

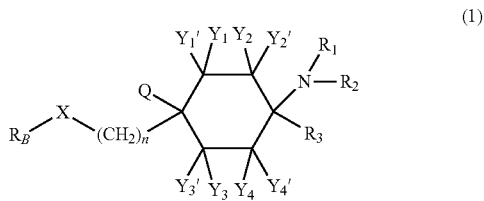

wherein $Y_1$, $Y_1'$, $Y_2$, $Y_2'$, $Y_3$, $Y_3'$, $Y_4$ and $Y_4'$ are respectively selected independently of one another from the group comprising —H, —F, —Cl, —Br, —I, —CN, —NO$_2$, —CHO, —R$_0$, —C(=O)R$_0$, —C(=O)H, —C(=O)—OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$ and —NHC(=O)N(R$_0$)$_2$; preferably respectively selected independently of one another from the group comprising —H, —F, —Cl, —CN and —C$_{1-8}$-aliphatic; or $Y_1$ and $Y_1'$, or $Y_2$ and $Y_2'$, or $Y_3$ and $Y_3'$, or $Y_4$ and $Y_4'$ jointly stand for =O;

Q stands for —R$_0$, —C(=O)—R$_0$, —C(=O)OR$_0$, —C(=O)NHR$_0$, —C(=O)N(R$_0$)$_2$ or —C(=NH)—R$_0$;

R$_0$ respectively independently stands for —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl, —C$_{1-8}$-aliphatic-heteroaryl, —C$_{3-8}$-cycloaliphatic-C$_{1-8}$-aliphatic, —C$_{3-8}$-cycloaliphatic-aryl or —C$_{3-8}$-cycloaliphatic-heteroaryl;

R$_1$ and R$_2$, independently of one another, stand for —H or —R$_0$; or R$_1$ and R$_2$ jointly form a ring and stand for —CH$_2$CH$_2$OCH$_2$CH$_2$—, —CH$_2$CH$_2$NR$_4$CH$_2$CH$_2$— or —(CH$_2$)$_{3-6}$—; on condition that R$_1$ and R$_2$ preferably do not both simultaneously stand for —H;

R$_3$ stands for —R$_0$;

R$_4$ respectively independently stands for —H, —R$_0$ or —C(=O)R$_0$;

n stands for a whole number from 0 to 12, preferably for 0;

X stands for —O—, —S— or —NR$_A$—, preferably for —NR$_A$—;

R$_A$ stands for —H, —R$_0$, —S(=O)$_{0-2}$R$_0$, —C(=O)R$_0$, —C(=O)OR$_0$, —C(=O)NH$_2$, —C(=O)NHR$_0$ or —C(=O)N(R$_0$)$_2$;

R$_B$ stands for —H, —R$_0$, —C(=O)H, —C(=O)R$_0$, —C(=O)OH, —C(=O)OR$_0$, —C(=O)NH$_2$, —C(=O)NHR$_0$, —C(=O)N(R$_0$)$_2$, —S(=O)$_{1-2}$—R$_0$, —S(=O)$_{1-2}$—OR$_0$, —S(=O)$_{1-2}$—NH$_2$, —S(=O)$_{1-2}$—NHR$_0$ or —S(=O)$_{1-2}$—N(R$_0$)$_2$; or R$_A$ and R$_B$ jointly form a ring and stand for —(CH$_2$)$_{2-5}$—, —CH$_2$CH$_2$OCH$_2$CH$_2$— or —CH$_2$CH$_2$NR$_4$CH$_2$CH$_2$—; on condition that when X stands for —O— and at the same time n stands for 0, R$_B$ does not stand for —H;

wherein

"aliphatic" respectively is a branched or unbranched, saturated or a mono- or polyunsaturated, unsubstituted or mono- or polysubstituted, aliphatic hydrocarbon residue;

"cycloaliphatic" respectively is a saturated or a mono- or polyunsaturated, unsubstituted or mono- or polysubstituted, alicyclic, mono- or multicyclic hydrocarbon residue, the number of ring-carbon atoms of which preferably lies in the specified range (i.e. "C$_{3-8}$-cycloaliphatic" preferably has 3, 4, 5, 6, 7 or 8 ring-carbon atoms);

wherein with respect to "aliphatic" and "cycloaliphatic", "mono- or polysubstituted" is understood to mean the mono- or polysubstitution, e.g. the mono-, di-, tri- or complete substitution, of one or more hydrogen atoms by substituents selected independently of one another from the group comprising aus —F, —Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)—NHR$_0$, —NH—C(=O)N(R$_0$)$_2$, —Si(R$_0$)$_3$, —PO(OR$_0$)$_2$;

"aryl", respectively independently, stands for a carbocyclic ring system with at least one aromatic ring, but without heteroatoms in this ring, wherein, if necessary, the aryl residues can be condensed with further saturated, (partially) unsaturated or aromatic ring systems, and each aryl residue can be present in unsubstituted or mono- or polysubstituted form, wherein the aryl substituents can be the same or different and in any desired and possible position of the aryl;

"heteroaryl" stands for a 5-, 6- or 7-membered cyclic aromatic residue, which contains 1, 2, 3, 4 or 5 heteroatoms, wherein the heteroatoms, the same or different, are nitrogen, oxygen or sulphur, and the heterocycle can be unsubstituted or mono- or polysubstituted; wherein in the case of the substitution on the heterocycle the substituents can be the same or different and can be in any desired and possible position of the heteroaryl; and wherein the heterocycle can also be part of a bi- or polycyclic system;

wherein with respect to "aryl" and "heteroaryl", "mono- or polysubstituted" is understood to mean the mono- or polysubstitution of one or more hydrogen atoms of the ring system by substituents selected from the group comprising —F, —Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)—N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NH—C(=O)NH$_2$, —NHC(=O)NHR$_0$, —NHC(=O)N(R$_0$)$_2$, —Si(R$_0$)$_3$, —PO(OR$_0$)$_2$; wherein any N-ring atoms present can be respectively oxidised (N-oxide);

in the form of a single stereoisomer or mixture thereof, the free compounds and/or their physiologically compatible salts and/or solvates, wherein 4-(dimethylamino)-1-methyl-4-p-tolyl cyclohexyl acetate and its salts are preferably excepted.

In the combination of different residues, e.g. Y$_1$, Y$_1$', Y$_2$, Y$_2$', Y$_3$, Y$_3$', Y$_4$ and Y$_4$', and also the combination of residues at substituents thereof such as e.g. —OR$_0$, —OC(=O)R$_0$, —OC(=O)NHR$_0$, a substituent, e.g. R$_0$, can assume different meanings within a substance for two or more residues, e.g. —OR$_0$, —OC(=O)R$_0$, —OC(=O)NHR$_0$.

The compounds according to the invention exhibit favourable binding to the ORL 1-receptor and the μ-opioid receptor.

In a preferred embodiment, the compounds according to the invention have an affinity ratio of ORL1/μ of at least 0.1. The ORL1/μ ratio is defined as $1/[K_{i(ORL1)}/K_{i(\mu)}]$. It is particularly preferred if the ORL1/μ ratio amounts to at least 0.2 or at least 0.5, more preferred at least 1.0 or at least 2.0, further preferred at least 3.0 or at least 4.0, most preferred at least 5.0 or at least 7.5 and in particular at least 10 or at least 15. In a preferred embodiment the ORL1/μ ratio lies in the range of 0.1 to 30, more preferred 0.1 to 25.

In another preferred embodiment, the compounds according to the invention have an ORL1/μ affinity ratio of more than 30, more preferred at least 50, further preferred at least 100, most preferred at least 200 and in particular at least 300.

The compounds according to the invention preferably have a K$_i$ value on the μ-opioid receptor of at maximum 500 nM, more preferred at maximum 100 nM, further preferred at maximum 50 nM, most preferred at maximum 10 nM and in particular at maximum 1.0 nM.

Methods for determining the K$_i$ value on the μ-opioid receptor are known to the person skilled in the art. The determination is preferably conducted as described in association with the examples.

It has surprisingly been shown that compounds with affinity to the ORL 1- and μ-opioid receptor, in which the ratio of ORL 1 to μ defined by $1/[K_{i(ORL1)}/K_{i(\mu)}]$ lies in the range of 0.1 to 30, preferably 0.1 to 25, have a pharmacological profile that has significant advantages compared to the other opioid receptor ligand:

1. The compounds according to the invention exhibit an efficacy in acute pain models that is at times comparable with the usual stage-3 opioids. However, they are distinguished at the same time by a significantly better compatibility compared to classic μ-opioids.
2. In contrast to common stage-3 opioids, the compounds according to the invention exhibit a significantly higher efficacy in mono- and polyneuropathic pain models, which is attributable to a synergy of ORL 1- and μ-opioid components.
3. In contrast to common stage-3 opioids, the compounds according to the invention exhibit in neuropathic animals a substantial, preferably a complete, separation of antiallodynic or antihyperalgesic effect and antinociceptive effect.
4. In contrast to common stage-3 opioids, in animal models the compounds according to the invention exhibit a significant increase in efficacy for chronic inflammatory pain (carageenan- or CFA-induced hyperalgesia, visceral inflammatory pain, amongst others) compared to acute pain.

5. In contrast to common stage-3 opioids, side-effects typical of μ-opioids (respiratory depression, opioid-induced hyperalgesia, physical dependence/withdrawal, psychic dependence/addiction, among others) are significantly reduced or preferably not observed with the compounds according to the invention in the therapeutically effective dose range.

In view of the reduced μ-opioid side-effects, on the one hand, and the increased efficacy in chronic, preferably neuropathic pain, on the other hand, the mixed ORL 1/μ agonists are thus distinguished by significantly increased safety margins compared to pure μ-opioids. This results in a significantly increased "therapeutic window" in the treatment of pain conditions, preferably chronic pain, more preferred neuropathic pain.

It is preferred if $Y_1$, $Y_1'$, $Y_2$, $Y_2'$, $Y_3$, $Y_3'$, $Y_4$ and $Y_4'$ are respectively selected independently of one another from the group comprising —H, —F, —Cl, —Br, —I, —CN, —NH$_2$, —NH—$C_{1-6}$-aliphatic, —NH—$C_{3-8}$-cycloaliphatic, —NH—$C_{1-6}$-aliphatic-OH, —N($C_{1-6}$-aliphatic)$_2$, —N($C_{3-8}$-cycloaliphatic)$_2$, —N($C_{1-6}$-aliphatic-OH)$_2$, —NO$_2$, —NH—$C_{1-6}$-aliphatic-$C_{3-8}$-cycloaliphatic, —NH—$C_{1-6}$-aliphatic-aryl, —NH—$C_{1-6}$-aliphatic-heteroaryl, —NH-aryl, —NH-heteroaryl, —SH, —S—$C_{1-6}$-aliphatic, —S—$C_{3-8}$-cycloaliphatic, —S—$C_{1-6}$-aliphatic-$C_{3-8}$-cycloaliphatic, —S—$C_{1-6}$-aliphatic-aryl, —S—$C_{1-6}$-aliphatic-heteroaryl, —S-aryl, —S-heteroaryl, —OH, —O—$C_{1-6}$-aliphatic, —O—$C_{3-8}$-cycloaliphatic, —O—$C_{1-6}$-aliphatic-OH, —O—$C_{1-6}$-aliphatic-$C_{3-8}$-cycloaliphatic, —O—$C_{1-6}$-aliphatic-aryl, —O—$C_{1-6}$-aliphatic-heretoaryl, —O-aryl, —O-heteroaryl, —O—C(=O)$C_{1-6}$-aliphatic, —O—C(=O)$C_{3-8}$-cycloaliphatic, —O—C(=O)$C_{1-6}$-aliphatic-OH, —O—C(=O)$C_{1-6}$-aliphatic-$C_{3-8}$-cycloaliphatic, —O—C(=O)$C_{1-6}$-aliphatic-aryl, —O—C(=O)$C_{1-6}$-aliphatic-heretoaryl, —O—C(=O)aryl, —O—C(=O)heteroaryl, —$C_{1-6}$-aliphatic, —$C_{3-8}$-cycloaliphatic, —$C_{1-6}$-aliphatic-$C_{3-8}$-cycloaliphatic, —$C_{1-6}$-aliphatic-aryl, —$C_{1-6}$-aliphatic-heteroaryl, -aryl, -heteroaryl, —C(=O)$C_{1-6}$-aliphatic, —C(=O)$C_{3-8}$-cycloaliphatic, —C(=O)$C_{1-6}$-aliphatic-$C_{3-8}$-cycloaliphatic, —C(=O)$C_{1-6}$-aliphatic-aryl, —C(=O)$C_{1-6}$-aliphatic-heteroaryl, —C(=O)aryl, —C(=O)heteroaryl, —CO$_2$H, —CO$_2$—$C_{1-6}$-aliphatic, —CO$_2$—$C_{3-8}$-cycloaliphatic, —CO$_2$—$C_{1-6}$-aliphatic-$C_{3-8}$-cycloaliphatic, —CO$_2$—$C_{1-6}$-aliphatic-aryl, —CO$_2$—$C_{1-6}$-aliphatic-heteroaryl, —CO$_2$-aryl, —CO$_2$-heteroaryl; or $Y_1$ and $Y_1'$, or $Y_2$ and $Y_2'$, or $Y_3$ and $Y_3'$, or $Y_4$ and $Y_4'$ jointly stand for =O. It is preferred if $Y_1$, $Y_1'$, $Y_2$, $Y_2'$, $Y_3$, $Y_3'$, $Y_4$ and $Y_4'$ are respectively selected independently of one another from the group comprising —H, —F, —Cl, —Br, —I, —CN, —NH$_2$ and —OH.

In a preferred embodiment one of the residues $Y_1$, $Y_1'$, $Y_2$, $Y_2'$, $Y_3$, $Y_3'$, $Y_4$ and $Y_4'$ differs from —H and the remaining residues stand for —H.

It is particularly preferred if $Y_1$, $Y_1'$, $Y_2$, $Y_2'$, $Y_3$, $Y_3'$, $Y_4$ and $Y_4'$ respectively stand for —H.

Q preferably stands for —R$_0$, —C(=O)R$_0$ or —C(=NH)R$_0$. It is particularly preferred if Q stands for —$C_{1-8}$-aliphatic, -aryl, -heteroaryl, —$C_{1-8}$-aliphatic-aryl, —$C_{1-8}$-aliphatic-heteroaryl, —C(=O)—$C_{1-8}$-aliphatic, —C(=O)-aryl, —C(=O)-heteroaryl, —C(=O)—$C_{1-8}$-aliphatic-aryl, —C(=O)—$C_{1-8}$-aliphatic-heteroaryl, —C(=NH)—$C_{1-8}$-aliphatic, —C(=NH)-aryl, —C(=NH)-heteroaryl, —C(=NH)—$C_{1-8}$-aliphatic-aryl, or —C(=NH)—$C_{1-8}$-aliphatic-heteroaryl.

It is particularly preferred if Q stands for —$C_{1-8}$-aliphatic, -aryl, -heteroaryl, —$C_{1-8}$-aliphatic-aryl, —C(=O)-heteroaryl or —C(=NH)-heteroaryl.

In this case, -aryl and -heteroaryl can respectively be unsubstituted or mono- or polysubstituted, preferably with substituents that are selected independently of one another from the group comprising —$C_{1-8}$-aliphatic, —OH, —OC$_{1-8}$-aliphatic, —$C_{1-8}$-aliphatic-O—$C_{1-8}$-aliphatic (e.g. —CH$_2$—O—CH$_3$), —CF$_3$, —F, —Cl, —Br, —NO$_2$, —CN, -heteroaryl, —$C_{1-8}$-aliphatic-aryl and —$C_{1-8}$-aliphatic-heteroaryl.

In a preferred embodiment Q is selected from the group comprising —$C_{1-8}$-alkyl, -phenyl, -benzyl, -pyrrolyl, -furyl, -thienyl, pyridyl, -indolyl, -benzofuryl and -benzothienyl, wherein these can respectively be unsubstituted or mono- or polysubstituted, preferably with substituents that are selected independently of one another from the group comprising —$C_{1-8}$-aliphatic, —OH, —OC$_{1-8}$-aliphatic, —$C_{1-8}$-aliphatic-O—$C_{1-8}$-aliphatic, —CF$_3$, —F, —Cl, —Br, —NO$_2$, —CN, -heteroaryl, —$C_{1-8}$-aliphatic-aryl and —$C_{1-8}$-aliphatic-heteroaryl (e.g. -ethyl-4-pyridyl). It is particularly preferred if Q is selected from the group comprising:

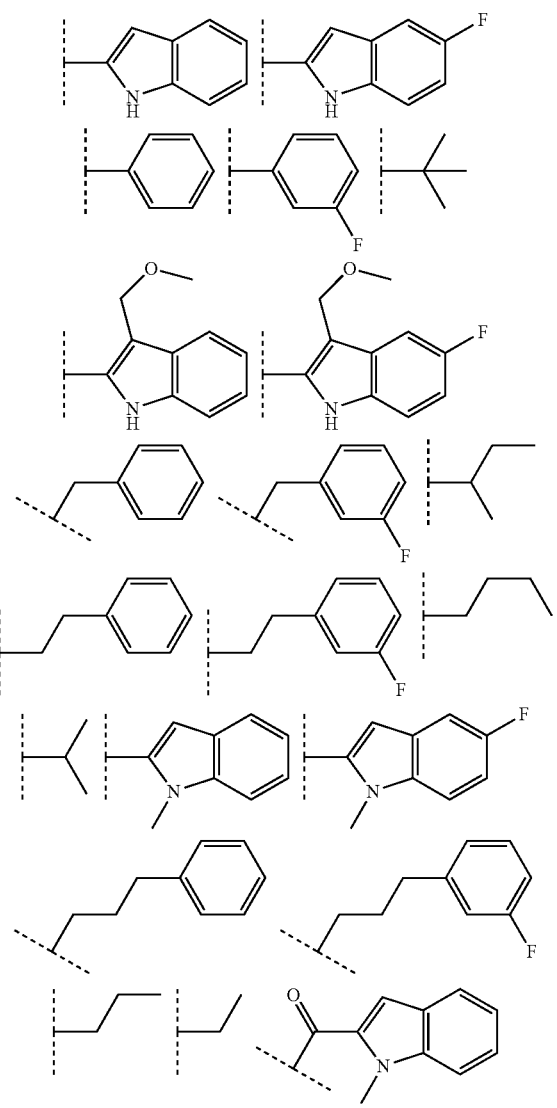

-continued

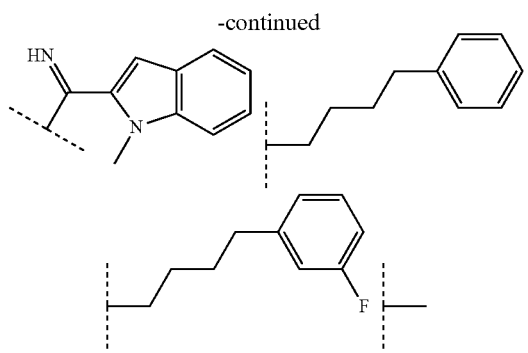

$R_0$, respectively independently, preferably stands for —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl or —$C_{1-8}$-aliphatic-heteroaryl. In this case —$C_{1-8}$-aliphatic-$C_{3-12}$-cycloaliphatic, —$C_{1-8}$-aliphatic-aryl or —$C_{1-8}$-aliphatic-heteroaryl mean that the residues —$C_{3-12}$-cycloaliphatic, -aryl or -heteroaryl are respectively bonded via a bivalent bridge —$C_{1-8}$-aliphatic-. Preferred examples of —$C_{1-8}$-aliphatic-aryl are —$CH_2$—$C_6H_5$, —$CH_2CH_2$—$C_6H_5$, and —CH=CH—$C_6H_5$.

$R_1$ and $R_2$, independently of one another, preferably stand for —H; —$C_{1-6}$-aliphatic; —$C_{3-8}$-cycloaliphatic, —$C_{1-6}$-aliphatic-aryl, —$C_{1-6}$-aliphatic-$C_{3-8}$-cycloaliphatic or —$C_{1-6}$-aliphatic-heteroaryl; or the residues $R_1$ and $R_2$ together form a ring and represent —$CH_2CH_2OCH_2CH_2$—, —$CH_2CH_2NR_4CH_2CH_2$— or —$(CH_2)_{3-6}$—, on condition that $R_1$ and $R_2$ preferably do not both stand for —H at the same time. It is more preferred if $R_1$ and $R_2$, independently of one another, stand for —H; —$C_{1-5}$-aliphatic; or the residues $R_1$ and $R_2$ together form a ring and represent —$CH_2CH_2OCH_2CH_2$—, —$CH_2CH_2NR_4$—$CH_2CH_2$— or —$(CH_2)_{3-6}$—, wherein $R_4$ preferably represents —H or —$C_{1-5}$-aliphatic, on condition that $R_1$ and $R_2$ preferably do not both stand for —H at the same time. Particularly preferred are those compounds, in which $R_1$ and $R_2$, independently of one another, stand for —$CH_3$ or —H, wherein $R_1$ and $R_2$ do not simultaneously represent —H; or $R_1$ and $R_2$ form a ring and represent —$(CH_2)_{3-4}$—. Compounds, in which $R_1$ and $R_2$ stand for —$CH_3$ or in which $R_1$ stands for —H and $R_2$ stands for —$CH_3$, are most particularly preferred.

It is particularly preferred if $R_1$ and $R_2$ together with the nitrogen atom, to which they are bonded, form one of the following functional groups:

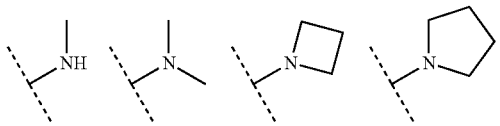

$R_3$ preferably stands for —$C_{1-8}$-aliphatic, —$C_{3-8}$-cycloaliphatic, -aryl, -heteroaryl; or for -aryl, -heteroaryl or —$C_{3-8}$-cycloaliphatic respectively bonded via a —$C_{1-3}$-aliphatic group.

It is particularly preferred if $R_3$ stands for -ethyl, -propyl, -butyl, -pentyl, -hexyl, -heptyl, -cyclopentyl, -cyclohexyl, -phenyl, -benzyl, -naphthyl, -anthracenyl, -thiophenyl, -benzothiophenyl, -furyl, -benzofuranyl, -benzodioxolanyl, -indolyl, -indanyl, -benzodioxanyl, -pyrrolyl, -pyridyl, -pyrimidyl or -pyrazinyl, respectively unsubstituted or mono- or polysubstituted; —$C_{5-6}$-cycloaliphatic, -phenyl, -naphthyl, -anthracenyl, -thiophenyl, -benzothiophenyl, -pyridyl, -furyl, -benzofuranyl, -benzodioxolanyl, -indolyl, -indanyl, -benzodioxanyl, -pyrrolyl, -pyrimidyl, -triazolyl or -pyrazinyl, respectively unsubstituted or mono- or polysubstituted, bonded via a saturated, unbranched —$C_{1-3}$-aliphatic group.

It is more preferred if $R_3$ stands for -propyl, -butyl, -pentyl, -hexyl, -phenyl, -furyl, -thiophenyl, -naphthyl, -benzyl, -benzofuranyl, -indolyl, -indanyl, -benzodioxanyl, -benzodioxolanyl, -pyridyl, -pyrimidyl, -pyrazinyl, -triazolyl or -benzothiophenyl, respectively unsubstituted or mono- or polysubstituted; -phenyl, -furyl or -thiophenyl, respectively unsubstituted or mono- or polysubstituted, bonded via a saturated, unbranched —$C_{1-3}$-aliphatic group.

It is further preferred if $R_3$ stands for -propyl, -butyl, -pentyl, -hexyl, -phenyl, -phenethyl, -thiophenyl, -pyridyl, -triazolyl, -benzothiophenyl or -benzyl, respectively substituted or unsubstituted, particularly preferred for -propyl, -3-methoxypropyl, -butyl, -pentyl, -hexyl, -phenyl, -3-methylphenyl, -3-fluorophenyl, -benzo[1,3]-dioxolyl, -thienyl, -benzothiophenyl, -4-chlorobenzyl, -benzyl, -3-chlorobenzyl, -4-methylbenzyl, -2-chlorobenzyl, -4-fluorobenzyl, -3-methylbenzyl, -2-methylbenzyl, -3-fluorobenzyl, -2-fluorobenzyl, -1-methyl-1,2,4-triazolyl or -phenethyl.

It is especially preferred if $R_3$ stands for -butyl, -ethyl, -3-methoxypropyl, -benzothiophenyl, -phenyl, -3-methylphenyl, -3-fluorophenyl, -benzo[1,3]-dioxolyl, -benzyl, -1-methyl-1,2,4-triazolyl, -thienyl or -phenethyl.

It is most preferred if $R_3$ stands for -phenyl, -benzyl or -phenethyl, respectively unsubstituted or mono- or polysubstituted on the ring; —$C_{1-5}$-aliphatic, —$C_{4-6}$-cycloaliphatic, -pyridyl, -thienyl, -thiazolyl, -imidazolyl, -1,2,4 triazolyl or -benzimidazolyl, unsubstituted or mono- or polysubstituted.

It is particularly preferred if $R_3$ stands for -phenyl, -benzyl, -phenethyl, -thienyl, -pyridyl, -thiazolyl, -imidazolyl, -1,2,4 triazolyl, -benzimidazolyl or -benzyl, unsubstituted or mono- or polysubstituted with —F, —Cl, —Br, —CN, —$CH_3$, —$C_2H_5$, —$NH_2$, —$NO_2$, —SH, —$CF_3$, —OH, —$OCH_3$, —$OC_2H_5$ or —$N(CH_3)_2$; -ethyl, -n-propyl, -2-propyl, -allyl, -n-butyl, -iso-butyl, -sec-butyl, -tert-butyl, -n-pentyl, -iso-pentyl, -neo-pentyl, -n-hexyl, -cyclopentyl or -cyclohexyl, respectively unsubstituted or mono- or polysubstituted with —OH, —$OCH_3$ or —$OC_2H_5$, wherein -thienyl, -pyridyl, -thiazolyl, -imidazolyl, -1,2,4-triazolyl and -benzimidazolyl are preferably unsubstituted.

It is particularly preferred if $R_3$ stands for -phenyl, unsubstituted or mono-substituted with —F, —Cl, —CN, —$CH_3$; -thienyl; -ethyl, -n-propyl or -n-butyl, unsubstituted or mono- or polysubstituted with —$OCH_3$, —OH or —$OC_2H_5$, in particular with —$OCH_3$.

$R_4$ preferably stands for —H, —$C_{1-5}$-aliphatic, —$C_{3-8}$-cycloaliphatic, -aryl, -heteroaryl, —$C_{1-6}$-aliphatic-aryl, —$C_{1-6}$-aliphatic-$C_{3-8}$-cycloaliphatic, —$C_{1-6}$-aliphatic-heteroaryl, —C(=O)aryl, —C(=O)heteroaryl, or —C(=O)$C_{1-6}$-aliphatic, more preferred for —H or —$C_{1-5}$-aliphatic.

It is preferred if n stands for a whole number from 0 to 6, more preferred for 0, 1, 2 or 3, further preferred for 0 or 1, particularly preferred if n=0.

$R_B$ preferably stands for —H, —$C_{1-6}$-aliphatic, —$C_{3-8}$-cycloaliphatic, —$C_{1-6}$-aliphatic-$C_{3-8}$-cycloaliphatic, —$C_{1-6}$-aliphatic-aryl, —$C_{1-6}$-aliphatic-heteroaryl, -aryl, -heteroaryl, —C(=O)H, —C(=O)$C_{1-6}$-aliphatic, —C(=O)$C_{3-8}$-cycloaliphatic, —C(=O)$C_{1-6}$-aliphatic-$C_{3-8}$-cycloaliphatic, —C(=O)$C_{1-6}$-aliphatic-aryl, —C(=O)$C_{1-6}$-aliphatic-heteroaryl, —C(=O)—$C_{3-8}$-cycloaliphatic-aryl, —C(=O)—$C_{3-8}$-cycloaliphatic-heteroaryl, —C(=O)aryl, —C(=O)heteroaryl, —C(=O)OH, —$CO_2$—$C_{1-6}$-aliphatic, —CO$_2$—C$_{3-8}$-cycloaliphatic, —CO$_2$—C$_{1-6}$-aliphatic-C$_{3-8}$-cycloaliphatic, —CO$_2$—C$_{1-6}$-aliphatic-aryl, —CO$_2$—C$_{1-6}$-aliphatic-heteroaryl, —CO$_2$-aryl, —CO$_2$-heteroaryl, —C(=O)NH$_2$, —C(=O)NHC$_{1-6}$-aliphatic, —C(=O)NHC$_{3-8}$-cycloaliphatic, —C(=O)NHC$_{1-6}$-aliphatic-C$_{3-8}$-cycloaliphatic, —C(=O)NHC$_{1-6}$-aliphatic-aryl, —C(=O)NHC$_{1-6}$-aliphatic-heteroaryl, —C(=O)NH aryl, —C(=O)NH heteroaryl, —C(=O)N(C$_{1-6}$-aliphatic)$_2$, —C(=O)N(C$_{3-8}$-cycloaliphatic)$_2$, —C(=O)N(C$_{1-6}$-aliphatic-C$_{3-8}$-cycloaliphatic)$_2$, —C(=O)N(C$_{1-6}$-aliphatic-aryl)$_2$, —C(=O)N(C$_{1-6}$-aliphatic-heteroaryl)$_2$, —C(=O)N (aryl)$_2$, —C(=O)N(heteroaryl)$_2$, —S(=O)$_{1-2}$—C$_{1-6}$-aliphatic, —S(=O)$_{1-2}$—C$_{3-8}$-cycloaliphatic, —S(=O)$_{1-2}$—C$_{1-6}$-aliphatic-C$_{3-8}$-cycloaliphatic, —S(=O)$_{1-2}$—C$_{1-6}$-aliphatic-aryl, —S(=O)$_{1-2}$—C$_{1-6}$-aliphatic-heteroaryl, —S(=O)$_{1-2}$—C$_{3-8}$-cycloaliphatic-aryl, —S(=O)$_{1-2}$—C$_{3-8}$-cycloaliphatic-heteroaryl —S(=O)$_{1-2}$-aryl, —S(=O)$_{1-2}$-heteroaryl, —S(=O)$_{1-2}$—OC$_{1-6}$-aliphatic, —S(=O)$_{1-2}$—OC$_{3-8}$-cycloaliphatic, —S(=O)$_{1-2}$—OC$_{1-6}$-aliphatic-C$_{3-8}$-cycloaliphatic, —S(=O)$_{1-2}$—OC$_{1-6}$-aliphatic-aryl, —S(=O)$_{1-2}$—OC$_{1-6}$-aliphatic-heteroaryl, —S(=O)$_{1-2}$—O aryl, —S(=O)$_{1-2}$—O heteroaryl, —S(=O)$_{1-2}$—NH$_2$, —S(=O)$_{1-2}$—NHC$_{1-6}$-aliphatic, —S(=O)$_{1-2}$—NHC$_{3-8}$-cycloaliphatic, —S(=O)$_{1-2}$—NHC$_{1-6}$-aliphatic-C$_{3-8}$-cycloaliphatic, —S(=O)$_{1-2}$—NHC$_{1-6}$-aliphatic-aryl, —S(=O)$_{1-2}$—NHC$_{1-6}$-aliphatic-heteroaryl, —S(=O)$_{1-2}$—NH-aryl, —S(=O)$_{1-2}$—NH-heteroaryl, —S(=O)$_{1-2}$—N(C$_{1-6}$-aliphatic)$_2$, —S(=O)$_{1-2}$—N(C$_{3-8}$-cycloaliphatic)$_2$, —S(=O)$_{1-2}$—N(C$_{1-6}$-aliphatic-C$_{3-8}$-cycloaliphatic)$_2$, —S(=O)$_{1-2}$—N(C$_{1-6}$-aliphatic-aryl)$_2$, —S(=O)$_{1-2}$—N(C$_{1-6}$-aliphatic-heteroaryl)$_2$, —S(=O)$_{1-2}$—N(aryl)$_2$ or —S(=O)$_{1-2}$—N(heteroaryl)$_2$.

It is particularly preferred if R$_B$ stands for —H, —C$_{1-8}$-aliphatic, —C$_{1-8}$-aliphatic-aryl, —C$_{1-8}$-aliphatic-heteroaryl, —C(=O)—C$_{1-8}$-aliphatic, —C(=O)—C$_{1-8}$-aliphatic-aryl, —C(=O)—C$_{1-8}$-aliphatic-heteroaryl, —C(=O)—C$_{3-8}$-cycloaliphatic-aryl, —C(=O)—C$_{3-8}$-cycloaliphatic-heteroaryl, —C(=O)NH—C$_{1-8}$-aliphatic, —S(=O)$_{1-2}$—C$_{1-8}$-aliphatic, —S(=O)$_{1-2}$-aryl, —S(=O)$_{1-2}$-heteroaryl, —S(=O)$_{1-2}$—C$_{1-8}$-aliphatic-aryl, —S(=O)$_{1-2}$—C$_{1-8}$-aliphatic-heteroaryl, —S(=O)$_{1-2}$—C$_{3-8}$-cycloaliphatic-aryl or —S(=O)$_{1-2}$—C$_{3-8}$-cycloaliphatic-heteroaryl.

X preferably stands for —O— or —NR$_A$—, particularly preferred for —NR$_A$—.

If X stands for —O—, then R$_B$ preferably does not stand for —H. If R$_B$ stands for —H, then n is preferably 1, 2, 3 or 4. If X stands for —O—, then n preferably stands for 0 or 1 and R$_B$ preferably stands for —C$_{1-8}$-aliphatic or —C$_{1-8}$-aliphatic-aryl.

If X stands for —NR$_A$—, then R$_A$ stands for —H, —R$_0$, —S(=O)$_{0-2}$R$_0$, —C(=O)R$_0$, —C(=O)OR$_0$, —C(=O)NH$_2$, —C(=O)NHR$_0$ or —C(=O)N(R$_0$)$_2$; preferably for —H or —R$_0$ (in particular —C$_{1-8}$-aliphatic); particularly preferred for —H or —CH$_3$; or R$_A$ jointly with R$_B$ forms a ring and stands for —(CH$_2$)$_{3-4}$—.

The group "R$_B$—X—(CH$_2$)$_n$—" preferably stands for

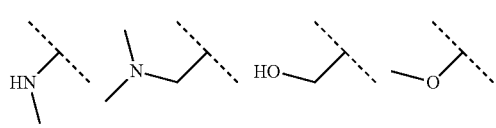

Preferred representatives of the group —(CH$_2$)$_n$—NH—C(=O)—C$_{1-8}$-aliphatic-aryl are illustrated below:

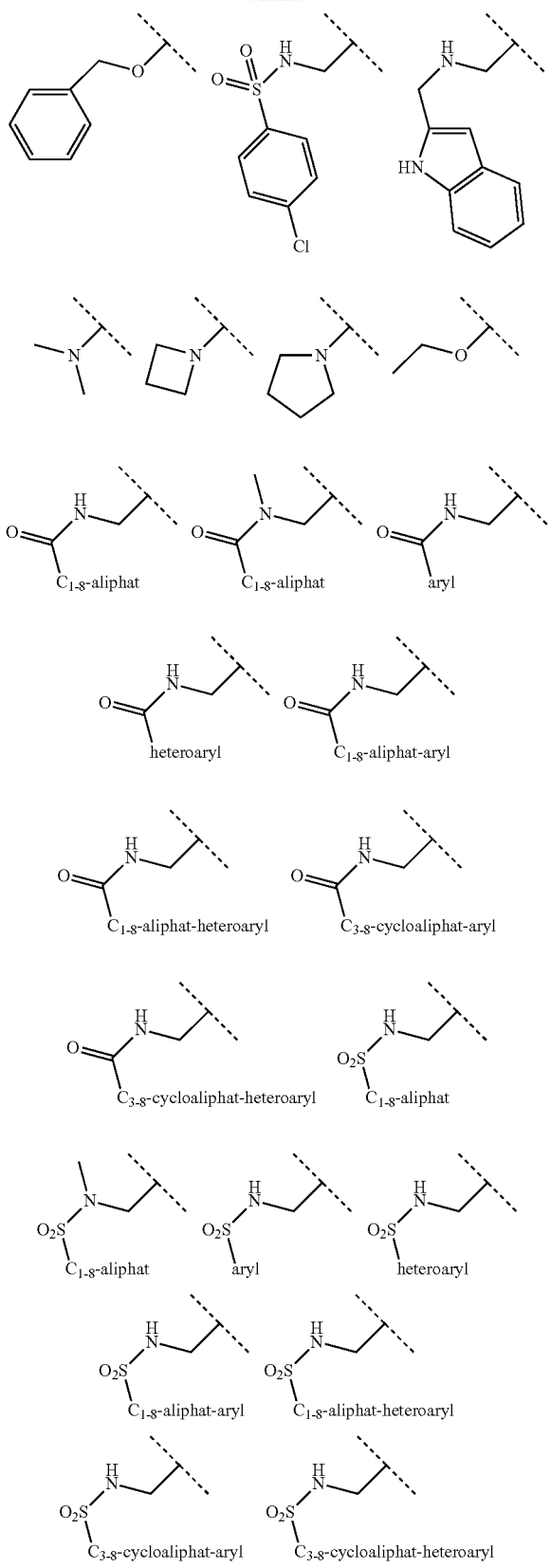

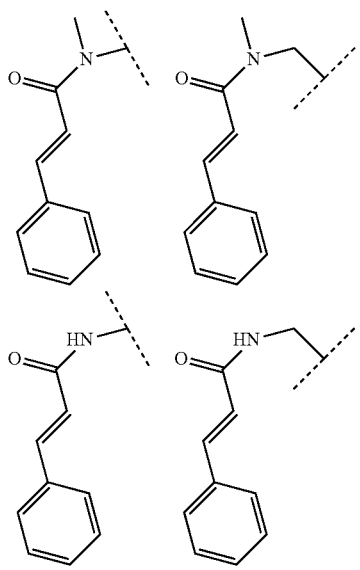

In a preferred embodiment of the compounds according to the invention $R_A=R_B$. In another preferred embodiment of the compounds according to the invention $R_A \neq R_B$.

In a particularly preferred embodiment of the compounds according to the invention n=0 and X stands for —$NR_A$—. This then concerns geminally di-substituted 1,4-diamines of the general formula (1.1)

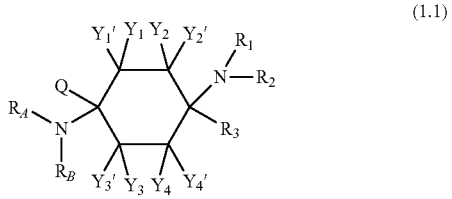
(1.1)

wherein at least one of the two amino groups, preferably both amino groups, cannot be simultaneously substituted with two hydrogen atoms.

For the purposes of the description hydrocarbon residues are divided into aliphatic hydrocarbon residues and aromatic hydrocarbon residues.

Aliphatic hydrocarbon residues are themselves divided into non-cyclic aliphatic hydrocarbon residues (="aliphatic") and cyclic aliphatic hydrocarbon residues, i.e. alicyclic hydrocarbon residues (="cycloaliphatic"). Cycloaliphatic compounds can be monocyclic or multicyclic. Alicyclic hydrocarbon residues ("cycloaliphatic") comprise both pure aliphatic carbocycles and aliphatic heterocycles, i.e.—unless expressly specified—"cycloaliphatic" comprises pure aliphatic carbocycles (e.g. cyclohexyl), pure aliphatic heterocycles (e.g. piperidyl or piperazyl) and also non-aromatic, multicyclic, possibly mixed, systems (e.g. decalinyl, decahydroquinolinyl).

Aromatic hydrocarbons are themselves divided into carbocyclic aromatic hydrocarbons (="aryl") and heterocyclic aromatic hydrocarbons (="heteroaryl").

The classification of multicyclic, at least partially aromatic systems preferably depends on whether at least one aromatic ring of the multicyclic system has at least one heteroatom (usually N, O or S) in the ring. If at least one such heteroatom is present in this ring, this is preferably a "heteroaryl" (even if a further carbocyclic aromatic or non-aromatic ring with or without heteroatom is possibly present as additionally present cycle of the multicyclic system); if such a heteroatom is not present in any of the possibly several aromatic rings of the multicyclic system, then this is preferably "aryl" (even if a ring heteroatom is present in a possibly additionally present non-aromatic cycle of the multicyclic system).

Therefore, the following priority in the classification applies within the cyclic substituents: heteroaryl>aryl>cycloaliphatic.

For the purposes of the description monovalent and multivalent, i.e. bivalent, hydrocarbon residues are not distinguished between conceptually, i.e. depending on the context, "$C_{1-3}$-aliphatic" covers e.g. —$C_{1-3}$-alkyl, —$C_{1-3}$-alkenyl and —$C_{1-3}$-alkinyl, as well as e.g. —$C_{1-3}$-alkylene-, —$C_{1-3}$-alkenylene- and $C_{1-3}$-alkinylene.

Aliphatic is preferably respectively a branched or unbranched, saturated or a mono- or polyunsaturated, unsubstituted or mono- or polysubstituted, aliphatic hydrocarbon residue. Where aliphatic is mono- or polysubstituted, the substituents are selected independently of one another from the group comprising —F, —Cl, —Br, —I, —CN, —$NO_2$, —CHO, =O, —$R_0$, —C(=O)$R_0$, —C(=O)OH, —C(=O)O$R_0$, —C(=O)$NH_2$, —C(=O)NH$R_0$, —C(=O)N($R_0$)$_2$, —OH, —O$R_0$, —OC(=O)H, —OC(=O)$R_0$, —OC(=O)O$R_0$, —OC(=O)NH$R_0$, —OC(=O)N($R_0$)$_2$, —SH, —S$R_0$, —$SO_3$H, —S(=O)$_{1-2}$—$R_0$, —S(=O)$_{1-2}$$NH_2$, —$NH_2$, —NH$R_0$, —N($R_0$)$_2$, —$N^+$($R_0$)$_3$, —$N^+$($R_0$)$_2$$O^-$, —NHC(=O)$R_0$, —NHC(=O)O$R_0$, —NHC(=O)$NH_2$, —NHC(=O)NH$R_0$, —NHC(=O)N($R_0$)$_2$, —Si($R_0$)$_3$, —PO(O$R_0$)$_2$. Thus, "aliphatic" covers acyclic saturated or unsaturated hydrocarbon residues that can be branched or straight-chain, i.e. alkanyls, alkenyls and alkinyls. In this case, alkenyls have at least one C=C double bond and alkinyls have at least one C≡C triple bond. Preferred unsubstituted monovalent aliphatics comprise —$CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, —$CH_2CH(CH_3)_2$, —C($CH_3$)$_3$, —$CH_2CH_2CH_2$—$CH_2CH_3$ and —$CH_2CH_2CH_2CH_2CH_2CH_3$; but also —CH=$CH_2$, —C≡CH, —$CH_2$CH=$CH_2$, —CH=CH$CH_3$, —$CH_2$C≡CH, —C≡C$CH_3$ and —CH=CH$CH_2$. Preferred unsubstituted bivalent aliphatics comprise —$CH_2$—, —$CH_2CH_2$—, —$CH_2$CH($CH_3$)—, —CH($CH_3$)—$CH_2$—, —$CH_2CH_2CH_2$—, —CH($CH_3$)$CH_2CH_2$—, —$CH_2$CH($CH_3$)—$CH_2$—, —$CH_2CH_2$CH($CH_3$)—, —CH—($CH_2CH_3$)$CH_2$— and —$CH_2CH_2$—$CH_2CH_2$—; but also —CH=CH—, —C≡C—, —$CH_2$CH=CH—, —CH=CH$CH_2$—, —$CH_2$C≡C— and —C≡C$CH_2$—. Preferred substituted monovalent aliphatics comprise —$CH_2$F, —$CHF_2$, —$CF_3$, —$CH_2CF_3$, —$CF_2CF_3$, —$CH_2$OH, —$CH_2CH_2$OH, —$CH_2$CHOH$CH_3$, —$CH_2$O$CH_3$ and —$CH_2CH_2$O$CH_3$. Preferred substituted bivalent aliphatics comprise —$CF_2$—, —$CF_2CF_2$—, —$CH_2$CHOH—, —CHOH$CH_2$— and —$CH_2$CHOH$CH_2$—. -Methyl-, -ethyl-, -n-propyl- and -n-butyl- are particularly preferred.

Cycloaliphatic is preferably respectively a saturated or a mono- or polyunsaturated, unsubstituted or mono- or polysubstituted, aliphatic (i.e. not aromatic), mono- or multicyclic hydrocarbon residue. The number of ring-carbon atoms preferably lies in the specified range (i.e. a "$C_{3-8}$-cycloaliphatic" preferably has 3, 4, 5, 6, 7 or 8 ring-carbon atoms). For the purposes of the description "$C_{3-8}$-cycloaliphatic" is preferably a cyclic hydrocarbon with 3, 4, 5, 6, 7 or 8 ring-carbon atoms, saturated or unsaturated, but not aromatic, wherein possibly one or two carbon atoms are replaced independently of one another by a heteroatom S, N or O. Where cycloalkyl is mono- or polysubstituted, the substituents are selected independently of one another from the group comprising —F, —Cl, —Br, —I, —CN, —NO$_2$, —CHO, =O, —R$_0$, —C(=O)R$_0$, —C(=O)OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)—N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$, —NHC(=O)N(R$_0$)$_2$, —Si(R$_0$)$_3$, —PO(OR$_0$)$_2$. Advantageously, $C_{3-8}$-cycloaliphatic is selected from the group comprising cyclopropyl, cyclobutyl, cyclopentyl, cyclohexyl, cycloheptyl, cyclooctyl, cyclopentenyl, cyclohexenyl, cycloheptenyl and cyclooctenyl, but also tetrahydropyranyl, dioxanyl, dioxolanyl, morpholinyl, piperidinyl, piperazinyl, pyrazolinonyl and pyrrolidinyl.

In association with "aliphatic" or "cycloaliphatic", "mono- or polysubstituted" is preferably understood to mean the mono- or polysubstitution, e.g. the mono-, di-, tri- or 4-substitution, of one or more hydrogen atoms by —F, —Cl, —Br, —I, —OH, —OC$_{1-6}$-alkyl, —OC(=O)C$_{1-6}$-alkyl, —SH, —NH$_2$, —NHC$_{1-6}$-alkyl, —N(C$_{1-6}$-alkyl)$_2$, —C(=O)OC$_{1-6}$-alkyl or —C(=O)OH. Compounds, wherein "aliphatic substituted" or "cycloaliphatic substituted" means aliphatic or cycloaliphatic substituted with —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$, are preferred. Particularly preferred substituents are —F, —Cl, —OH, —SH, —NH$_2$ and —C(=O)OH.

Polysubstituted residues are understood to be those residues that are polysubstituted, e.g. twice or three times either at different or at the same atoms, e.g. three times at the same C-atom, as in the case of —CF$_3$ or —CH$_2$CF$_3$, or at different sites, as in the case of —CH(OH)—CH=CH—CHCl$_2$. The polysubstitution can occur with the same or with different substituents. A substituent may also be substituted itself. Thus, -Oaliphatic also covers —OCH$_2$CH$_2$O—CH$_2$CH$_2$OH, amongst others. It is preferred if aliphatic or cycloaliphatic is substituted with —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$. It is most particularly preferred if aliphatic or cycloaliphatic is substituted with —OH, —OCH$_3$ or —OC$_2$H$_5$.

It is preferred if aryl respectively independently stands for a carbocyclic ring system with at least one aromatic ring, but without heteroatoms in this ring, wherein the aryl residues can possibly be condensed with further saturated, (partially) unsaturated or aromatic ring systems and each aryl residue can be present in unsubstituted or mono- or polysubstituted form, wherein the aryl substituents are the same or different and can be in any desired and possible position of the aryl. Preferred aryls are phenyl, naphthyl, anthracenyl, phenanthrenyl, fluoroanthenyl, fluoroenyl, indanyl and tetralinyl. Phenyl and naphthyl are particularly preferred. Where aryl is mono- or polysubstituted, the aryl substituents can be the same or different and be in any desired and possible position of the aryl, and are selected independently of one another from the group comprising —F, —Cl, —Br, —I, —CN, —NO$_2$, —CHO, =O, —R$_0$, —C(=O)R$_0$, —C(=O)OH, —C(=O)OR$_0$, —C(=O)NH$_2$, —C(=O)NHR$_0$, —C(=O)N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$, —NHC(=O)N(R$_0$)$_2$, —Si(R$_0$)$_3$, —PO(OR$_0$)$_2$. Preferred substituted aryls are 2-fluorophenyl, 3-fluorophenyl, 4-fluorophenyl, 2,3-difluorophenyl, 2,4-difluorophenyl, 3,4-difluorophenyl, 2-chlorophenyl, 3-chlorophenyl, 4-chlorophenyl, 2,3-dichlorophenyl, 2,4-dichlorophenyl, 3,4-dichlorophenyl, 2-methoxy-phenyl, 3-methoxy-phenyl, 4-methoxy-phenyl, 2,3-dimethoxy-phenyl, 2,4-dimethoxy-phenyl, 3,4-dimethoxy-phenyl, 2-methyl-phenyl, 3-methyl-phenyl, 4-methyl-phenyl, 2,3-dimethyl-phenyl, 2,4-dimethyl-phenyl and 3,4-dimethyl-phenyl.

Heteroaryl preferably stands for a 5-, 6- or 7-membered cyclic aromatic residue that contains 1, 2, 3, 4 or 5 heteroatoms, wherein the heteroatoms, the same or different, are nitrogen, oxygen or sulphur, and the heterocycle can be unsubstituted or mono- or polysubstituted; wherein in the case of the substitution on the heterocycle, the substituents can be the same or different and can be in any desired and possible position of the heteroaryl; and wherein the heterocycle can also be part of a bi- or polycyclic system. "Heteroaryl" is preferably selected from the group comprising pyrrolyl, indolyl, furyl (furanyl), benzofuranyl, thienyl (thiophenyl), benzothienyl, benzothiadiazolyl, benzooxadiazolyl, benzothiazolyl, benzooxazolyl, benzotriazolyl, benzodioxolanyl, benzodioxanyl, phthalazinyl, pyrazolyl, imidazolyl, thiazolyl, oxazolyl, isoxazoyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein the bonding can occur via any desirable and possible ring member of the heteroaryl residue. Where heteroaryl is mono- or polysubstituted, the heteroaryl substituents can be the same or different and can be in any desirable and possible position of the heteroaryl, and are selected independently of one another from the group comprising —F, —Cl, —Br, —I, —CN, —NO$_2$, —CHO, =O, —R$_0$, —C(=O)R$_0$, —C(=O)OH, —C(=O)OR$_0$, —C(=O)—NH$_2$, —C(=O)NHR$_0$, —C(=O)N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NH—C(=O)R$_0$, —NHC(=O)OR$_0$, —NHC(=O)NH$_2$, —NHC(=O)NHR$_0$, —NHC(=O)N(R$_0$)$_2$, —Si(R$_0$)$_3$, —PO(OR$_0$)$_2$.

With respect to "aryl" or "heteroaryl", "mono- or polysubstituted" are understood to mean the mono- or polysubstitution, e.g. di-, tri-, 4- or 5-substitution, of one or more hydrogen atoms of the ring system.

Particularly preferred are the substituents or aryl and heteroaryl respectively selected independently of one another from —F, —Cl, —Br, —I, —CN, —CHO, —CO$_2$H, —NH$_2$, —NO$_2$, —NHR$_0$, —N(R$_0$)$_2$, —N$^+$(R$_0$)$_3$, —N$^+$(R$_0$)$_2$O$^-$, —SH, —SR$_0$, —OH, —OR$_0$, —C(=O)R$_0$, —CO$_2$R$_0$, —C(=O)NH$_2$, —C(=O)NHR$_0$, —C(=O)N(R$_0$)$_2$, —S(=O)$_{1-2}$R$_0$, —S(=O)$_2$NH$_2$, —SO$_3$H, =O or —R$_0$. Preferred substituents are —F, —Cl, —Br, —I, —OH, —OC$_{1-6}$-alkyl, —O—C(=O)—C$_{1-6}$-alkyl, —SH, —NH$_2$, —NHC$_{1-6}$-alkyl, —N(C$_{1-6}$-alkyl)$_2$, —C(=O)OC$_{1-6}$-alkyl or —C(=O)OH. Compounds, in which "aryl substituted" or "heteroaryl substituted" means aryl or heteroaryl substituted with —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$, are preferred. Particularly preferred substituents are —F, —Cl, —OH, —SH, —NH$_2$ and —C(=O)OH.

The compounds according to the invention can be present in the form of a single stereoisomer or mixture thereof, the free compounds and/or their physiologically compatible salts and/or solvates.

The compounds according to the invention can be chiral or achiral, depending on the substitution pattern.

Depending on the substitution with respect to the cyclohexane ring the compounds according to the invention can be isomers, in which the substitution pattern in 1,4 position (1 position: >C(NR$_1$R)R$_3$; 4 position: >CQ((CH$_2$)$_n$XR$_B$) can also be referred to as syn/anti. "Syn/anti isomers" are a subgroup of the stereoisomers (configuration isomers).

In a preferred embodiment, the diastereomer excess of the syn-isomer amounts to at least 50% de, more preferred at least 75% de, more preferred at least 90% de, most preferred at least 95% de, and in particular at least 99% de. In another preferred embodiment, the diastereomer excess of the anti-isomer amounts to at least 50% de, more preferred at least 75% de, more preferred at least 90% de, most preferred at least 95% de, and in particular at least 99% de.

Suitable methods for separating the isomers (diastereomers) are known to the person skilled in the art. Column chromatography, preparative HPLC and crystallisation processes can be given as examples.

If the compounds according to the invention are chiral, then they are preferably present as racemate or in concentrated form of an enantiomer. In a preferred embodiment the enantiomer excess(ee) of the S-enantiomer amounts at least 50% ee, more preferred at least 75% ee, more preferred at least 90% ee, most preferred at least 95% ee, and in particular at least 99% ee. In another preferred embodiment, the enantiomer excess (ee) of the R-enantiomer amounts to at least 50% ee, more preferred at least 75% ee, more preferred at least 90% ee, most preferred at least 95% ee, and in particular at least 99% ee.

Suitable methods for separating the enantiomers are known to the person skilled in the art. Preparative HPLC on chiral stationary phases and conversion into diastereomeric intermediates can be given as examples. The conversion into diastereomeric intermediates can occur, for example, as salt formation by means of chiral, enantiomer-pure acids. After separation of the diastereomers thus formed, the salt can then be converted into the free base or another salt again.

Unless expressly specified, each reference to the compounds according to the invention covers all isomers (e.g. stereoisomers, diastereomers, enantiomers) in any desired mixture ratio.

Unless expressly specified, each reference to the compounds according to the invention covers the free compounds (i.e. the forms that are not present in the form of salt) and all physiologically compatible salts.

For the purposes of the description, physiologically compatible salts of the compounds according to the invention are present as salts with anions or acids of the respective compound with inorganic or organic acids, which are physiologically compatible—in particular on application in humans and/or mammals.

Examples of physiologically compatible salts of specific acids are salts of: hydrochloric acid, hydrobromic acid, sulphuric acid, methane sulphonic acid, formic acid, acetic acid, oxalic acid, succinic acid, malic acid, tartaric acid, mandelic acid, fumaric acid, lactic acid, citric acid, glutamic acid, saccharinic acid, monomethyl sebacic acid, 5-oxoproline, hexane-1-sulphonic acid, nicotinic acid, 2-, 3- or 4-aminobenzoic acid, 2,4,6-trimethyl benzoic acid, α-liponic acid, acetylglycine, acetylsalicylic acid, hippuric acid and/or aspartic acid. The hydrochloride, citrate and hemicitrate are particularly preferred.

Physiologically compatible salts with cations or bases are salts of the respective compound—as anion with at least one, preferably inorganic, cation, which are physiologically compatible—in particular on application in humans and/or mammals. Particularly preferred are the salts of the alkali and earth alkali metals, also ammonium salts, but in particular (mono-) or (di-) sodium, (mono-) or (di-) potassium, magnesium or calcium salts.

Respectively preferred embodiments of the compounds according to the invention are explained below. Unless expressly specified, all definitions of the respective substituents explained previously (i.e. from R$_0$ to R$_4$, Y$_1$ to Y$_4$', Q etc., for example) and their respective embodiments apply accordingly and will not therefore be repeated.

Preferred embodiments of the compounds according to the invention of the general formula (1) have the general formula (2):

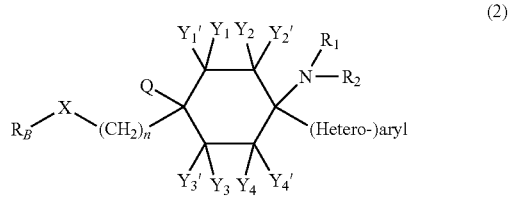

(2)

wherein
(hetero)aryl stands for heteroaryl or aryl; preferably phenyl; respectively unsubstituted or mono- or polysubstituted, wherein the substituents are preferably selected independently of one another from the group comprising —F, —Cl, —Br, —I, —CN, —NO$_2$, —CHO, —R$_0$, —C(=O)R$_0$, —C(=O)H, —C(=O)OH, —C(=O)OR$_0$, —C(=O)NH$_2$, —C(=O)NH—R$_0$, —C(=O)—N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)—OR$_0$, —NH—C(=O)NH$_2$, —NHC(=O)NHR$_0$ and —NHC(=O)N(R$_0$)$_2$; more preferred —F, —Cl, —Br, —I, —CF$_3$, —CN and —NO$_2$.

Particularly preferred embodiments of the compounds according to the invention of the general formula (2) have the general formula (2.1), (2.2), (2.3), (2.4), (2.5), (2.6), (2.7), (2.8), (2.9), (2.10), (2.11), (2.12), (2.13) or (2.14):

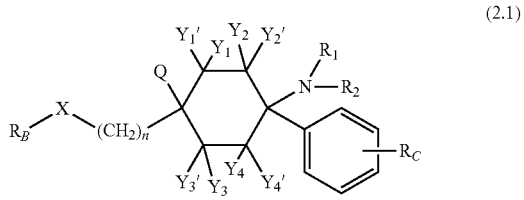

(2.1)

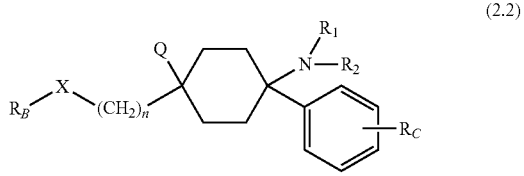

(2.2)

-continued (2.3) 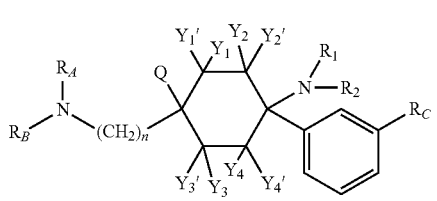

(2.4) 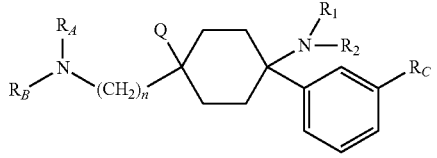

(2.5) 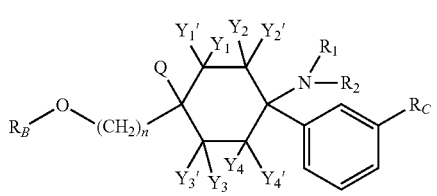

(2.6) 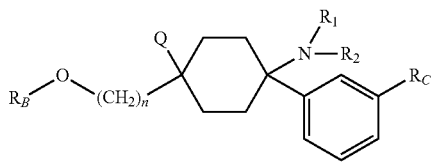

(2.7) 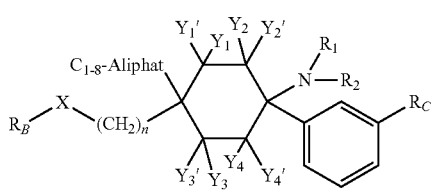

(2.8) 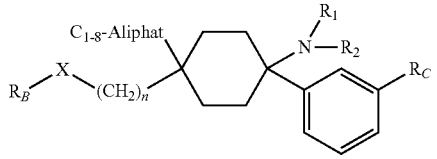

(2.9) 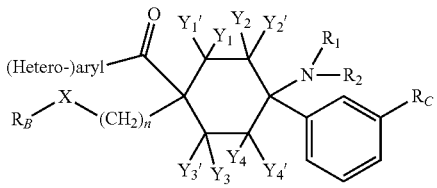

(2.10) 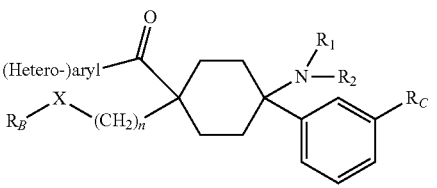

-continued (2.11) 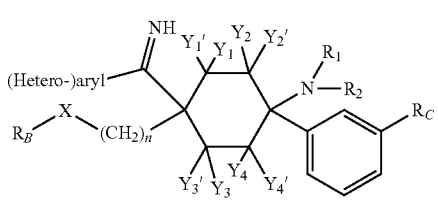

(2.12) 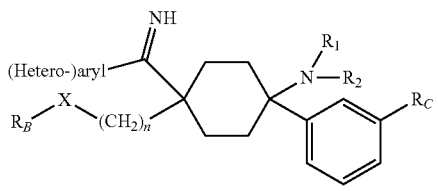

(2.13) 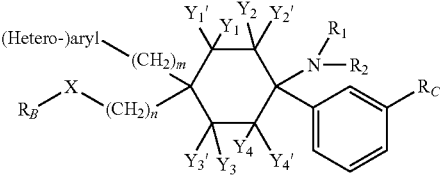

(2.14) 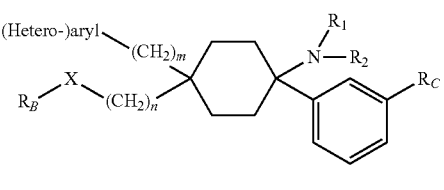

[Aliphat=Aliphatic]
wherein
$R_C$ stands for —H, —F, —Cl, —Br, —I, —CN, —NO$_2$, —CF$_3$, —OH or —OCH$_3$; and, where present, (hetero)aryl stands for heteroaryl or aryl; preferably for -phenyl, -benzyl or -2-indolyl; respectively unsubstituted or mono- or polysubstituted, wherein the substituents are preferably selected independently of one another from the group comprising —F, —Cl, —Br, —I, —CN, —NO$_2$, —CHO, —R$_0$, —C(═O)R$_0$, —C(═O)H, —C(═O)OH, —C(═O)OR$_0$, —C(═O)NH$_2$, —C(═O)—NH—R$_0$, —C(═O)—N(R$_0$)$_2$, —OH, —O(CH$_2$)$_{1-2}$O—, —OR$_0$, —OC(═O)H, —OC(═O)R$_0$, —OC(═O)OR$_0$, —OC(═O)NHR$_0$, —OC(═O)N(R$_0$)$_2$, —SH, —SR$_0$, —SO$_3$H, —S(═O)$_{1-2}$—R$_0$, —S(═O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(═O)R$_0$, —NHC(═O)—OR$_0$, —NH—C(═O)NH$_2$, —NHC(═O)NHR$_0$ and —NHC(═O)N(R$_0$)$_2$; more preferred —F, —Cl, —Br, —I, —CF$_3$, —CN and —NO$_2$; and m stands for 0, 1, 2, 3, 4, 5 or 6.

Preferred representatives of the compounds of the general formula (2.14) are e.g. the compounds E-1 to E-12:

E-1

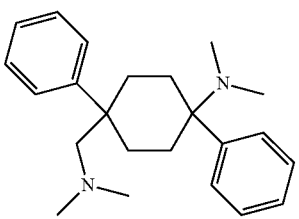

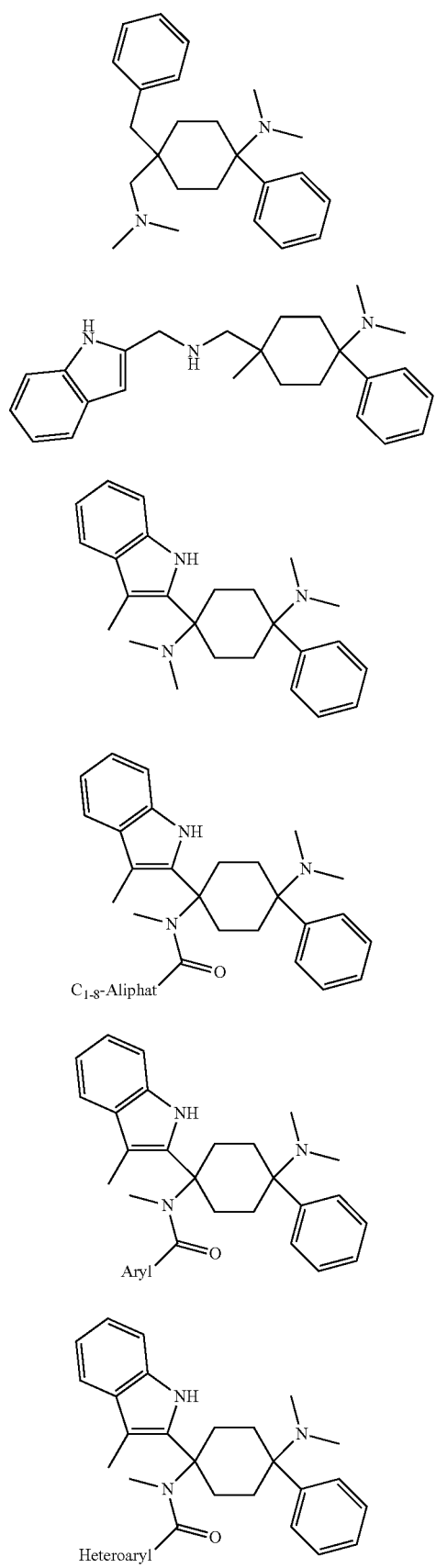
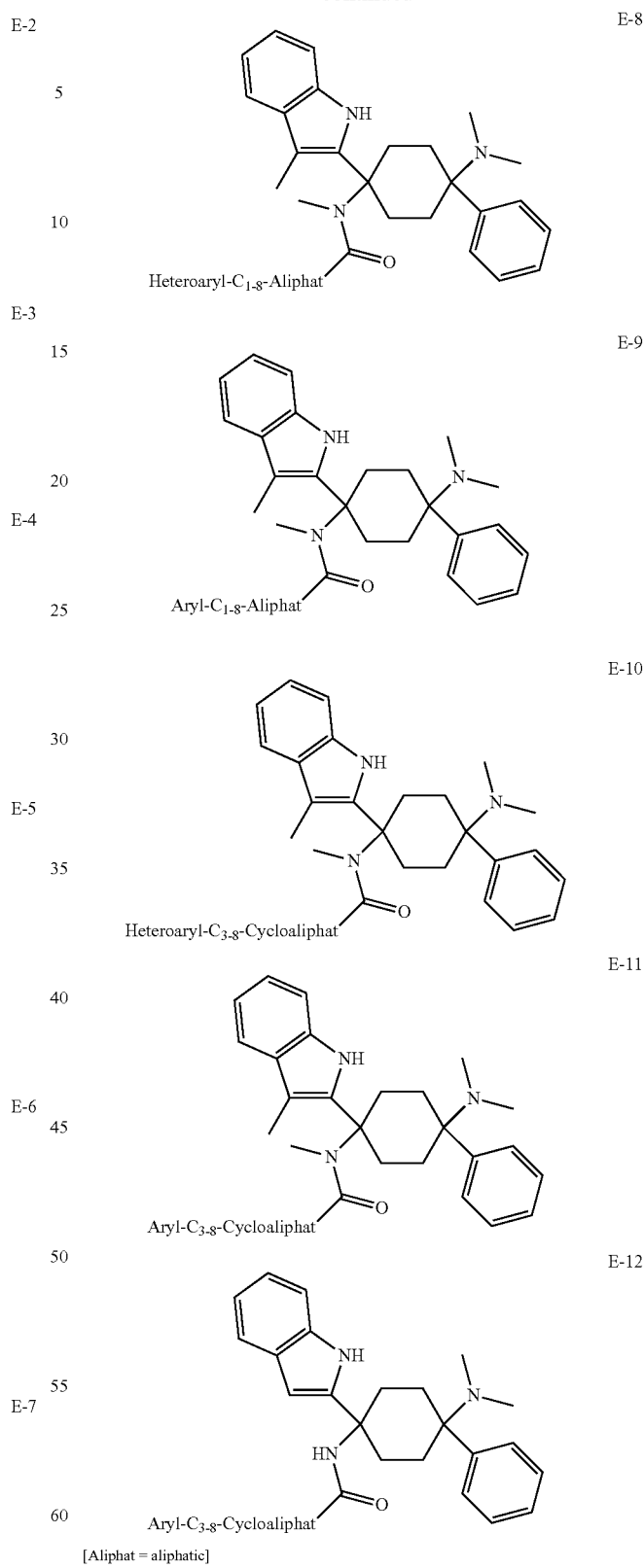
[Aliphat = aliphatic]
Further preferred embodiments of the compounds according to the invention of the general formula (1) have the general formula (3):

(3)

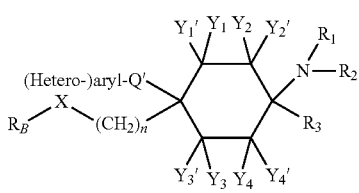

wherein

Q' stands for —(CH$_2$)$_{0-4}$—, —C(=O)— or —C(=NH)—; and (hetero-)aryl stands for heteroaryl or aryl; preferably phenyl; respectively unsubstituted or mono- or polysubstituted, wherein the substituents are preferably selected independently of one another from the group comprising —F, —Cl, —Br, —I, —CN, —NO$_2$, —CHO, —R$_0$, —C(=O)R$_0$, —C(=O)H, —C(=O)OH, —C(=O)OR$_0$, —C(=O)NH$_2$, —C(=O)NH—R$_0$, —C(=O)—N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, -N(R$_0$)$_2$, —N$^+$(R$_0$)$_3$, —N$^+$(R$_0$)$_2$O$^-$, —NHC(=O)R$_0$, —NHC(=O)—OR$_0$, —NH—C(=O)NH$_2$, —NHC(=O)NHR$_0$ and —NHC(=O)N(R$_0$)$_2$; more preferred —F, —Cl, —Br, —I, —CF$_3$, —CN and —NO$_2$.

Particularly preferred embodiments of the compounds according to the invention of general formula (3) have the general formula (3.1), (3.2), (3.3), (3.4), (3.5), (3.6), (3.7) or (3.8):

(3.1)

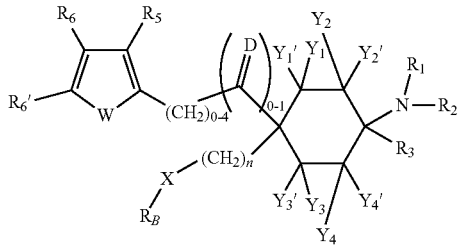

(3.2)

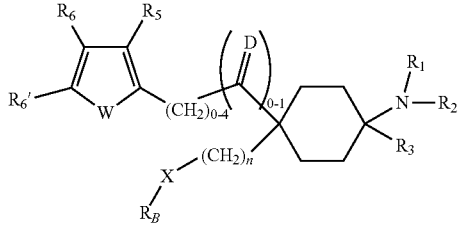

(3.3)

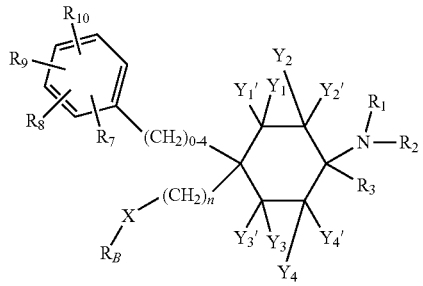

(3.4)

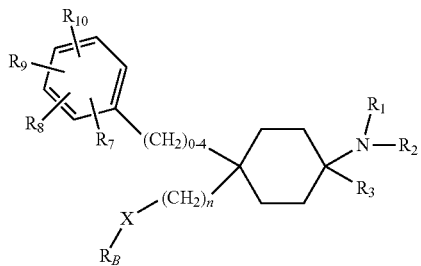

(3.5)

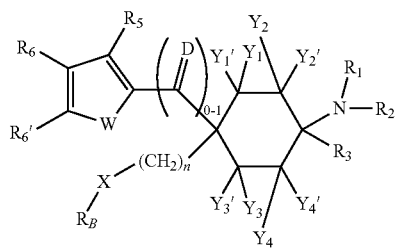

(3.6)

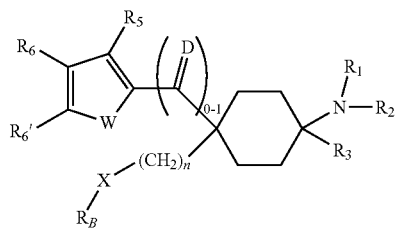

(3.7)

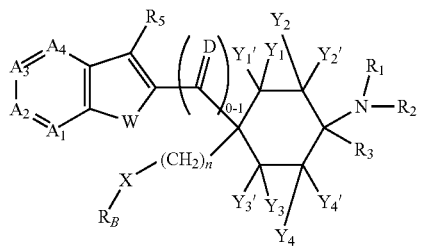

(3.8)

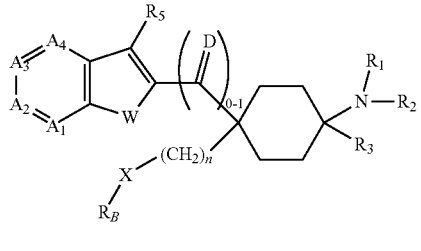

(3.9)

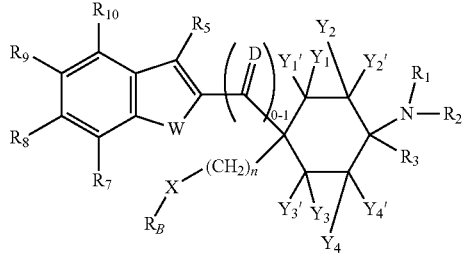

-continued (3.10)

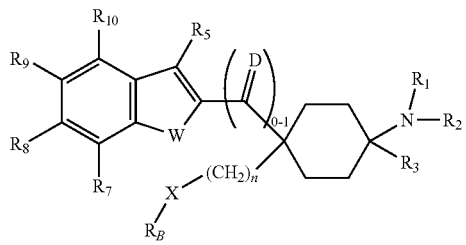

wherein, where present,

D stands for =O or =NH;

W stands for —O—, —S—, —NR₁₁—, —CR₁₂=CR₁₃—, —CR₁₂=N— or —N=CR₁₃—; preferably for —O—, —S—, or —NR₁₁—; particularly preferred for —NR₁₁—;

$R_5$, $R_6$, $R_6'$, $R_{11}$, $R_{12}$ and $R_{13}$ respectively independently of one another stand for —H, —F, —Cl, —Br, —I, —CN, —NO₂, —CHO, —R₀, —C(=O)R₀, —C(=O)H, —C(=O)OH, —C(=O)OR₀, —C(=O)NH₂, —C(=O)NHR₀, —C(=O)—N(R₀)₂, —OH, —O(CH₂)₁₋₂O—, —OR₀, —OC(=O)H, —OC(=O)R₀, —OC(=O)OR₀, —OC(=O)NHR₀, —OC(=O)N(R₀)₂, —SH, —SR₀, —SO₃H, —S(=O)₁₋₂—R₀, —S(=O)₁₋₂NH₂, —NH₂, —NHR₀, —N(R₀)₂, —N⁺(R₀)₃, —N⁺(R₀)₂O⁻, —NHC(=O)R₀, —NHC(=O)OR₀, —NH—C(=O)NH₂, —NHC(=O)NHR₀, —NHC(=O)N(R₀)₂; or $R_5$ and $R_6$, or $R_6$ and $R_6'$, or $R_6$ and $R_{12}$ together form a five- or six-membered, saturated, partially unsaturated or aromatic, unsubstituted or mono- or polysubstituted ring, which possibly comprises one or two hetero ring atoms selected independently of one another from N, S and O;

$A_1$ stands for —N= or —CR₇=, $A_2$ stands for —N= or —CR₈=, $A_3$ stands for —N= or —CR₉=, $A_4$ stands for —N= or —CR₁₀=;

on condition that at most two of the residues $A_1$, $A_2$, $A_3$ and $A_4$, preferably 0, 1 or 2 of the residues $A_1$, $A_2$, $A_3$ and $A_4$, stand for —N=;

$R_7$, $R_8$, $R_9$ and $R_{10}$ respectively independently of one another stand for —H, —F, —Cl, —Br, —I, —NO₂, —CF₃, —OR₁₄, —SR₁₄, —SO₂R₁₄, —CN, —COOR₁₄, —CONR₁₄, —NR₁₅R₁₆, =O or —R₀; preferably for —F, —Cl, —Br, —I, —CF₃, —CN or —NO₂;

$R_{14}$ respectively independently stands for —H or —R₀;

$R_{15}$ and $R_{16}$ independently of one another stand for —H or —R₀; or $R_{15}$ and $R_{16}$ together stand for —CH₂CH₂OCH₂CH₂—, —CH₂CH₂NR₄CH₂CH₂— or —(CH₂)₃₋₆—.

If, for example, W stands for —CR₁₂=CR₁₃—, —CR₁₂=N— or —N=CR₁₃—, then the following functional groups preferably result:

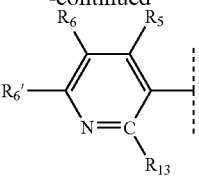

If, for example, $R_6$ and $R_6'$ together form a six-membered aromatic ring that has no hetero ring atoms, then the following functional groups respectively result:

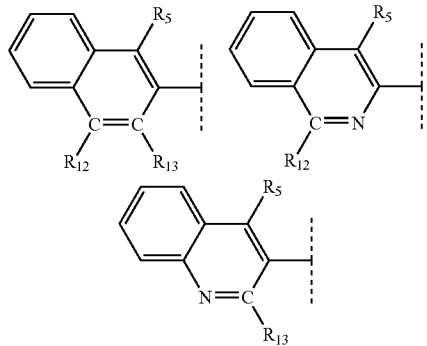

The five- or six-membered, saturated, partially unsaturated or aromatic ring possibly formed by $R_5$ and $R_6$ or $R_6$ and $R_6'$ or $R_6'$ and $R_{12}$ together can comprise one or two hetero ring atoms, which are selected independently of one another from N, S and O. Moreover, this ring can be unsubstituted or mono- or polysubstituted, wherein the substituents are preferably selected independently of one another from the group comprising F, —Cl, —Br, —I, —CN, —NO₂, —CHO, —R₀, —C(=O)R₀, —C(=O)H, —C(=O)OH, —C(=O)OR₀, —C(=O)NH₂, —C(=O)NHR₀, —C(=O)—N(R₀)₂, —OH, —O(CH₂)₁₋₂O—, —OR₀, —OC(=O)H, —OC(=O)R₀, —OC(=O)OR₀, —OC(=O)NHR₀; —OC(=O)N(R₀)₂, —SH, —SR₀, —SO₃H, —S(=O)₁₋₂—R₀, —S(=O)₁₋₂NH₂, —NH₂, —NHR₀, —N(R₀)₂, —N⁺(R₀)₃, —N⁺(R₀)₂O⁻, —NHC(=O)R₀, —NHC(=O)OR₀, —NH—C(=O)NH₂, —NHC(=O)NHR₀ and —NHC(=O)N(R₀)₂; more preferred —F, —Cl, —Br, —I, —CF₃, —CN and —NO₂.

$R_5$ preferably stands for —H, —F, —Cl or —R₀; more preferred for —H, —F, —C₁₋₈-aliphatic, —C₁₋₈-aliphatic-aryl, —C₁₋₈-aliphatic-heteroaryl or —C₁₋₈-aliphatic-O—C₁₋₈-aliphatic (e.g. —CH₂OCH₃).

It is preferred if $R_6$ and $R_6'$ together form a six-membered, saturated, partially unsaturated or aromatic ring, which can possibly comprise one or two hetero ring atoms that are selected independently of one another from N, S and O. This formed ring can be unsubstituted or mono- or polysubstituted, wherein the substituents are preferably selected independently of one another from the group comprising —F, —Cl, —Br, —I, —CN, —NO₂, —CHO, —R₀, —C(=O)R₀, —C(=O)H, —C(=O)OH, —C(=O)OR₀, —C(=O)NH₂, —C(=O)NHR₀, —C(=O)—N(R₀)₂, —OH, —O(CH₂)₁₋₂O—, —OR₀, —OC(=O)H, —OC(=O)R₀, —OC(=O)OR₀, —OC(=O)NHR₀, —OC(=O)—N(R₀)₂, —SH, —SR₀, —SO₃H, —S(=O)₁₋₂—R₀, —S(=O)₁₋₂NH₂, —NH₂, —NHR₀, —N(R₀)₂, —N⁺(R₀)₃, —N⁺(R₀)₂O⁻, —NHC(=O)R₀, —NHC(=O)OR₀,

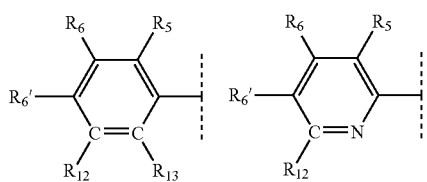

—NH—C(=O)NH$_2$, —NHC(=O)NHR$_0$ and —NHC(=O)N(R$_0$)$_2$; more preferred —F, —Cl, —Br, —I, —CF$_3$, —CN and —NO$_2$.

R$_{11}$, R$_{12}$ and R$_{13}$ are preferably selected independently of one another from the group comprising —H, —F, —Cl, —CN, —OH, —R$_0$ and —OR$_0$. It is particularly preferred if R$_{11}$, R$_{12}$ and R$_{13}$—where present—are respectively —H.

Further preferred embodiments of the compounds according to the invention of the general formula (1) have the general formula (4):

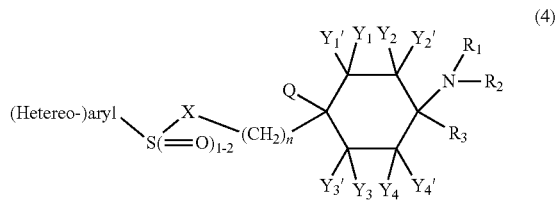

(4)

wherein (hetero)aryl stands for heteroaryl or aryl; preferably phenyl; respectively unsubstituted or mono- or polysubstituted, wherein the substituents are preferably selected independently of one another from the group comprising —F, —Cl, —Br, —I, —CN, —NO$_2$, —CHO, —R$_0$, —C(=O)R$_0$, —C(=O)H, —C(=O)OH, —C(=O)OR$_0$, —C(=O)NH$_2$, —C(=O)NH—R$_0$, —C(=O)—N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)—OR$_0$, —NH—C(=O)NH$_2$, —NHC(=O)NHR$_0$ and —NHC(=O)N(R$_0$)$_2$; more preferred —F, —Cl, —Br, —I, —CF$_3$, —CN and —NO$_2$.

The compounds according to the invention are defined by substituents, e.g. by R$_1$, R$_2$ and R$_3$ (substituents of the first generation), which are themselves possibly substituted (substituents of the second generation). Depending on the definition, these substituents of the substituents can themselves be substituted again (substituents of the third generation). If, for example, Y$_1$=—R$_0$, wherein —R$_0$=—C$_{1-8}$-aliphatic (substituent of the first generation), then —C$_{1-8}$-aliphatic can itself be substituted, e.g. with —OR$_0$, wherein R$_0$=-aryl (substituent of the second generation). This gives the functional group —C$_{1-8}$-aliphatic-Oaryl. -Aryl can then in turn be substituted again, e.g. with —Cl (substituent of the third generation). This then gives overall the functional group —C$_{1-8}$-aliphatic-Oaryl-Cl.

In a preferred embodiment, the substituents of the third generation cannot be substituted again, i.e. there are then no substituents of the fourth generation.

In another preferred embodiment, the substituents of the second generation cannot be substituted again, i.e. there are then already no substituents of the third generation. In other words, in this embodiment the functional groups for R$_0$ to Y$_4$' can possibly be respectively substituted, but the respective substituents cannot then themselves be substituted again.

In another preferred embodiment, the substituents of the first generation cannot be substituted again, i.e. there are then neither substituents of the second generation nor substituents of the third generation. In other words, in this embodiment the functional groups for R$_0$ to Y$_4$' are not respectively substituted.

Embodiments of the compounds of the general formula (1) that are particularly preferred according to the invention are compounds of the general formula (2.2)

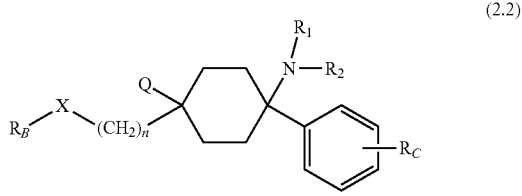

(2.2)

wherein

Q stands for —C$_{1-8}$-aliphatic (preferably —C$_{1-8}$-alkyl), -aryl (preferably -phenyl), —C$_{1-8}$-aliphatic-aryl (preferably —C$_{1-8}$-alkyl-phenyl), -heteroaryl (preferably -indolyl), —C(=O)-heteroaryl (preferably —C(=O)-indolyl) or —C(=NH)-heteroaryl (preferably —C(=NH)-indolyl);

R$_1$ stands for —CH$_3$;

R$_2$ stands for —H or —CH$_3$; or

R$_1$ and R$_2$ jointly form a ring and stand for —(CH$_2$)$_{3-4}$—;

X stands for —O— or —NR$_A$—;

R$_A$ stands for —H or —C$_{1-8}$-aliphatic (preferably —C$_{1-8}$-alkyl);

R$_B$ stands for —H, —C$_{1-8}$-aliphatic (preferably —C$_{1-8}$-alkyl), —C$_{1-8}$-aliphatic-aryl (preferably —C$_{1-8}$-alkyl-phenyl), —C$_{1-8}$-aliphatic-heteroaryl (preferably —C$_{1-8}$-alkyl-indolyl), —C(=O)—C$_{1-8}$-aliphatic (preferably —C(=O)—C$_{1-8}$-alkyl), —C(=O)—C$_{1-8}$-aliphatic-aryl (preferably —C(=O)-benzyl), —C(=O)—C$_{1-8}$-aliphatic-heteroaryl (preferably —C(=O)—C$_{1-8}$-alkyl-indolyl), —C(=O)—C$_{3-8}$-cycloaliphatic-aryl (preferably —C(=O)-cyclopropyl-aryl), —C(=O)—C$_{3-8}$-cycloaliphatic-heteroaryl (preferably —C(=O)-cyclopropyl-heteroaryl), —C(=O)NH—C$_{1-8}$-aliphatic (preferably —C(=O)NH—C$_{1-8}$-alkyl), —S(=O)$_{1-2}$—C$_{1-8}$-aliphatic (preferably —S(=O)$_2$—C$_{1-8}$-alkyl), —S(=O)$_{1-2}$-aryl (preferably —S(=O)$_2$-phenyl), —S(=O)$_{1-2}$-heteroaryl, —S(=O)$_{1-2}$—C$_{1-8}$-aliphatic-aryl, —S(=O)$_{1-2}$—C$_{1-8}$-aliphatic-heteroaryl, —S(=O)$_{1-2}$—C$_{3-8}$-cycloaliphatic-aryl (preferably —S(=O)$_2$-cyclopropyl-aryl) or —S(=O)$_{1-2}$—C$_{3-8}$-cycloaliphatic-heteroaryl (preferably —S(=O)$_2$-cyclopropyl-heteroaryl); or R$_A$ and R$_B$ jointly form a ring and stand for —(CH$_2$)$_{3-4}$—; on condition that when X stands for —O— and n at the same time stands for 0, R$_B$ does not stand for —H;

R$_C$ stands for —H, —F, —Cl, —Br, —I, —CN, —NO$_2$, —CF$_3$, —OH or —OCH$_3$; and n stands for 0, 1, 2, 3 or 4;

wherein aliphatic, aryl and heteroaryl are respectively unsubstituted or mono- or polysubstituted.

Compounds from the following group are most particularly preferred:

1-(imino(1-methyl-1H-indol-2-yl)methyl)-N1,N1,N4,N4-tetramethyl-4-phenylcyclohexane-1,4-diamine bis(2-hydroxypropane-1,2,3-tricarboxylate);

4-(dimethylamino)-4-phenyl-1-(pyrrolidin-1-yl)cyclohexyl) (1-methyl-1H-indol-2-yl)methanone;

1-(imino(1-methyl-1H-indol-2-yl)methyl)-N1,N1,N4,N4-tetramethyl-4-phenylcyclohexane-1,4-diamine bis(2-hydroxypropane-1,2,3-tricarboxylate);

1,4-bis(dimethylamino)-4-phenylcyclohexyl)(1-methyl-1H-indol-2-yl)methanone;

4-(imino(1-methyl-1H-indol-2-yl)methyl)-N,N-dimethyl-1-phenyl-4-(pyrrolidin-1-yl)cyclohexanamine;

4-(dimethylamino)-4-phenyl-1-(pyrrolidin-1-yl)cyclohexyl)(1-methyl-1H-indol-2-yl)methanone;

N1,N1,N4-trimethyl-1,4-diphenylcyclohexane-1,4-diamine;

N1,N1,N4,N4-tetramethyl-1,4-diphenylcyclohexane-1,4-diamine;

1-benzyl-N1,N1,N4,N4-tetramethyl-4-phenylcyclohexane-1,4-diamine;

4-methoxy-4-(3-(methoxymethyl)-1H-indol-2-yl)-N,N-dimethyl-1-phenylcyclohexanamine 2-hydroxypropane-1,2,3-tricarboxylate;

4-(benzyloxy)-4-(3-(methoxymethyl)-1H-indol-2-yl)-N,N-dimethyl-1-phenylcyclohexanamine;

4-ethoxy-4-(3-(methoxymethyl)-1H-indol-2-yl)-N,N-dimethyl-1-phenylcyclohexanamine 2-hydroxypropane-1,2,3-tricarboxylate;

N-((-4-(dimethylamino)-1-methyl-4-phenylcyclohexyl)methyl)acetamide 2-hydroxypropane-1,2,3-tricarboxylate;

4-chloro-N-((-4-(dimethylamino)-1-methyl-4-phenylcyclohexyl)methyl)benzol-sulphonamide 2-hydroxypropane-1,2,3-tricarboxylate;

N-((1-butyl-4-(dimethylamino)-4-phenylcyclohexyl)methyl)-4-chlorobenzol-sulphonamide 2-hydroxypropane-1,2,3-tricarboxylate;

N-((-4-(dimethylamino)-4-phenyl-1-(4-phenylbutyl)cyclohexyl)methanol;

N(4-((dimethylamino)methyl)-N,N-dimethyl-1,4-diphenylcyclohexanamine;

4-benzyl-4-((dimethylamino)methyl)-N,N-dimethyl-1-phenylcyclohexanamine;

4-(((1H-indol-2-yl)methylamino)methyl)-N,N,4-trimethyl-1-phenylcyclohexanamine;

N1,N1,N4,N4-tetramethyl-1-(3-methyl-1H-indol-2-yl)-4-phenylcyclohexane-1,4-diamine;

N-(4-(dimethylamino)-1-(3-methyl-1H-indol-2-yl)-4-phenylcyclohexyl)-N-methyl-cinnamamide;

N-(4-(dimethylamino)-1-(3-methyl-1H-indol-2-yl)-4-phenylcyclohexyl)-N-methyl-acetamide;

[4-benzyl-4-(dimethylaminomethyl)-1-phenyl-cyclohexyl]-dimethylamine;

(4-dimethylamino-1,4-diphenyl-cyclohexyl)-methyl-dimethylamine (non-polar diastereomer);

(E)-N-(4-dimethylamino-1,4-diphenyl-cyclohexyl)-N-methyl-3-phenyl-acrylamide (non-polar diastereomer);

N-(4-dimethylamino-1,4-diphenyl-cyclohexyl)-N-methyl-acetamide (non-polar diastereomer);

N-(4-dimethylamino-1,4-diphenyl-cyclohexyl)-N-methyl-methanesulphonamide (polar diastereomer);

(E)-N-(4-dimethylamino-1,4-diphenyl-cyclohexyl)-N-methyl-3-phenyl-acrylamide (polar diastereomer);

N-(4-dimethylamino-1,4-diphenyl-cyclohexyl)-N-methyl-acetamide (polar diastereomer);

3-benzyl-1-(4-dimethylamino-1,4-diphenyl-cyclohexyl)-1-methyl-urea (non-polar diastereomer);

3-benzyl-1-(4-dimethylamino-1,4-diphenyl-cyclohexyl)-1-methyl-urea (polar diastereomer);

1-(4-dimethylamino-1,4-diphenyl-cyclohexyl)-3-ethyl-1-methyl-urea (non-polar diastereomer);

1-(4-dimethylamino-1,4-diphenyl-cyclohexyl)-3-ethyl-1-methyl-urea (polar diastereomer);

(4-benzyl-4-((dimethylamino)methyl)-N-methyl-1-phenyl-cyclohexanamine (polar diastereomer);

(1-benzyl-4-dimethylamino-4-phenyl-cyclohexyl)-methyl-dimethylamine (polar diastereomer);

[4-(dimethylamino)-4-(3-methyl-1H-indol-2-yl)-1-phenyl-cyclohexyl]-dimethylamine (polar diastereomer);

[4-dimethylamino-4-(3-methyl-1H-indol-2-yl)-1-phenyl-cyclohexyl]-dimethylamine (non-polar diastereomer);

[4-(dimethylaminomethyl)-1,4-diphenyl-cyclohexyl]-dimethylamine (polar diastereomer);

dimethyl-(4-methylamino-4-phenyl-1-thiophen-2-yl-cyclohexyl)-amine (non-polar diastereomer);

dimethyl-(4-methylamino-4-phenyl-1-thiophen-2-yl-cyclohexyl)-amine (polar diastereomer);

[4-(dimethylamino)-4-phenyl-1-thiophen-2-yl-cyclohexyl]-dimethylamine (polar diastereomer);

(4-dimethylamino-4-phenyl-1-thiophen-2-yl-cyclohexyl)-dimethylamine (non-polar diastereomer);

(E)-N-[[4-dimethylamino-4-(3-fluorophenyl)-1-methyl-cyclohexyl]-methyl]-3-phenyl-acrylamide (polar diastereomer);

(E)-N-[[4-dimethylamino-4-(3-fluorophenyl)-1-methyl-cyclohexyl]-methyl]-3-phenyl-acrylamide (non-polar diastereomer);

(E)-N-[[4-dimethylamino-4-(3-fluorophenyl)-1-methyl-cyclohexyl]-methyl]-2-phenyl-ethylene sulphonamide (non-polar diastereomer);

(E)-N-[[4-dimethylamino-4-(3-fluorophenyl)-1-methyl-cyclohexyl]-methyl]-2-phenyl-ethylene sulphonamide (polar diastereomer);

(1-butyl-4-methylamino-4-phenyl-cyclohexyl)-dimethylamine (non-polar diastereomer);

(1-butyl-4-methylamino-4-phenyl-cyclohexyl)-dimethylamine (polar diastereomer);

[4-(butyl-methyl-amino)-1,4-diphenyl-cyclohexyl]-dimethylamine (non-polar diastereomer);

[4-(butyl-methyl-amino)-1,4-diphenyl-cyclohexyl]-dimethylamine (polar diastereomer);

[4-(benzyl-methyl-amino)-1,4-diphenyl-cyclohexyl]-dimethylamine (non-polar diastereomer);

[4-(benzyl-methyl-amino)-1,4-diphenyl-cyclohexyl]-dimethylamine (polar diastereomer);

N-[4-(dimethyl-amino)-1,4-diphenyl-cyclohexyl]-N-methyl-2,2-diphenyl-acetamide (polar diastereomer);

dimethyl-[4-(3-methyl-1H-indol-2-yl)-1-phenyl-4-pyrrolidin-1-yl-cyclohexyl]-amine dihydrochloride (polar diastereomer);

dimethyl-[4-(3-methyl-1H-indol-2-yl)-1-phenyl-4-pyrrolidin-1-yl-cyclohexyl]-amine;

[4-(acetidin-1-yl)-4-(3-methyl-1H-indol-2-yl)-1-phenyl-cyclohexyl]-dimethylamine (non-polar diastereomer);

N-(4-dimethylamino-1,4-diphenyl-cyclohexyl)-N-methyl-methanesulphonamide (non-polar diastereomer);

(4-butyl-4-dimethylamino-1-phenyl-cyclohexyl)-dimethylamine (non-polar diastereomer);

(4-butyl-4-dimethylamino-1-phenyl-cyclohexyl)-dimethylamine (polar diastereomer);

[4-(cyclopentyl-methyl)-4-dimethylamino-1-phenyl-cyclohexyl]-methylamine (non-polar diastereomer);

[4-(cyclopentyl-methyl)-4-dimethylamino-1-phenyl-cyclohexyl]-methylamine (polar diastereomer);

[4-(cyclopentyl-methyl)-4-dimethylamino-1-phenyl-cyclohexyl]-dimethylamine (non-polar diastereomer);

[4-(cyclopentyl-methyl)-4-dimethylamino-1-phenyl-cyclohexyl]-dimethylamine (polar diastereomer);

(E)-N-[4-(cyclopentyl-methyl)-4-dimethylamino-1-phenyl-cyclohexyl]-N-methyl-3-phenyl-acrylamide (non-polar diastereomer);

(E)-N-[4-(cyclopentyl-methyl)-4-dimethylamino-1-phenyl-cyclohexyl]-N-methyl-3-phenyl-acrylamide (polar diastereomer);

2-[(4-dimethylamino-1,4-diphenyl-cyclohexyl)-methylamino]-acetic acid (polar diastereomer);

2-[(4-dimethylamino-1,4-diphenyl-cyclohexyl)-methyl-
  amino]-acetic acid (non-polar diastereomer);
[1-(4-methoxyphenyl)-4-methylamino-4-phenyl-cyclo-
  hexyl]-dimethylamine (non-polar diastereomer);
[1-(4-methoxyphenyl)-4-methylamino-4-phenyl-cyclo-
  hexyl]-dimethylamine (polar diastereomer);
dimethyl-[4-methylamino-4-phenyl-1-[4-(trifluoromethyl)-
  phenyl]-cyclohexyl]-amine (non-polar diastereomer);
dimethyl-[4-methylamino-4-phenyl-1-[4-(trifluoromethyl)-
  phenyl]-cyclohexyl]-amine (polar diastereomer);
[4-(dimethylamino)-4-phenyl-1-[4-(trifluoromethyl)-phe-
  nyl]-cyclohexyl]-dimethylamine (polar diastereomer);
[4-dimethylamino-4-phenyl-1-[4-(trifluoromethyl)-phenyl]-
  cyclohexyl]-dimethylamine (non-polar diastereomer);
[4-(dimethylamino)-1-(4-methoxyphenyl)-4-phenyl-cyclo-
  hexyl]-dimethylamine (polar diastereomer);
[4-dimethylamino-1-(4-methoxyphenyl)-4-phenyl-cyclo-
  hexyl]-dimethylamine (non-polar diastereomer);
[4-[(1H-indol-3-yl-methylamino)-methyl]-4-methyl-1-phe-
  nyl-cyclohexyl]-dimethylamine (non-polar diaste-
  reomer);
[4-[(1H-indol-3-yl-methylamino)-methyl]-4-methyl-1-phe-
  nyl-cyclohexyl]-dimethylamine (polar diastereomer);
[4-[(1H-indol-3-yl-methyl-methyl-amino)-methyl]-4-
  methyl-1-phenyl-cyclohexyl]-dimethylamine (non-polar
  diastereomer);
[4-[(1H-indol-3-yl-methyl-methyl-amino)-methyl]-4-
  methyl-1-phenyl-cyclohexyl]-dimethylamine (polar
  diastereomer);
[3-[[[4-(dimethyl-amino)-1-methyl-4-phenyl-cyclohexyl]-
  methyl-methylamino]-methyl]-1H-indol-1-yl]-methanol
  (polar diastereomer);
(E)-N-[4-dimethylamino-1-(3-methyl-1H-indol-2-yl)-4-
  phenyl-cyclohexyl]-N-methyl-3-phenyl-acrylamide (po-
  lar diastereomer);
[4-dimethylamino-1-(3-methyl-1H-indol-2-yl)-4-phenyl-
  cyclohexyl]-methylamine (polar diastereomer);
[4-dimethylamino-1-(3-methyl-1H-indol-2-yl)-4-phenyl-
  cyclohexyl]-methylamine (non-polar diastereomer);
benzyl-[4-dimethylamino-1-(3-methyl-1H-indol-2-yl)-4-
  phenyl-cyclohexyl]-amine;
2-hydroxy-propane-1,2,3-tricarboxylic acid;
dimethyl-[4-[methyl-(pyridin-3-yl-methyl)-amino]-1,4-di-
  phenyl-cyclohexyl]-amine (polar diastereomer);
[4-[[4,6-bis(methylamino)-[1,3,5]triazin-2-yl]-methyl-
  amino]-1,4-diphenyl-cyclohexyl]-dimethylamine (non-
  polar diastereomer);
[4-[[4-(4-methoxy-phenoxy)-6-methylamino-[1,3,5]triazin-
  2-yl]-methyl-amino]-1,4-diphenyl-cyclohexyl]-dimethyl-
  amine (non-polar diastereomer);
N-[4-(dimethylamino)-1,4-diphenyl-cyclohexyl]-N-methyl-
  pyridin-3-carboxylic acid amide (non-polar diaste-
  reomer);
dimethyl-[4-[methyl-(pyridin-3-yl-methyl)-amino]-1,4-di-
  phenyl-cyclohexyl]-amine (non-polar diastereomer);
[4-[[4,6-bis(methylamino)-[1,3,5]triazin-2-yl]-methyl-
  amino]-1,4-diphenyl-cyclohexyl]-dimethylamine (polar
  diastereomer);
[4-[[4-(4-methoxy-phenoxy)-6-methylamino-[1,3,5]triazin-
  2-yl]-methyl-amino]-1,4-diphenyl-cyclohexyl]-dimethyl-
  amine (polar diastereomer);
N-[4-(dimethylamino)-1,4-diphenyl-cyclohexyl]-N,1-dim-
  ethyl-1H-pyrazol-3-carboxylic acid amide (polar diaste-
  reomer);
N-[4-(dimethylamino)-1,4-diphenyl-cyclohexyl]-N,1-dim-
  ethyl-1H-pyrazol-3-carboxylic acid amide (non-polar
  diastereomer);
[4-(dimethylamino)-1-(3-fluorophenyl)-4-(3-methyl-1H-in-
  dol-2-yl)-cyclohexyl]-dimethylamine (polar diaste-
  reomer);
4-(acetidin-1-yl)-1-(3-fluorophenyl)-N,N-dimethyl-4-(3-
  methyl-1H-indol-2-yl)cyclohexanamine (non-polar
  diastereomer);
4-(acetidin-1-yl)-1-(3-fluorophenyl)-N,N-dimethyl-4-(3-
  methyl-1H-indol-2-yl)cyclohexanamine (polar diaste-
  reomer);
[4-dimethylamino-1-(3-fluorophenyl)-4-(3-methyl-1H-in-
  dol-2-yl)-cyclohexyl]-dimethylamine (non-polar diaste-
  reomer);
N-(4-dimethylamino-1,4-diphenyl-cyclohexyl)-N-methyl-
  3-(trifluoromethyl)-benzamide (non-polar diastereomer);
N-(4-dimethylamino-1,4-diphenyl-cyclohexyl)-N-methyl-
  3-(trifluoromethyl)-benzamide (polar diastereomer);
[4-[[4,6-bis(4-methoxy-phenoxy)-[1,3,5]triazin-2-yl]-
  methyl-amino]-1,4-diphenyl-cyclohexyl]-dimethylamine
  (polar diastereomer);
(4-dimethylamino-1,4-diphenyl-cyclohexyl)-methyl-[(1-
  methyl-1H-pyrazol-3-yl)-methyl]-amine (polar diaste-
  reomer);
(4-dimethylamino-1,4-diphenyl-cyclohexyl)-methyl-[(1-
  methyl-1H-pyrazol-3-yl)-methyl]-amine (non-polar
  diastereomer);
[4-[[4,6-bis(4-methoxy-phenoxy)-[1,3,5]triazin-2-yl]-
  methyl-amino]-1,4-diphenyl-cyclohexyl]-dimethylamine
  (non-polar diastereomer);
N-(4-dimethylamino-1,4-diphenyl-cyclohexyl)-4-methoxy-
  N-methyl-benzamide (non-polar diastereomer);
N-(4-dimethylamino-1,4-diphenyl-cyclohexyl)-4-methoxy-
  N-methyl-benzamide (polar diastereomer);
(4-dimethylamino-1,4-diphenyl-cyclohexyl)-[(4-methoxy-
  phenyl)-methyl]-methylamine (polar diastereomer);
(4-dimethylamino-1,4-diphenyl-cyclohexyl)-[(4-methoxy-
  phenyl)-methyl]-methylamine (non-polar diastereomer);
[1-(3-fluorophenyl)-4-(3-methyl-1H-indol-2-yl)-4-pyrroli-
  din-1-yl-cyclohexyl]-dimethylamine (non-polar diaste-
  reomer);
[1-(3-fluorophenyl)-4-(3-methyl-1H-indol-2-yl)-4-pyrroli-
  din-1-yl-cyclohexyl]-dimethylamine (polar diaste-
  reomer);
[1-(3-fluorophenyl)-4-methylamino-4-(3-methyl-1H-indol-
  2-yl)-cyclohexyl]-dimethylamine;
dimethyl-[4-(3-methyl-1H-indol-2-yl)-1-phenyl-4-piperi-
  din-1-yl-cyclohexyl]-amine (non-polar diastereomer);
[1-(3-fluorophenyl)-4-(3-methyl-1H-indol-2-yl)-4-piperi-
  din-1-yl-cyclohexyl]-dimethylamine (polar diaste-
  reomer);
[4-(dimethylamino)-4-(5-fluoro-3-methyl-1H-indol-2-yl)-1-
  phenyl-cyclohexyl]-dimethylamine (polar diastereomer);
(4-dimethylamino-1,4-diphenyl-cyclohexyl)-methyl-[[3-
  (trifluoromethyl)phenyl]-methyl]-amine (polar diaste-
  reomer);
(4-dimethylamino-1,4-diphenyl-cyclohexyl)-methyl-[[3-
  (trifluoromethyl)phenyl]-methyl]-amine (non-polar
  diastereomer);
N-(4-dimethylamino-1,4-diphenyl-cyclohexyl)-3-fluoro-N-
  methyl-benzamide (non-polar diastereomer);
N-(4-dimethylamino-1,4-diphenyl-cyclohexyl)-3-fluoro-N-
  methyl-benzamide (polar diastereomer);
(4-dimethylamino-1,4-diphenyl-cyclohexyl)-[(3-fluorophe-
  nyl)-methyl]-methylamine (non-polar diastereomer);
(4-dimethylamino-1,4-diphenyl-cyclohexyl)-[(3-fluorophe-
  nyl)-methyl]-methylamine (polar diastereomer);
2-[(4-dimethylamino-1,4-diphenyl-cyclohexyl)-methyl-
  amino]-ethanol (polar diastereomer);

2-[(4-dimethylamino-1,4-diphenyl-cyclohexyl)-methyl-amino]-N,N-dimethyl-acetamide (polar diastereomer);
2-[(4-dimethylamino-1,4-diphenyl-cyclohexyl)-methyl-amino]-N-methyl-acetamide (polar diastereomer);
2-[(4-dimethylamino-1,4-diphenyl-cyclohexyl)-methyl-amino]-N,N-dimethyl-acetamide (non-polar diastereomer);
2-[(4-dimethylamino-1,4-diphenyl-cyclohexyl)-methyl-amino]-N-methyl-acetamide (non-polar diastereomer);
[4-dimethylamino-4-(5-fluoro-3-methyl-1H-indol-2-yl)-1-phenyl-cyclohexyl]-dimethylamine (non-polar diastereomer);
[4-(5-fluoro-3-methyl-1H-indol-2-yl)-1-phenyl-4-pyrrolidin-1-yl-cyclohexyl]-dimethylamine (non-polar diastereomer);
2-[[4-(dimethylamino)-1,4-diphenyl-cyclohexyl]-methyl-amino]-ethanol (non-polar diastereomer);
[4-[[4,6-bis(dimethylamino)-[1,3,5]triazin-2-yl]-methyl-amino]-1,4-diphenyl-cyclohexyl]-dimethylamine (non-polar diastereomer);
dimethyl-[4-[methyl-(4-methylamino-6-piperidin-1-yl-[1,3,5]triazin-2-yl)-amino]-1,4-diphenyl-cyclohexyl]-amine (polar diastereomer);
4-[[4-(dimethylamino)-1,4-diphenyl-cyclohexyl]-methyl-amino]-butan-1-ol (polar diastereomer);
3-[[4-(dimethylamino)-1,4-diphenyl-cyclohexyl]-methyl-carbamoyl]-propionic acid (polar diastereomer);
[4-(5-fluoro-3-methyl-1H-indol-2-yl)-1-phenyl-4-pyrrolidin-1-yl-cyclohexyl]-dimethylamine (polar diastereomer);
[1-(3-fluorophenyl)-4-(3-methyl-1H-indol-2-yl)-4-piperidin-1-yl-cyclohexyl]-dimethylamine (non-polar diastereomer);
[4-(acetidin-1-yl)-4-(5-fluoro-3-methyl-1H-indol-2-yl)-1-(3-fluorophenyl)-cyclohexyl]-dimethylamine (non-polar diastereomer);
[4-(acetidin-1-yl)-4-(5-fluoro-3-methyl-1H-indol-2-yl)-1-(3-fluorophenyl)-cyclohexyl]-dimethylamine (polar diastereomer);
[4-(5-fluoro-3-methyl-1H-indol-2-yl)-4-morpholin-4-yl-1-phenyl-cyclohexyl]-dimethylamine (polar diastereomer);
[4-(5-fluoro-3-methyl-1H-indol-2-yl)-4-methylamino-1-phenyl-cyclohexyl]-dimethylamine (non-polar diastereomer);
[4-(5-fluoro-3-methyl-1H-indol-2-yl)-4-methylamino-1-phenyl-cyclohexyl]-dimethylamine (polar diastereomer);
dimethyl-[4-methylamino-4-(3-methyl-1H-indol-2-yl)-1-thiophen-2-yl-cyclohexyl]-amine (polar diastereomer);
[4-(5-fluoro-3-methyl-1H-indol-2-yl)-4-morpholin-4-yl-1-phenyl-cyclohexyl]-dimethylamine (non-polar diastereomer);
[4-[(4-amino-6-methylamino-[1,3,5]triazin-2-yl)-methyl-amino]-1,4-diphenyl-cyclohexyl]-dimethylamine (non-polar diastereomer);
[4-[[4-(isopropyl-methyl-amino)-6-methylamino-[1,3,5]triazin-2-yl]-methyl-amino]-1,4-diphenyl-cyclohexyl]-dimethylamine (polar diastereomer);
[4-[(4-amino-6-methylamino-[1,3,5]triazin-2-yl)-methyl-amino]-1,4-diphenyl-cyclohexyl]-dimethylamine (polar diastereomer);
[4-[[4-(benzylamino)-6-methylamino-[1,3,5]triazin-2-yl]-methyl-amino]-1,4-diphenyl-cyclohexyl]-dimethylamine (polar diastereomer);
[4-[(4-butylamino-6-methylamino-[1,3,5]triazin-2-yl)-methyl-amino]-1,4-diphenyl-cyclohexyl]-dimethylamine (polar diastereomer);
[4-[[4-(4-methoxy-phenoxy)-[1,3,5]triazin-2-yl]-methyl-amino]-1,4-diphenyl-cyclohexyl]-dimethylamine (polar diastereomer);
(1,4-diphenyl-4-pyrrolidin-1-yl-cyclohexyl)-methylamine (polar diastereomer);
(1,4-diphenyl-4-pyrrolidin-1-yl-cyclohexyl)-methylamine (non-polar diastereomer);
[4-[(benzyl-methyl-amino)-methyl]-1,4-diphenyl-cyclohexyl]-dimethylamine;
[4-dimethylamino-1-(3-methyl-1H-indol-2-yl)-4-thiophen-2-yl-cyclohexyl]-methylamine (non-polar diastereomer);
(1,4-diphenyl-4-pyrrolidin-1-yl-cyclohexyl)-dimethylamine (polar diastereomer);
(1,4-diphenyl-4-pyrrolidin-1-yl-cyclohexyl)-dimethylamine (non-polar diastereomer);
[4-[[4-(benzylamino)-[1,3,5]triazin-2-yl]-methyl-amino]-1,4-diphenyl-cyclohexyl]-dimethylamine (polar diastereomer);
dimethyl-[4-[methyl-(4-piperidin-1-yl-[1,3,5]triazin-2-yl)-amino]-1,4-diphenyl-cyclohexyl]-amine (polar diastereomer);
[4-[(4-butylamino-[1,3,5]triazin-2-yl)-methyl-amino]-1,4-diphenyl-cyclohexyl]-dimethylamine (polar diastereomer);
[4-[(4-amino-[1,3,5]triazin-2-yl)-methyl-amino]-1,4-diphenyl-cyclohexyl]-dimethylamine (polar diastereomer);
[4-[[4-(isopropyl-methyl-amino)-[1,3,5]triazin-2-yl]-methyl-amino]-1,4-diphenyl-cyclohexyl]-dimethylamine (polar diastereomer);
[4-[[4-(tert-butylamino)-[1,3,5]triazin-2-yl]-methyl-amino]-1,4-diphenyl-cyclohexyl]-dimethylamine (polar diastereomer);
[4-(cyclohexyl-methylamino)-1-(3-fluorophenyl)-4-(3-methyl-1H-indol-2-yl)-cyclohexyl]-dimethylamine (non-polar diastereomer);
[4-(cyclopentylamino)-1-(3-fluorophenyl)-4-(3-methyl-1H-indol-2-yl)-cyclohexyl]-dimethylamine (non-polar diastereomer);
[4-amino-1-(3-fluorophenyl)-4-(3-methyl-1H-indol-2-yl)-cyclohexyl]-dimethylamine;
[1-(3-fluorophenyl)-4-(3-methyl-1H-indol-2-yl)-4-(pyridin-4-ylamino)-cyclohexyl]-dimethylamine;
[4-[(butyl-methyl-amino)-methyl]-1,4-diphenyl-cyclohexyl]-dimethylamine (non-polar diastereomer);
[4-[(butyl-methyl-amino)-methyl]-1,4-diphenyl-cyclohexyl]-dimethylamine (polar diastereomer);
N-(4-dimethylamino-1,4-diphenyl-cyclohexyl)-N-methyl-cyclohexane carboxylic acid amide (polar diastereomer);
N-(4-dimethylamino-1,4-diphenyl-cyclohexyl)-N-methyl-tetrahydro-pyran-4-carboxylic acid amide (polar diastereomer);
cyclohexyl-methyl-(4-dimethylamino-1,4-diphenyl-cyclohexyl)-methylamine (polar diastereomer);
(4-dimethylamino-1,4-diphenyl-cyclohexyl)-methyl-(tetrahydro-pyran-4-yl-methyl)-amine (polar diastereomer);
N-(4-dimethylamino-1,4-diphenyl-cyclohexyl)-N,1-dimethyl-piperidin-4-carboxylic acid amide (polar diastereomer);
(4-dimethylamino-1,4-diphenyl-cyclohexyl)-methyl-[(1-methyl-piperidin-4-yl)-methyl]-amine (polar diastereomer);
and physiologically compatible salts and/or solvates thereof.

The compounds according to the invention act, for example, on the relevant ORL 1-receptor in association with different diseases, and therefore they are suitable as pharmaceutical active substance in a medication.

Therefore, the invention additionally relates to medications, which contain at least one compound according to the invention, as well as possibly suitable additives and/or adjuvants and/or possibly further active substances.

The compounds according to the invention have an affinity to the µ-opioid or to the ORL 1-receptor comparable to the compounds disclosed as exemplary compounds in WO 03/008370. However, compared to these compounds they exhibit a higher selectivity with respect to the kappa-opioid receptor, which is responsible for side-effects such as e.g. dysphoria, sedation and diuresis. In addition, with a favourable ORL 1/µ affinity the compounds according to the invention exhibit a balanced affinity to the µ-opioid receptor that is not too strong. This is an advantage, since the µ-opioid receptor is associated with side-effects, in particular respiratory depression, constipation and addiction dependence. Therefore, they are particularly suitable for drug development.

Besides at least one compound according to the invention, the medications according to the invention possibly contain suitable additives and/or adjuvants, hence also support materials, fillers, solvents, dilutants, colouring agents and/or binders, and can be administered as liquid medications in the form of injectable solutions, drops or juices, as semisolid medications in the form of granules, tablets, pellets, patches, capsules, plasters/spray plasters or aerosols. The selection of adjuvants etc. as well as the quantities thereof to be used are dependent on whether the medication is to be applied orally, perorally, parenterally, intravenously, intraperitoneally, intradermally, intramuscularly, intranasally, bucally, rectally or locally, e.g. onto the skin, mucous membranes or into the eyes. Preparations in the form of tablets, coated tablets, capsules, granules, drops, juices and syrups are suitable for oral application, solutions, suspensions, readily reconstituted dry preparations as well as sprays are suitable for parenteral, topical and inhalatory application. Compounds according to the invention in a depot, in dissolved form or in a plaster, possibly with the addition of skin-penetration promoters, are suitable preparations for percutaneous application. Preparation forms that may be applied orally or percutaneously can release the compounds according to the invention in a delayed manner. The compounds according to the invention can also be applied in parenteral long-term depot forms such as e.g. implants or implanted pumps. In principle, other additional active substances known to the skilled person can be added to the medications according to the invention.

The amount of active substance to be administered to the patient varies depending on the weight of the patient, on the type of application, the indication and the degree of severity of the disease. Usually, 0.00005 to 50 mg/kg, preferably 0.001 to 0.5 mg/kg, of at least one compound according to the invention are applied.

For all the above-mentioned forms of the medication according to the invention it is particularly preferred if, besides at least one compound according to the invention, the medication also contains a further active substance, in particular an opioid, preferably a strong opioid, in particular morphine, or an anaesthetic, preferably hexobarbital or halothane.

In a preferred form of the medication, a contained compound according to the invention is present in the form of pure diastereomer and/or enantiomer.

The ORL 1-receptor was identified in particular in the pain process. Compounds according to the invention can be used accordingly for the production of a medication for the treatment of pain, in particular of acute, neuropathic or chronic pain.

Therefore, the invention additionally relates to the use of a compound according to the invention for the production of a medication for the treatment of pain, in particular of acute, visceral, neuropathic or chronic pain.

The invention further relates to the use of a compound according to the invention for the treatment of anxiety conditions, stress and stress-related syndromes, depressive illnesses, epilepsy, Alzheimer's disease, senile dementia, general cognitive dysfunctions, learning and memory disabilities (as nootropic), withdrawal symptoms, alcohol and/or drug and/or medication misuse and/or dependence, sexual dysfunctions, cardiovascular diseases, hypotension, hypertension, tinitus, pruritus, migraine, hearing impairment, deficient intestinal motility, eating disorders, anorexia, bulimia, mobility disorders, diarrhoea, cachexia, urinary incontinence, or as muscle relaxant, anticonvulsive or anaesthetic, or for coadministration in the treatment with an opioid analgesic or with an anaesthetic, for diuresis or anti-natriuresis, anxiolysis, for modulating movement activity, for modulating neurotransmitter release and for treating neurodegenerative diseases associated therewith, for treating withdrawal symptoms and/or for reducing the addiction potential of opioids.

In this case, it can be preferred in one of the above uses if a used compound is present as a pure diastereomer and/or enantiomer, as a racemate or as non-equimolar or equimolar mixture of the diastereomers and/or enantiomers.

The invention additionally relates to a method for treating, in particular in one of the aforementioned indications, a non-human mammal or human, which or who requires a treatment for pain, in particular chronic pain, by the administration of a therapeutically effective dose of a compound according to the invention or a medication according to the invention.

The invention further relates to a method for producing the compounds according to the invention as outlined in the following description and examples.

a) Synthesis of cyclohexane-1,4-diamines

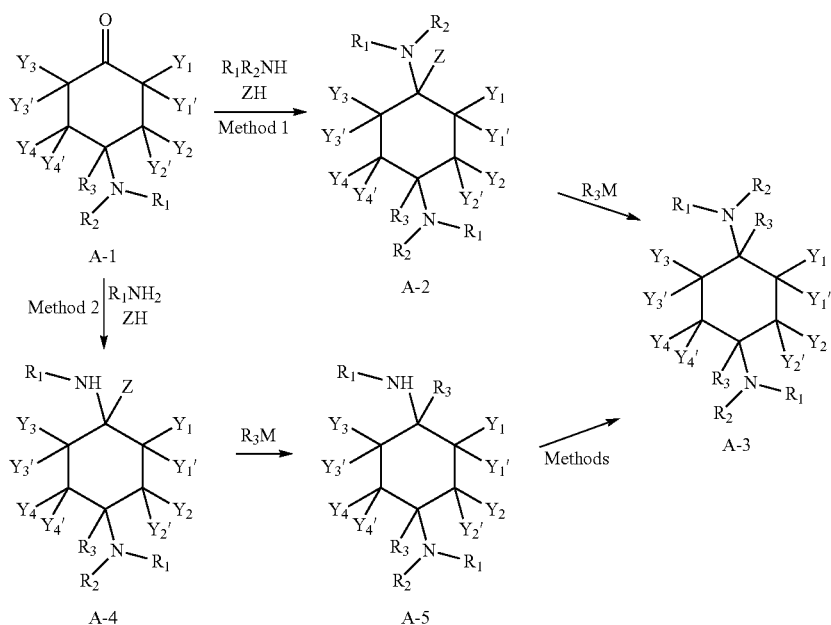

Method 1:

Structures of formula A-2 can be produced by the reaction of A-1 ketones with amines and Z—H acid reactants. Suitable Z—H reactants are e.g. hydrogen cyanide, 1,2,3-triazole, benzotriazole or pyrazole.

A particularly preferred path to compounds of structure A-2 is the conversion of ketones with metal cyanides and the corresponding amine in the presence of acid, preferably in an alcohol, at temperatures of −40 to 60° C., preferably at room temperature with alkali metal cyanides in methanol.

A further particularly preferred path to compounds of structure A-2 is the conversion of ketones with 1,2,3-triazole and the corresponding amine in the presence of ? under dehydrating conditions, preferably using a water separator at elevated temperature in an inert solvent or using a molecular sieve or another dehydrating agent. Similarly, structures similar to A-2 can be introduced with benzotriazole or pyrazole groups instead of triazole groups. In general, A-3 cyclohexane-1,4-diamines can also be obtained by substituting suitable Z leaving groups in structures of formula A-2. Suitable leaving groups are preferably cyano groups; 1,2,3-triazol-1-yl groups. Further suitable leaving groups are 1H-benzo[d][1,2,3]triazol-1-yl groups and pyrazol-1-yl groups (Katritzky et al., Synthesis 1989, 66-69).

A particularly preferred path to compounds of structure A-3 is the conversion of A-2 aminonitriles with corresponding organometallic compounds, preferably Grignard compounds, preferably in ethers, preferably at RT. The organometallic compounds are either commercially available or can be produced using known methods. A further particularly preferred path to compounds of structure A-3 is the conversion of A-2 aminotriazoles with corresponding organometallic compounds, preferably Grignard compounds, preferably in ethers, preferably at RT.

The organometallic compounds are either commercially available or can be produced using methods known in specialist literature.

Method 2:

Structures of formula A-4 can be produced by reacting A-1 ketones with primary amines and Z—H acid reactants. Suitable Z—H reactants are e.g. hydrogen cyanide, 1,2,3-triazole, benzotriazole or pyrazole.

A particularly preferred path to compounds of structure A-4 is the conversion of ketones with metal cyanides and the corresponding amine in the presence of acid, preferably in an alcohol, at temperatures of −40 to 60° C., preferably at room temperature with alkali metal cyanides in methanol.

A further particularly preferred path to compounds of structure A-4 is the conversion of ketones with 1,2,3-triazole and the corresponding amine in the presence of ? under dehydrating conditions, preferably using a water separator at elevated temperature in an inert solvent or using a molecular sieve or another dehydrating agent. Similarly, structures similar to A-4 can be introduced with benzotriazole or pyrazole groups instead of triazole groups.

In general, A-5 cyclohexane-1,4-diamines can also be obtained by substituting suitable Z leaving groups in structures of formula A-4. Suitable leaving groups are preferably cyano groups; 1,2,3-triazol-1-yl groups. Further suitable leaving groups are 1H-benzo[d][1,2,3]triazol-1-yl groups and pyrazol-1-yl groups (Katritzky et al., Synthesis 1989, 66-69).

A particularly preferred path to compounds of structure A-5 is the conversion of A-4 aminonitriles with corresponding organometallic compounds, preferably Grignard compounds, preferably in ethers, preferably at RT. The organometallic compounds are either commercially available or can be produced using known methods. A further particularly preferred path to compounds of structure A-5 is the conversion of A-4 aminotriazoles with corresponding organometallic compounds, preferably Grignard compounds, preferably in ethers, preferably at RT.

The organometallic compounds are either commercially available or can be produced using methods known in specialist literature.

Cyclohexane-1,4-diamines of type A-3 can also be synthesised using methods known to the person skilled in the art. An introduction of (alkyl) substituents can then occur under conditions of a reductive amination by means of an aldehyde component. Such a method known to the skilled person can be the conversion with an aldehyde with the addition of a reducing agent, e.g. sodium boron hydride.

b) Synthesis of (1,4-diaminocyclohexyl)(heteroaryl)methanones

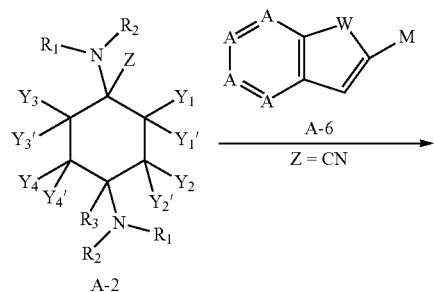

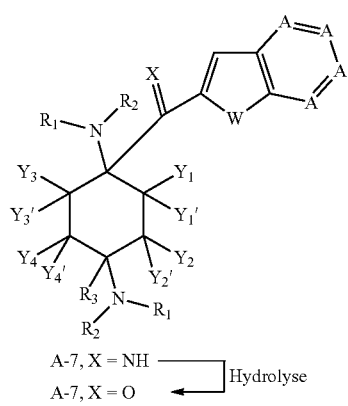

Substituted (1,4-diaminocyclohexyl)(heteroaryl)methanones of type A-7, X=O can be synthesised from the above-described A-2 educt, Z=CN, using methods known to the person skilled in the art. By converting metallised heterocycles of type A-6 with the triple bond of A-2, Z=CN, the intermediate A-7, X=NH is obtained. A hydrolysis under acid conditions then results by splitting imine A-7, X=O.

c) Synthesis of 4-alkoxycyclohexane-1-amines

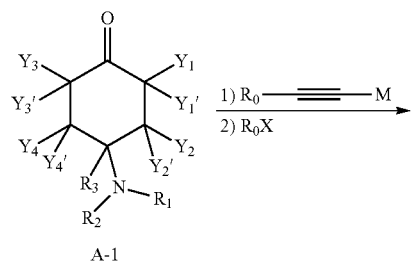

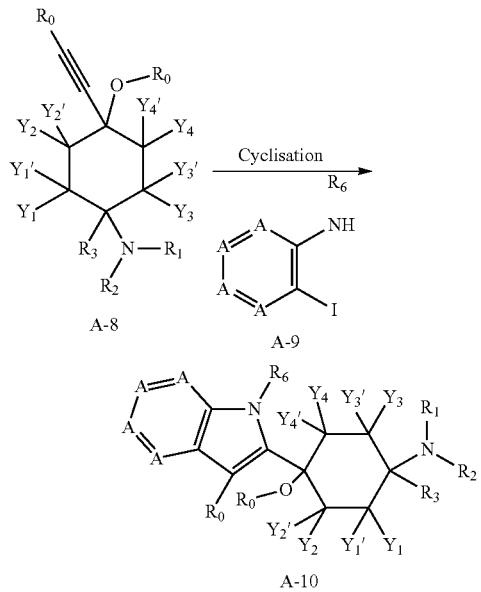

Substituted 4-alkoxycyclohexane-1-amines of type A-10 can be synthesised from the A-1 educt using methods known to the person skilled in the art. The alcoholate obtained by the reaction of metallised alkines with A-1 is converted to A-8 with the corresponding electrophiles e.g. of type $R_0X$ (with X=e.g. Br, I, OTos, OTf etc.). The conversion of A-9 carbinols to the substituted 4-alkoxycyclohexane-1-amines of type A-10 according to the invention can occur in organic solvents, e.g. tetrahydrofuran, dimethylformamide, benzol, toluol, xylols, dimethoxyethane or diethylene glycol dimethyl ether, in the presence of an inorganic base, e.g. sodium, potassium or caesium carbonate or potassium phosphate in the presence of $PdCl_2$, $Pd(OAc)_2$, $PdCl_2(MeCN)_2$, $PdCl_2(PPh_3)_2$ or [1,3-bis-(2,6-diisopropylphenyl)imidazol-2-ylidene]-(3-chloropyridyl)palladium(II)-chloride (PEPPSI®), possibly in the presence of additional ligands, e.g. triphenyl-, tri-o-tolyl-, tricyclohexyl or tri-t-butyl phosphine, possibly in the presence of phase transfer catalysts, e.g. tetra-n-butyl ammonium chloride, tetra-n-butyl ammonium hydroxide or tetra-n-butyl ammonium iodide, and at temperatures between 60° C. and 180° C., also microwave-assisted.

d) Synthesis of 4-aminomethyl-cyclohexyl-1-amines

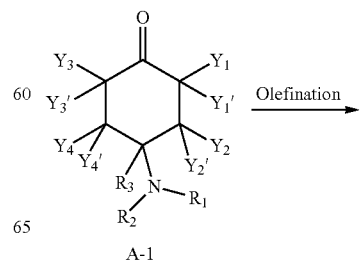

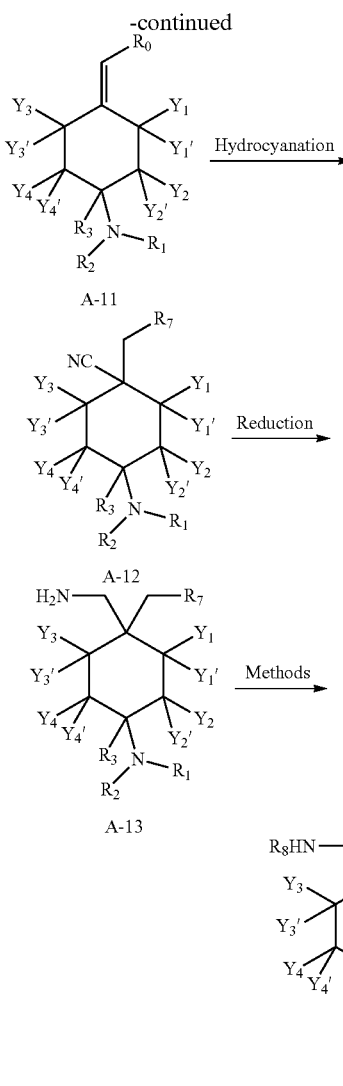

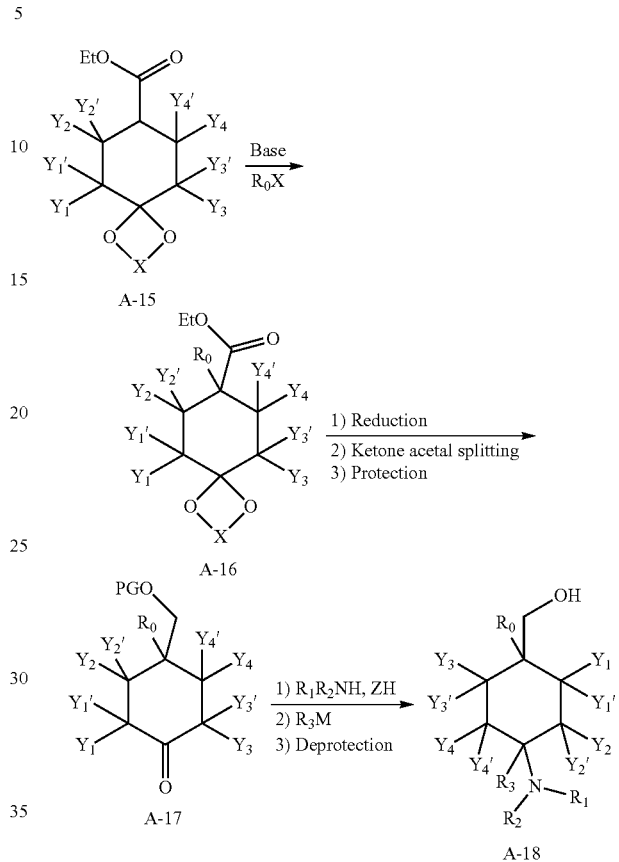

d) Synthesis of (4-aminocyclohexyl)methanols

Substituted 4-aminomethyl-cyclohexyl-1-amines of type A-14 can be synthesised from the known A-1 educts by methods known to the person skilled in the art. Working from ketones such as A-1, the intermediate A-11 alkenes are obtained by a Wittig olefination with phosphorus ylides. Compounds of formula A-12 can then be obtained from the corresponding A-11 precursors in the presence of a cobalt (II)-salen complex by hydrocyanation (Carreira et al. Angew. Chem. Int. Ed., 46, 2006, 4519). A conversion of the nitrile group in A-12 with a reducing agent, e.g. a hydride such as sodium or lithium boron hydride, sodium cyanoboron hydride, sodium triacetoxyboron hydride, diisobutyl aluminium hydride, lithium-tri-(sec-butyl)boron hydride (L-Selectride®) or lithium aluminium hydride, possibly in the presence of Lewis acids, e.g. $ZnCl_2$, $Ni(OAc)_2$ or $CoCl_2$, gives the A-13 amines.

Method 1:

Amines of type A-13 can be acylated, sulphonylated or carbamoylated to compounds of A-14 using methods known to the person skilled in the art. Such a method known to the skilled person can be the conversion with an anhydride or an acid chloride with the addition of a base, e.g. triethylamine.

Method 2:

Amines of type A-13 can be reductively aminated to compounds of A-14 using methods known to the person skilled in the art. Such a method known to the skilled person can be the conversion with an aldehyde with the addition of a reducing agent, e.g. sodium boron hydride.

Substituted (4-aminocyclohexyl)methanols of type A-18 can be synthesised from the known A-15 educts by methods known to the person skilled in the art. The deprotonation of A-15 esters with a base, e.g. lithium diisopropylamide (LDA), and conversion with the corresponding electrophiles, e.g. of type $R_0$—X (with X=e.g. Br, I, OTos, OTf etc.), to A-16 is described in the specialist literature (Williams et al. J. Org. Chem. 1980, 45, 5082; Shiner et al. J. Am. Chem. Soc. 1981, 103, 436; Xia et al. Org. Lett. 2005, 7, 1315.). A conversion of A-16 can occur with a reducing agent, e.g. a hydride such as sodium or lithium boron hydride, sodium cyanoboron hydride, sodium triacetoxyboron hydride, diisobutyl aluminium hydride, lithium-tri-(sec-butyl)boron hydride (L-Selectride®) or lithium aluminium hydride, possibly in the presence of Lewis acids, e.g. $ZnCl_2$, $Ni(OAc)_2$ or $CoCl_2$, and ketone acetal splitting using methods known to the skilled person by deprotection by means of acids. In this case, X is selected from the group alkyl, alkyl/alkylidene/alkylidene substituted with aryl or alkyl (saturated/unsaturated). A protection of the hydroxyl group according to methods known to the skilled person, e.g. by conversion with alkyl vinyl ethers, leads to the corresponding A-17 α-alkyloxy ethyl ethers.

Structures of formula A-18 can be produced by reaction of A-17 ketones with amines and Z—H acid reactants. Suitable Z—H reactants are e.g. hydrogen cyanide, 1,2,3-triazole, benzotriazole or pyrazole.

A particularly preferred path to such aminonitriles is the conversion of ketones with metal cyanides and the corresponding amine in the presence of acid, preferably in an alcohol, at temperatures of −40 to 60° C., preferably at room temperature with alkali metal cyanides in methanol.

A further particularly preferred path to such aminonitriles is the conversion of ketones with 1,2,3-triazole and the corresponding amine in the presence of ? under dehydrating conditions, preferably using a water separator at elevated temperature in an inert solvent or using a molecular sieve or another dehydrating agent. Similarly, similar structures can be introduced with benzotriazole or pyrazole groups instead of triazole groups.

The introduction of the residue $R_3$ can occur by substitution of suitable Z leaving groups such as has already been described for the conversion of A-2 to A-3, for example.

Compounds of formula A-18 can be released from corresponding acetals or from their salts by deprotection by means of acids using methods known to the skilled person. In this case, PG is selected from the group of acetal protective groups for hydroxyl groups known to the skilled person, e.g. an α-alkyloxy ethyl ether protective group.

e) Synthesis of 4-indolyl cyclohexane-1,4-diamines
Method 1:

preferably organo-lithium and Grignard compounds, preferably in ethers, preferably at RT. The organometallic compounds are either commercially available or can be produced using known methods.

Step 3:

A-20 alkine derivatives can be converted into the protected A-21 indole derivatives according to F. Messina et al./Tetrahedron: Asymmetry 11 (2000) 1681-1685.

Step 4:

A-21 indole derivatives can be converted to A-22 indole derivatives using methods known from specialist literature (cf. Protective Groups in Organic Synthesis by Peter G. M. Wuts, Theodora W. Greene, Wiley Blackwell; 4th Edition).

Step 5:

A-22 indole derivatives can be converted into A-23 amides using methods known to the skilled person. Such a method known to the skilled person can be, for example, the conversion of A-22 with a carboxylic acid by adding a coupling reagent, e.g. carbonyl di-imidazole.

A-22 indole derivatives can be converted into A-23 sulphonamides using methods known to the skilled person.

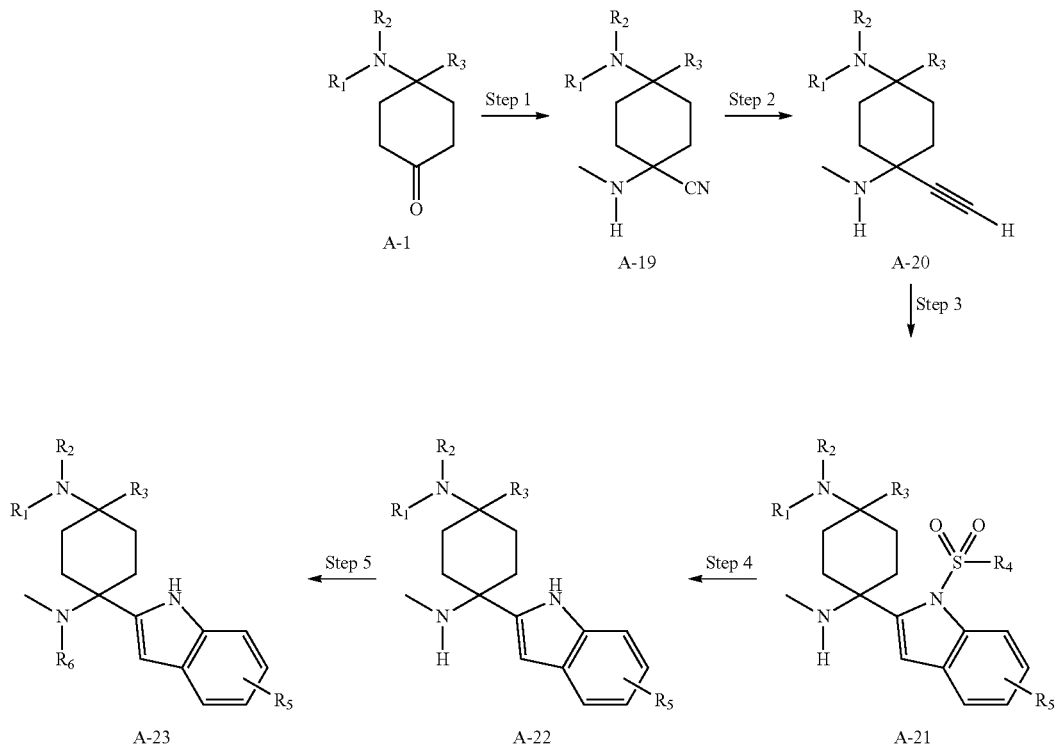

Step 1:

The keto group can be converted into monomethyl aminonitrile using methods known from the specialist literature, in particular applying the literature texts relevant to the synthesis of A-1.

Step 2:

A-19 aminonitriles can be converted into A-20 alkine derivatives with corresponding organometallic compounds, Such a method known to the skilled person can be, for example, the conversion of A-22 with a sulphonyl chloride by adding a base, e.g. triethylamine.

A-22 indole derivatives can be converted into A-23 amines using methods known to the skilled person. Such a method known to the skilled person can be, for example, the conversion of A-22 with an aldehyde by adding a reducing reagent, e.g. sodium boron hydride.

Method 2:

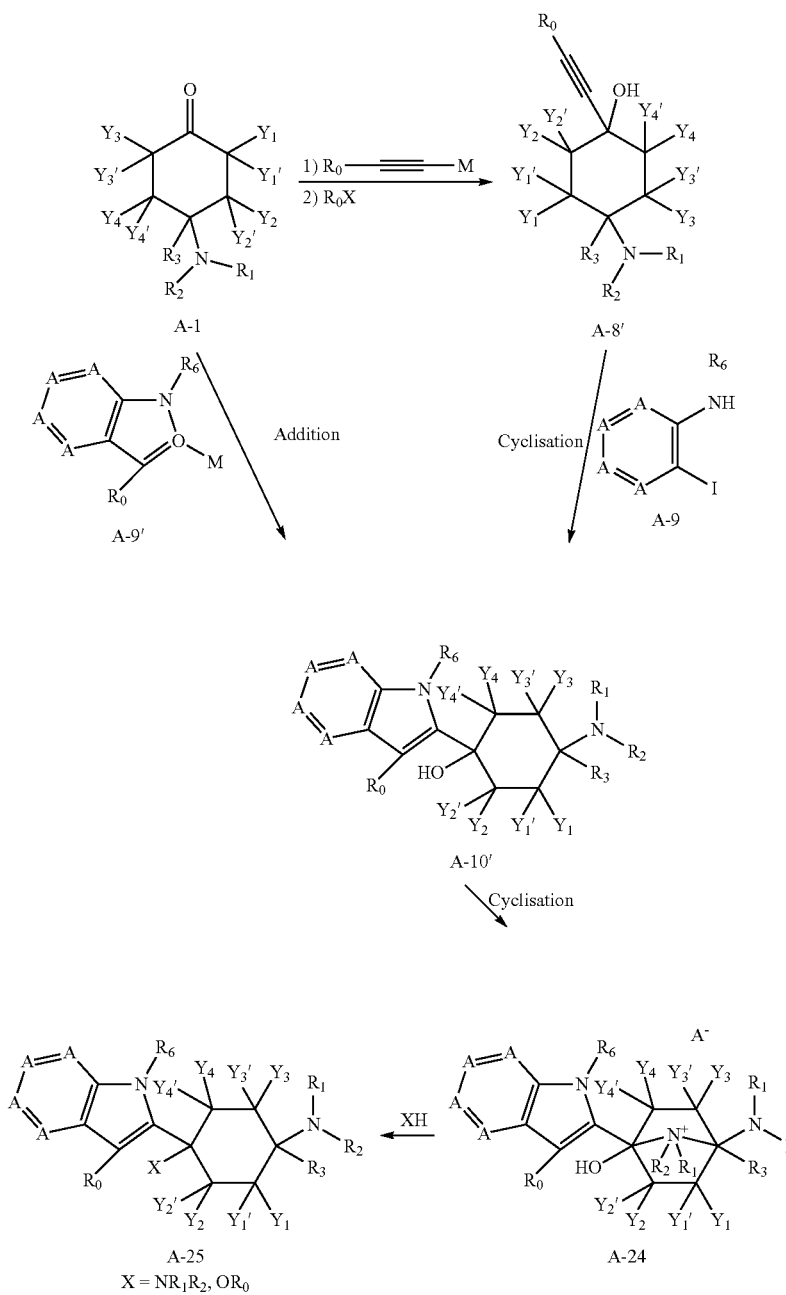

Substituted cyclohexanamines of type A-25 can be synthesised from the A-1 educt by reaction with metallised alkines. The conversion of the A-8' and A-9 carbinols to substituted 4-alkoxycyclohexane-1-amines of type A-10' can occur in organic solvents, e.g. tetrahydrofuran, dimethylformamide, benzol, toluol, xylols, dimethoxyethane or diethylene glycol dimethyl ether, in the presence of an inorganic base, e.g. sodium, potassium or caesium carbonate or potassium phosphate in the presence of $PdCl_2$, $Pd(OAc)_2$, $PdCl_2(MeCN)_2$, $PdCl_2(PPh_3)_2$ or [1,3-bis-(2,6-diisopropylphenyl)imidazol-2-ylidene]-(3-chloropyridyl)palladium(II)-chloride (PEPPSI®), possibly in the presence of additional ligands, e.g. triphenyl-, tri-o-tolyl-, tricyclohexyl or tri-t-butyl phosphine, possibly in the presence of phase transfer catalysts, e.g. tetra-n-butyl ammonium chloride, tetra-n-butyl ammonium hydroxide or tetra-n-butyl ammonium iodide, and at temperatures between 60° C. and 180° C., also microwave-assisted. Alternatively, a conversion of A-9' metallised heterocycles with A-1 educt in organic solvents at temperatures between 24° C. and −100° C. can also lead to carbinols of type A-10'. The subsequent cyclisation of A-10' to the A-24 ammonium salt can occur in organic solvents in the presence of fluorinating agents at temperatures between 25° C. and −100° C. The opening up of the A-24 salt to the substituted cyclohexanamines of type A-25 according to the invention can occur with suitable nucleophiles without or also in the presence of organic solvents at temperatures between 0° C. and 180° C., also microwave-assisted.

f) Synthesis of N-heteroaryl-1,4-diamines

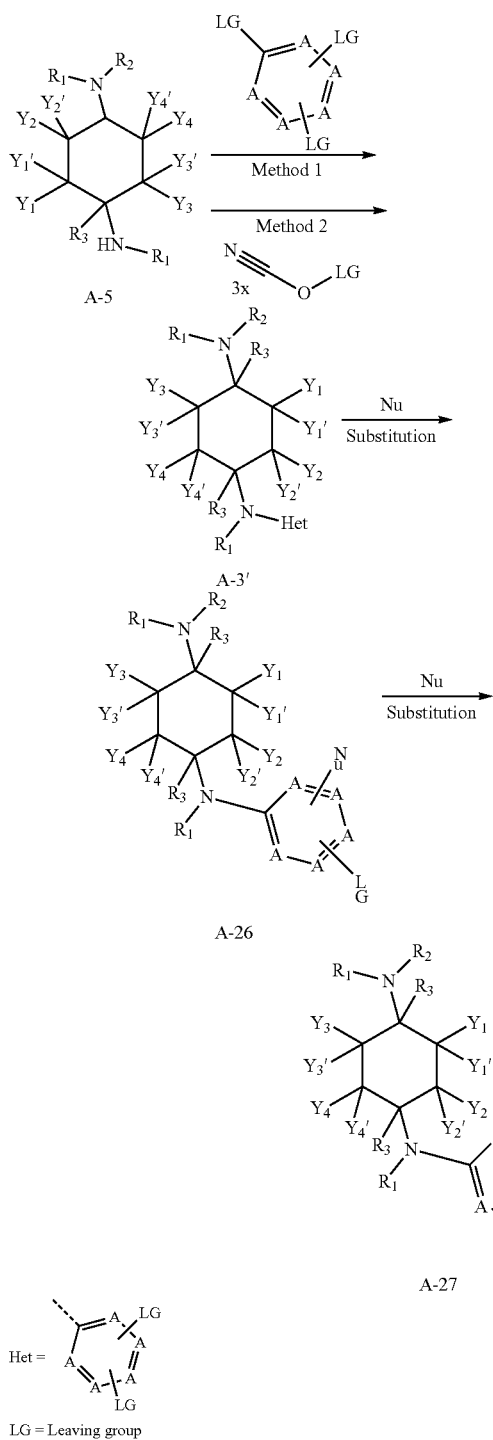

LG = Leaving group

Substituted cyclohexanamines of type A-26 and A-27 can be synthesised from the A-5 educt. The A-3' intermediate is obtained by the reaction of heterocycles (method 1) or cyanates (method 2) with suitable leaving groups (e.g. with LG=Cl or 4-OMe-$C_6H_4$). The remaining leaving groups can be successively replaced by suitable nucleophiles (Nu) and the substituted cyclohexanamines of type A-26 and A-27 according to the invention are obtained.

g) Preliminary Steps

Compounds of the general formulae A-1 and A-15 are either commercially available or their production is known from the prior art or can be derived from the prior art in an obvious manner for the skilled person. Particularly relevant in this case are the following citations: Jirkovsky et al., J. Heterocycl. Chem., 12, 1975, 937-940; Beck et al., J. Chem. Soc. Perkin 1, 1992, 813-822; Shinada et al., Tetrahedron Lett., 39, 1996, 7099-7102; Garden et al., Tetrahedron, 58, 2002, 8399-8412; Lednicer et al., J. Med. Chem., 23, 1980, 424-430; Bandini et al. J. Org. Chem. 67, 15; 2002, 5386-5389; Davis et al., J. Med. Chem. 35, 1, 1992, 177-184; Yamagishi et al., J. Med. Chem. 35, 11, 1992, 2085-2094; Gleave et al.; Bioorg. Med. Chem. Lett. 8, 10, 1998, 1231-1236; Sandmeyer, Helv. Chim. Acta; 2; 1919; 239; Katz et al.; J. Med. Chem. 31, 6, 1988; 1244-1250; Bac et al. Tetrahedron Lett. 1988, 29, 2819; Ma et al. J. Org. Chem. 2001, 66, 4525; Kato et al. J. Fluorine Chem. 99, 1, 1999, 5-8.

With respect to further details on the synthesis of the compounds according to the invention, reference is additionally made to the following in their full scope: WO2002/090317, WO2002/90330, WO2003/008370, WO2003/008731, WO2003/080557, WO2004/043899, WO2004/043900, WO2004/043902, WO2004/043909, WO2004/043949, WO2004/043967, WO2005/063769, WO2005/066183, WO2005/110970, WO2005/110971, WO2005/110973, WO2005/110974, WO2005/110975, WO2005/110976, WO2005/110977, WO2006/018184, WO2006/108565, WO2007/079927, WO2007/079928, WO2007/079930, WO2007/079931, WO2007/124903, WO2008/009415 and WO2008/009416.

EXAMPLES

The following examples serve to explain the invention in more detail, while not restricting it.

The yields of the compounds produced are not optimised. All temperatures are uncorrected. The term "ether" means diethyl ether, "EE" ethyl acetate and "DCM" dichloromethane. The term "equivalents" means substance amount equivalents, "mp" melting point or melting range, "decomp." decomposition, "RT" room temperature, "abs." absolute (free from water), "rac." racemic, "conc." concentrated, "min" minutes, "h" hours, "d" days, "% vol." percent by volume, "% m" percent by mass and "M" is a concentration detail in mol/l.

Silica gel 60 (0.040-0.063 mm) from E. Merck, Darmstadt was used as the stationary phase for the column chromatography. The thin-film chromatography tests were conducted with silica gel 60 F 254 HPTLC chromatoplates from E. Merck, Darmstadt. The mixture ratios of mobile solvents for chromatography tests are always given in volume/volume.

Example 1

1-(imino(1-methyl-1H-indol-2-yl)methyl)-N1,N1,N4,N4-tetramethyl-4-phenylcyclohexane-1,4-diamine bis(2-hydroxypropane-1,2,3-tricarboxylate)

a) 1,4-bis-dimethylamino-4-phenylcyclohexane carbonitrile

A mixture of methanol (50 ml) and water (50 ml) was acidified with hydrochloric acid (37%, 0.2 ml) and mixed with an aqueous solution of dimethylamine (40%, 11.5 ml, 91 mmol) with ice cooling and stirring. Then 4-dimethylamino-4-phenylcyclohexanone (2.17 g, 10 mmol) and KCN (1.6 g, 24.6 mmol) were added to the solution. A clear solution was formed after 15 min. The ice cooling was removed and the batch stirred for 2.5 h at RT, and a white solid began to separate out after approx. 1 h. The batch was brought to approx. 0° C. again for 1 h by means of ice cooling to complete the precipitation. The precipitate was then separated by means of a fritted glass filter and dried in a vacuum at a bath temperature of 40° C. A diastereoisomer mixture of the title compound was obtained with a yield of 1.83 g (67%) and a melting point of 82-92° C.

13C NMR (101 MHz, CDCl3) δ ppm: 29.3*, 30.2, 31.2, 37.7, 38.2, 39.9, 58.4*, 60.2, 62.4*, 118.7, 119.0, 126.8, 127.4, 127.7, 128.0, 136.2*, 137.7*

* spread signals b) 1-[imino-(1-methyl-1H-indol-2-yl)methyl]-N,N,N',N'-tetramethyl-4-phenyl-cyclohexane-1,4-diamine [More Non-polar Diastereoisomer and more Polar Diastereoisomer]

N-methyl indole [1.31 g, 10 mmol dissolved in dry THF (10 ml)] was added to a solution of n-butyl lithium (2.5N in n-hexane, 4 ml, 10 mmol) in dry THF (10 ml) with the exclusion of moisture at 0° C. The batch was stirred for 60 min while maintaining the cooling, and a solid began to precipitate out after approx. 10 min. The addition of the diastereoisomer mixture from the previous step [1.33 g, 5 mmol, dissolved in dry THF (10 ml)] then occurred within 10 min. After the addition had ended the cooling was removed and the batch stirred a further 18 h after RT was reached. For work up the batch was carefully mixed with a mixture of THF (5 ml) and water (1 ml). Then, saturated NaCl solution (30 ml) was added to the mixture. The organic phase was separated, the aqueous phase was extracted with ethyl acetate (4×20 ml). The combined organic extracts were dried over MgSO4 and then concentrated to low volume. The residue obtained (2.7 g) was purified by chromatography [silica gel 60 G (10 g); ethyl acetate (100 ml), ethyl acetate/ethanol 1:1 (100 ml), EtOH 50 ml]. The more non-polar diastereoisomer was thus obtained with a yield of 26% (526 mg) and the more polar diastereoisomer with a yield of 32% (650 mg).

c) 1-(imino(1-methyl-1H-indol-2-yl)methyl)-N1,N1,N4,N4-tetramethyl-4-phenylcyclohexane-1,4-diamine bis(2-hydroxypropane-1,2,3-tricarboxylate)

The more non-polar diastereoisomer (230 mg, 0.61 mmol) was dissolved in propan-2-ol (5 ml) in the boiling heat and mixed with a hot solution of citric acid [382 mg, 2 mmol, in propan-2-ol (4 ml)]. A precipitate was separated out when the solution cooled to RT. The batch was left for 20 h at 5° C. to complete the precipitation, then the solid was separated by means of a fritted glass filter and dried. The bis-citrate was thus obtained as a vitreous solid with a yield of 310 mg (64%).

13C NMR (101 MHz, DMSO-D6) δ ppm: 25.5 (propan-2-ol), 26.9, 27.4, 30.9, 37.5, 38.1, 43.3, 62.0 (propan-2-ol), 62.7, 66.1*, 71.9, 101.3*, 110.1, 119.7, 120.7, 122.1, 126.3, 128.6, 128.8, 132.1*, 137.0, 137.3, 171.2, 173.5, 175.5

* widely spread signals

Example 2

(4-dimethylamino-4-phenyl-1-(pyrrolidin-1-yl)cyclohexyl)-(1-methyl-1H-indol-2-yl)methanone (More Non-polar Diastereoisomer)

During the synthesis of the exemplary compound 6, step b) the analogous non-polar compound was also formed as a mixture, this (680 mg) was mixed with 2N HCl (20 ml) and stirred for 18 h at RT. A solid separated out. For work up the reaction mixture was basified with 2N NaOH (30 ml) at room temperature. The aqueous phase was extracted with ethyl acetate (3×10 ml). The combined organic extracts were dried over MgSO4 and then concentrated to low volume. Attempts to recrystallise the raw product formed (from ethyl acetate and DMSO) did not result in a separation of the impurity. A part of the raw product obtained was purified by chromatography [silica gel 60 G (10 g); cyclohexane/ethyl acetate 2:8 (100 ml)]. The title compound with a melting point of 212-218° C. was thus isolated in an amount of 59 mg.

13C NMR (101 MHz, CDCl3) δ ppm: 24.6, 26.4*, 29.9, 32.3, 37.9, 45.6, 59.9* 67.6, 110.1, 110.6, 120.3, 122.7, 124.9, 125.8, 126.5, 127.3, 127.6, 134.4, 138.2*, 138.9, 198.2

* spread signals

Example 3

1-(imino(1-methyl-1H-indol-2-yl)methyl)-N1,N1,N4,N4-tetramethyl-4-phenylcyclohexane-1,4-diamine bis(2-hydroxypropane-1,2,3-tricarboxylate) (More Polar Diastereoisomer)

The more polar diastereoisomer from Example 1, step b) (248 mg, 0.66 mmol) was dissolved in propan-2-ol (5 ml) in the boiling heat and mixed with a hot solution of citric acid [382 mg, 2 mmol, in hot propan-2-ol (4 ml)]. A precipitate was separated out when the solution cooled to RT. The batch was left for 20 h at 5° C. to complete the precipitation, then the solid was separated by means of a fritted glass filter and dried. The citrate was thus obtained as bis-citrate with a yield of 380 mg (73%, melting point from 80° C.).

13C NMR (101 MHz, DMSO-D6) δ ppm: 24.0, 25.4 (propan-2-ol), 28.1, 31.4, 37.4, 37.5, 43.4, 62.0, 64.4 (propan-2-ol), 67.8, 71.8, 103.4, 110.2, 119.7, 121.0, 122.4, 126.2, 128.8, 129.2, 129.3, 130.2, 136.2, 137.8, 170.9, 171.2, 175.6

Example 4

(1,4-bis-dimethylamino-4-phenylcyclohexyl)-(1-methyl-1H-indol-2-yl)-methanone (More Non-polar Diastereoisomer)

The exemplary compound 1 (250 mg, 0.62 mmol) was mixed with 2N HCl (10 ml) and stirred for 3 h at RT and for 1 h at 50° C. (bath temperature). A precipitate separated out during the reaction time. For work up the reaction mixture was firstly neutralised with K2CO3 at room temperature and then strongly basified with 2N NaOH (1 ml). The aqueous phase was extracted with ethyl acetate (3×10 ml). The combined organic extracts were dried over MgSO4 and then concentrated to low volume. The residue obtained (240 mg) was purified by chromatography [silica gel 60 G (10 g);

cyclohexane/ethyl acetate 1:1, (100 ml)]. The title compound was thus separated from the starting product still present and obtained with a yield of 120 mg (48%) with a melting point of 165-169° C. (after re-crystallisation from ethanol).

13C NMR (101 MHz, CDCl$_3$) δ ppm: 24.2, 30.2, 32.3, 37.9, 38.8, 59.0, 69.6, 110.1, 111.5, 120.3, 122.9, 125.0, 125.8, 126.3, 126.8, 127.4, 134.8, 139.0, 139.3, 198.9

Example 5

(1,4-bis-dimethylamino-4-phenylcyclohexyl)-(1-methyl-1H-indol-2-yl)-methanone (More Polar Diastereoisomer)

The exemplary compound 3 (360 mg, 0.9 mmol) was mixed with 2N HCl (10 ml) and stirred for 4 h at 70° C. (bath temperature). For work up the reaction mixture was firstly neutralised with K$_2$CO$_3$ at room temperature and then strongly basified with 2N NaOH (1 ml). The aqueous solution was extracted with ethyl acetate (3×10 ml). The combined organic extracts were dried over MgSO$_4$ and then concentrated to low volume. The residue obtained (240 mg) was purified by chromatography [silica gel 60 G (10 g); cyclohexane/ethyl acetate 1:1, (150 ml), ethyl acetate (50 ml)]. The title compound was thus isolated with a yield of 234 mg (65%) with a melting point of 109-111° C. (after re-crystallisation from propan-2-ol).

13C NMR (101 MHz, CDCl3) δ ppm: 25.2, 29.8, 32.5, 38.3, 38.5, 61.8, 69.7, 110.2, 111.7, 120.3, 122.9, 125.1, 125.8, 126.5, 127.8, 127.9, 133.7, 136.8, 139.2, 198.4

Example 6

4-(imino(1-methyl-1H-indol-2-yl)methyl)-N,N-dimethyl-1-phenyl-4-(pyrrolidin-1-yl)cyclohexanamine (More Polar Diastereoisomer)

a) 4-dimethylamino-4-phenyl-1-(pyrrolidin-1-yl) cyclohexane carbonitrile

A mixture of methanol (50 ml) and water (50 ml) was acidified with hydrochloric acid (37%, 0.2 ml) and mixed with pyrrolidine (7.5 ml, 91 mmol) with ice cooling and stirring. 4-dimethylamino-4-phenylcyclohexanone (2.17 g, 10 mmol) was then added to the solution. The batch was stirred for 10 min to dissolve the ketone as completely as possible. KCN (1.6 g, 24.6 mmol) was then added. The ice cooling was removed and the batch stirred for 2 d at RT, during which white solid separated out. The batch was brought to approx. 0° C. again for 1 h by ice cooling to complete the precipitation. The precipitate was then separated by means of a fritted glass filter and dried in a vacuum at a bath temperature of 40° C. A diasteroisomer mixture of the title compound was obtained with a yield of 2.7 g (90%) and with a melting point of 136-142° C.

AS 09460: 13C NMR (101 MHz, CDCl3) δ ppm: 23.4, 23.5, 29.1*, 31.4, 32.3*, 37.7, 38.2, 48.0, 48.1, 58.8*, 60.3*, 61.8*, 62.2*, 119.7, 120.0, 126.7, 126.8, 127.4, 127.7, 127.9, 136.4*, 137.5*

* spread signals b) 4-(imino(1-methyl-1H-indol-2-yl)methyl)-N,N-dimethyl-1-phenyl-4-(pyrrolidin-1-yl)cyclohexanamine (More Polar Diastereoisomer)

N-methyl indole [1.31 g, 10 mmol, dissolved in dry THF (10 ml)] was added to a solution of n-butyl lithium (2.5N in n-hexane, 4 ml, 10 mmol) in dry THF (10 ml) with exclusion of moisture at 0° C. The batch was stirred for 60 min while maintaining the cooling, and a solid began to separate out after approx. 10 min. The diastereoisomer mixture from the previous step [1.49 g, 5 mmol, dissolved in dry THF (20 ml)] was then added within 20 min. After the addition had ended the cooling was removed and the batch stirred a further 18 h after RT was reached. For work up the batch was carefully mixed with a mixture of THF (5 ml) and water (1 ml). Then saturated NaCl solution (30 ml) was added to the mixture. The organic phase was separated, the aqueous phase was extracted with ethyl acetate (4×20 ml). The combined organic extracts were dried over MgSO$_4$ and then concentrated to low volume. The residue obtained (2.78 g) was purified by chromatography [silica gel 60 G (10 g); ethyl acetate (200 ml), ethyl acetate/ethanol 1:1 (50 ml)]. The more polar diastereoisomer could thus be isolated as a viscous mass with a yield of 6% (140 mg). The non-polar diastereomer was obtained as a mixture.

13C NMR (101 MHz, CDCl3) δ ppm: 24.2, 26.0, 29.8, 31.7, 38.2, 44.9, 61.3, 64.2, 104.9, 109.8, 119.9, 121.4, 122.7, 126.5, 127.0, 127.6, 127.7, 137.0, 137.3, 138.3, 175.2

Example 7

(4-dimethylamino-4-phenyl-1-(pyrrolidin-1-yl)cyclohexyl)-(1-methyl-1H-indol-2-yl)methanone (More Polar Diastereoisomer)

Exemplary compound 6, step b) (99 mg, 0.23 mmol) was mixed with 2N HCl (3 ml) and stirred for 18 h at RT. The solution turned orange in colour immediately after the acid was added. For work up the reaction mixture was basified with 2N NaOH (5 ml) at room temperature. The aqueous phase was extracted with dichloromethane (3×10 ml). The combined organic extracts were dried over MgSO$_4$ and then concentrated to low volume. The residue obtained (84 mg) was purified by chromatography [silica gel 60 G (10 g); ethyl acetate (120 ml)]. The title compound was thus isolated with a yield of 68 mg (68%) and a melting point from 134° C.

13C NMR (101 MHz, CDCl3) δ ppm: 24.1, 26.3*, 29.9, 32.4, 38.3, 45.3, 61.6*, 67.9, 110.2, 111.1, 120.3, 122.9, 125.0, 125.9, 126.5, 127.8, 127.9, 134.1, 136.9*, 139.1, 198.1

* spread signals

Example 8

N,N,N'-trimethyl-1,4-diphenyl-cyclohexane-1,4-diamine (Non-polar Diastereomer)

a) 4-dimethylamino-1-methylamino-4-phenyl-cyclohexane carbonitrile

40% aqueous methylamine solution (8.7 mL, 69 mmol) and 4-dimethylamino-4-phenylcyclohexanone (3.13 g, 14.4 mmol) dissolved in methanol (15 mL) were added to a solution of 4N hydrochloric acid (3.75 mL) and methanol (2.25 mL) cooled to 0° C. The reaction mixture was then mixed with potassium cyanide (2.25 g, 34 mmol) and stirred for 5 d at RT. For work up the mixture was mixed with water (60 mL) and extracted with ether (3×50 ml). The combined organic phases were dried with sodium sulphate and concentrated to low volume in a vacuum.

Yield: 3.48 g (94%), diastereomer mixture

1H-NMR (DMSO-d6): 1.31 (1 H, m); 1.64 (1 H, m); 1.79 (2 H, m); 1.93 (6 H, d); 2.03 (2 H, m); 2.22 and 2.34 (3 H, dd); 2.77 (1 H, m); 2.63 and 2.77 (1 H, m); 7.33 (5 H, m).

b) N,N,N'-trimethyl-1,4-diphenyl-cyclohexane-1,4-diamine (Non-polar Diastereomer)

Phenyl lithium (8.4 mL, 15 mmol, 1.8 M solution in dibutyl ether) was provided in argon and mixed drop by drop with a solution of the diastereoisomer mixture from the previous step (1.29 g, 5 mmol) in diethyl ether (15 mL) at RT. During this, the temperature of the reaction mixture increased to 35° C. and a solid separated out. The reaction mixture was boiled for 30 min with reflux (bath 50° C.), then hydrolysed in an ice bath (0-10° C.) with 20% NH$_4$Cl solution (10 mL) and the organic phase separated. The aqueous phase was extracted with ether (2×30 mL). The combined organic solutions were dried over Na$_2$SO$_4$ and concentrated to low volume in a vacuum.

The residue was separated by flash chromatography (50 g silica gel) with chloroform/methanol (20:1→9:1→1:1+1% TEA).

Yield: 283 mg (18%) non-polar diastereomer, oil

1H-NMR (DMSO-d6): 1.64 (2 H, m); 1.86 (3 H, s); 1.92 (6 H, s); 2.09 (6 H, m); 7.25 (2 H, m); 7.35 (6 H, m); 7.49 (2 H, m).

Example 9

N,N,N'-trimethyl-1,4-diphenyl-cyclohexane-1,4-diamine (Polar Diastereomer)

The analogous polar diastereomer could also be isolated during the purification of the exemplary compound 8 step b).

Yield: 306 mg (20%) polar diastereomer.

1H-NMR (DMSO-d6): 1.47 (2 H, m); 1.87 (5 H, m); 1.95 (6 H, s); 2.13 (4 H, m); 7.10 (1 H, m); 7.23 (5 H, m); 7.34 (4 H, m).

Example 10

N,N,N',N'-tetramethyl-1,4-diphenyl-cyclohexane-1,4-diamine (Non-polar Diastereomer)

A solution of the exemplary compound 8 (242 mg, 0.78 mmol) and formalin (1.1 mL, 37% aqueous solution) in acetonitrile (10 mL) was mixed in portions with sodium cyanoboron hydride (200 mg, 3.2 mmol) and stirred for 45 min at RT. Conc. acetic acid was then added until a neutral reaction occurred and was stirred for 45 min at RT. For work up the solvent was removed in a vacuum, the residue taken up in 2N NaOH (10 mL) and then extracted with ether (3×10 mL). The organic solution was dried over Na$_2$SO$_4$ and concentrated to low volume in a vacuum. The remaining residue was purified by flash chromatography with CHCl$_3$/MeOH (1:1).

Yield: 230 mg (92%)

Melting point: 117-118° C.

1H-NMR (DMSO-d6): 1.76 (4 H, wide); 1.96 (12 H, s); 2.28 (4 H, wide); 7.15 (2 H, m); 7.27 (8 H, m).

Example 11

N,N,N',N'-tetramethyl-1,4-diphenyl-cyclohexane-1,4-diamine (Polar Diastereomer)

A solution of the exemplary compound 9, step b) (223 mg, 0.72 mmol) and formalin (1.0 mL, 37% aqueous solution) in acetonitrile (10 mL) was mixed in portions with sodium cyanoboron hydride (182 mg, 2.9 mmol) and stirred for 45 min at RT. Conc. acetic acid was then added until a neutral reaction occurred and was stirred for 45 min at RT. For work up the solvent was removed in a vacuum, the residue was taken up in 2N NaOH (10 mL) and then extracted with ether (3×10 mL). The organic solution was dried over Na$_2$SO$_4$ and concentrated to low volume in a vacuum. The remaining residue was purified by flash chromatography with CHCl$_3$/MeOH (9:1).

Yield: 160 mg (69%)

Melting point: 197-198° C.

1H-NMR (CD3OD): 1.47 (4 H, d); 1.91 (12 H, s); 2.75 (4 H, d); 7.32 (2 H, m); 7.46 (8 H, m).

Example 12

1-benzyl-N,N,N',N'-tetramethyl-4-phenyl-cyclohexane-1,4-diamine (Non-polar Diastereomer)

a) 1,4-bis-dimethylamino-4-phenyl-cyclohexane carbonitrile

40% aqueous dimethylamine solution (14 mL, 110.5 mmol), 4-dimethylamino-4-phenylcyclohexanone (5.00 g, 23.04 mmol) and potassium cyanide (3.60 g, 55.3 mmol) were added to a mixture of 4N hydrochloric acid (14 mL) and methanol (5 mL) with ice cooling. The mixture was stirred for 2 d at room temperature and then after adding water (200 mL) was extracted with ether (4×150 mL). After the solution was concentrated to low volume, the residue was taken up in dichloromethane (200 mL) and dried with magnesium sulphate overnight, filtered and the solvent removed in a vacuum. The nitrile was obtained as an oil which was crystallised through.

Yield: 5.87 g (90%)

1H-NMR (DMSO-d6): 1.36 (1H, m); 1.61 (1 H, m); 1.61 (2 H, m); 1.92 (8 H, m); 2.16 (4 H, m); 2.28 (3 H, s); 2.44 (1 H, m); 2.59 (1 H, m); 7.35 (5 H, m).

b) 1-benzyl-N,N,N',N'-tetramethyl-4-phenyl-cyclohexane-1,4-diamine (Non-polar Diastereomer)

The title compound of the previous step (5.84 g, 20.5 mmol) was dissolved in THF (115 mL) and mixed in drops with benzyl magnesium chloride 2M (36 mL, 71.57 mmol) with ice cooling. The reaction mixture was stirred overnight at room temperature. The reaction mixture was mixed with 20% ammonium chloride solution (15 mL) and water (10 mL) and extracted with diethyl ether (3×50 mL). The combined organic phases were washed with water (50 mL) and saturated NaCl solution (50 mL), dried over Na$_2$SO$_4$, filtered and concentrated to low volume in vacuum.

The residue was purified by flash chromatography with cyclohexane/ethyl acetate (1:1).

Yield: 770 mg (11%) non-polar diastereomer

1H-NMR (DMSO-d6): 1.57 (4 H, m); 1.72 (2 H, m); 1.79 (6 H, s); 2.19 (6 H, s); 2.23 (2 H, m); 2.63 (2 H, s); 7.26 (10 H, m).

Example 13

1-benzyl-N,N,N',N'-tetramethyl-4-phenyl-cyclohexane-1,4-diamine (Polar Diastereomer)

The analogous polar diastereomer could also be isolated during the purification of the exemplary compound 12 step b).

The residue was purified by flash chromatography with cyclohexane/ethyl acetate (1:1). The non-polar diastereomer was obtained in clean state. The polar diastereomer was isolated in impure state and once again purified by flash chromatography with acetonitrile/methanol/1N NH$_4$Cl (9:1:1).

Yield: 600 mg (9%) polar diastereomer

1H-NMR (DMSO-d6): 0.88 (2 H, t); 1.70 (2 H, m); 1.85 (6H, s); 1.90 (2 H, m); 2.14 (2 H, m); 2.26 (6 H, s); 2.48 (2 H, s); 7.00 (6 H, m); 7.18 (4 H, m).

13C-NMR (DMSO-d6): 27.1; 28.6; 36.3; 36.8; 37.8; 57.0; 60.5; 125.2; 125.8; 127.1; 127.2; 130.2; 136.9; 138.7.

Example 14

4-methoxy-4-(3-(methoxymethyl)-1H-indol-2-yl)-N,N-dimethyl-1-phenylcyclohexanamine 2-hydroxypropane-1,2,3-tricarboxylate a) [4-methoxy-4-(3-methoxy-prop-1-ynyl)-1-phenyl-cyclohexyl]-dimethylamine Methyl propargyl ether (1.47 g, 21.0 mmol) dissolved in abs. THF (15 mL) was added in drops to a 2.5 M solution of butyl lithium in hexane (8.4 mL, 21.0 mmol) at −30° C. in argon. A solution of 4-dimethylamino-4-phenylcyclohexanone (4.34 g, 20.0 mmol) in abs. THF (20 mL) and lithium bromide (0.87 g, 10 mmol) dissolved in abs. THF (2.5 mL) was then added at −30° C. The reaction mixture was heated to −5° C., mixed drop by drop with a solution of methyl iodide (4.25 g, 30 mmol) in abs. DMSO (25 mL) and stirred for 2 h at 50° C. For work up of the reaction mixture water (30 mL) was added with ice bath cooling and extracted with cyclohexane (4×50 mL). The organic phase was washed with 20% ammonium chloride solution, dried over Na$_2$SO$_4$ and concentrated to low volume in a vacuum. The remaining residue was purified by flash chromatography with CHCl$_3$/MeOH (20:1).

Yield: 2.34 g (39%)

1H-NMR (DMSO-d6): 1.57 (2 H, m); 1.96 (10 H, m); 2.25 (2 H, m); 3.18 (3 H, s); 3.27 (3 H, m); 4.05 (2 H, s); 7.37 (5 H, m).

b) [4-Methoxy-4-(3-methoxy-prop-1-ynyl)-1-phenyl-cyclohexyl]-dimethylamine 2-iodoaniline (328 mg, 1.5 mmol), the title compound of the previous step (452 mg, 1.5 mmol) and sodium carbonate (795 mg, 7.5 mmol) were dissolved in abs. DMF (10 mL) in argon. The catalyst (PEPPSI®, 204 mg, 0.3 mmol) was then added and the solution stirred for 24 h at 100° C. For work up the black reaction solution was concentrated in a vacuum until dry, the residue was dissolved in CHCl$_3$ and washed with water. The organic phase was dried over Na$_2$SO$_4$ and concentrated to low volume in a vacuum. The remaining residue was purified by flash chromatography with CHCl$_3$/MeOH (20:1→9:1).

Yield: 71 mg (12%)

1H-NMR (DMSO-d6): 1.62 (2 H, m); 2.22 (10 H, m); 2.63 (2 H, m); 3.00 (3 H, s); 3.10 (3 H, m); 4.46 (2 H, s); 6.95 (2 H, m); 7.28 (1 H, d); 7.46 (6 H; m); 10.72 (1 H, s).

c) 4-methoxy-4-(3-(methoxymethyl)-1H-indol-2-yl)-N,N-dimethyl-1-phenylcyclohexanamine 2-hydroxypropane-1,2,3-tricarboxylate The title compound of the previous step (217 mg, 0.55 mmol) was dissolved in hot ethanol (4 mL) and mixed with a solution of citric acid (106 mg, 0.55 mmol) in hot ethanol (2 mL). After standing for 2 h in the refrigerator and adding ether, the solid formed was aspirated and dried in a vacuum.

Yield: 165 mg (51%)

Melting point: 184-186° C.

1H-NMR (DMSO-d6): 1.61 (2 H, m); 2.22 (4 H, m); 2.37 (6 H, s); 2.52 (4 H, m); 3.01 (3 H, s); 3.08 (3 H, m); 4.45 (2 H, s); 6.99 (2 H, m); 7.25 (1 H, d); 7.50 (4 H, m); 7.65 (2 H, m); 10.73 (1 H, s).

Example 15

4-(benzyloxy)-4-(3-(methoxymethyl)-1H-indol-2-yl)-N,N-dimethyl-1-phenylcyclohexanamine a) [4-benzyloxy-4-(3-methoxy-prop-1-ynyl)-1-phenyl-cyclohexyl]-dimethylamine Methyl propargyl ether (0.36 g, 5.2 mmol) dissolved in abs. THF (5 mL) was added in drops to a 2.5 M solution of butyl lithium in hexane (2.1 mL, 5.2 mmol) at −30° C. in argon. A solution of 4-dimethylamino-4-phenylcyclohexanone (1.08 g, 5.0 mmol) in abs. THF (5 mL) and lithium bromide (0.22 g, 2.5 mmol) dissolved in abs. THF (2.0 mL) was then added at −30° C. The reaction mixture was heated to −5° C., mixed in drops with a solution of benzyl bromide (1.28 g, 7.5 mmol) in abs. DMSO (10 mL) and stirred 2 h at 50° C. For work up of the reaction mixture water (10 mL) was added with ice bath cooling and extracted with cyclohexane (4×20 mL). The organic phase was washed with 20% ammonium chloride solution, dried over Na$_2$SO$_4$ and concentrated to low volume in a vacuum. The remaining residue was purified by flash chromatography with CHCl$_3$/MeOH (40:1).

Yield: 541 g (29%), non-polar compound

1H-NMR (DMSO-d6): 1.67 (2 H, m); 1.94 (6 H, s); 2.04 (4 H, m); 2.30 (2 H, m); 3.19 (3 H, s); 4.09 (2 H, s); 4.60 (2 H, s); 7.31 (10 H, m).

b) 4-(benzyloxy)-4-(3-(methoxymethyl)-1H-indol-2-yl)-N,N-dimethyl-1-phenylcyclohexanamine 2-acetylamino-iodoaniline (359 mg, 1.37 mmol), the title compound of the previous step (519 mg, 1.37 mmol) and sodium carbonate (726 mg, 6.85 mmol) were dissolved in abs. DMF (10 mL) in argon. The catalyst (PEPPSI, 190 mg, 0.28 mmol) was then added and the solution stirred for 24 h at 100° C. For work up the black reaction solution was concentrated in a vacuum until dry, the residue dissolved in CHCl$_3$ and washed with water. The organic phase was dried over Na$_2$SO$_4$ and concentrated to low volume in a vacuum. The remaining residue was purified by flash chromatography with CHCl$_3$/MeOH (50:1).

Yield: 210 mg (33%)

1H-NMR (DMSO-d6): 1.67 (2 H, m); 1.61 (2 H, m); 2.10 (6 H, bs); 2.38 (2 H, m); 2.70 (2 H, m); 3.11 (3 H, s); 4.13 (2 H, s); 4.57 (2 H, s); 7.02 (2 H, m); 7.30 (12 H, m); 10.78 (1 H, s).

Example 16

4-ethoxy-4-(3-(methoxymethyl)-1H-indol-2-yl)-N,N-dimethyl-1-phenylcyclohexanamine 2-hydroxypropane-1,2,3-tricarboxylate a) [4-ethoxy-4-(3-methoxy-prop-1-ynyl)-1-phenyl-cyclohexyl]-dimethylamine Methyl propargyl ether (1.47 g, 21.0 mmol) dissolved in abs. THF (15 mL) was added in drops to a 2.5 M solution of butyl lithium in hexane (8.4 mL, 21.0 mmol) at −30° C. in argon. A solution of 4-dimethylamino-4-phenylcyclohexanone (4.34 g, 20.0 mmol) in abs. THF (20 mL) and lithium bromide (0.87 g, 10 mmol) dissolved in abs. THF (2.5 mL) was then added at −30° C. The reaction mixture was heated to −5° C., mixed in drops with a solution of ethyl iodide (4.68 g, 30 mmol) in abs. DMSO (30 mL) and stirred for 2 h at 50° C. For work up of the reaction mixture water (30 mL) was added with ice bath cooling and extracted with cyclohexane (4×50 mL). The organic phase was washed with 20% ammonium chloride solution, dried over $Na_2SO_4$ and concentrated to low volume in a vacuum. The remaining residue was purified by flash chromatography with $CHCl_3$/MeOH (20:1).

Yield: 3.92 g (62%)

1H-NMR (DMSO-d6): 1.12 (3 H, t); 1.58 (2 H, m); 1.96 (10 H, m); 2.25 (2 H, m); 3.17 (3 H, s); 3.51 (2 H, q); 4.04 (2 H, s); 7.37 (5 H, m)

b) [4-ethoxy-4-(3-methoxymethyl-1H-indol-2-yl)-1-phenyl-cyclohexyl]-dimethylamine N-(2-iodo-phenyl)-acetamide (522 mg, 2.0 mmol), the title compound of the previous step (631 mg, 2.0 mmol) and sodium carbonate (1.06 g, 10.0 mmol) were dissolved in abs. DMF (10 mL) in argon. The catalyst (PEPPSI, 272 mg, 0.4 mmol) was then added and the solution stirred for 24 h at 100° C. For work up the black reaction solution was concentrated in a vacuum until dry, the residue dissolved in $CHCl_3$ and washed with water. The organic phase was dried over $Na_2SO_4$ and concentrated to low volume in a vacuum. The remaining residue was purified by flash chromatography with $CHCl_3$/MeOH (50:1).

Yield: 249 mg (31%)

1H-NMR (DMSO-d6): 1.11 (3 H, t); 1.61 (2 H, m); 1.99 (8 H, m); 2.19 (2 H, m); 2.48 (2 H, m); 3.12 (5 H, m); 4.53 (2 H, s); 6.99 (2 H, m); 7.27 (2 H, d); 7.47 (5 H, m); 10.61 (1 H, s).

c) 4-ethoxy-4-(3-(methoxymethyl)-1H-indol-2-yl)-N,N-dimethyl-1-phenylcyclohexanamine 2-hydroxy-propane-1,2,3-tricarboxylate The title compound of the previous step (188 mg, 0.462 mmol) was dissolved in hot ethanol (4 mL) and mixed with a solution of citric acid (89 mg, 0.462 mmol) in hot ethanol (2 mL). After standing for 2 h in the refrigerator and adding ether, the solid formed was aspirated and dried in a vacuum.

Yield: 152 mg (55%)

Melting point: 166-167° C.

1H-NMR (DMSO-d6): 1.12 (3 H, t); 1.57 (2 H, m); 2.17-2.35 (10 H, m); 2.58 (4 H, m); 2.70 (2 H, m); 3.11 (3 H, m); 4.51 (2 H, s); 6.98 (2 H, m); 7.24 (2 H, d); 7.43 (4 H, m); 7.62 (2 H, m); 10.67 (1 H, s).

Example 17

N-((-4-(dimethylamino)-1-methyl-4-phenylcyclohexyl)methyl)acetamide 2-hydroxypropane-1,2,3-tricarboxylate a) dimethyl-(4-methylene-1-phenyl-cyclohexyl)-amine

Tert-BuOK (0.550 g, 4.74 mmol) was provided in abs. ether (10 mL) in argon and methyl triphenyl phosphonium bromide (1.89 g, 4.74 mmol) added. The mixture was then heated to 40° C. for 30 min. After this reaction time 4-dimethylamino-4-phenylcyclohexanone (1.00 g, 4.60 mmol) dissolved in abs. THF (10 mL) was carefully added in drops and the reaction solution was heated to 50° C. for 5 h. The reaction batch was stirred overnight at room temperature and concentrated in a vacuum until dry. The residue was taken up in dioxan (50 mL) and mixed with HCl/dioxan (5 mL). The precipitated solid was aspirated and washed with ether. The isolated hydrochloride was basified with 2 N NaOH and extracted with dichloromethane (2×80 mL). The organic phase was dried over $Na_2SO_4$, filtered and concentrated to low volume in a vacuum.

Yield: 0.86 g (61%)

1H-NMR (DMSO-d6): 1.82 (2 H, m); 1.99 (2 H, m); 2.30 (2 H, m); 2.43 (6 H, d); 3.01 (2 H, m); 4.67 (2 H, s); 7.55 (3 H, m); 7.72 (2 H, m).

b) 4-dimethylamino-1-methyl-4-phenyl-cyclohexane carbonitrile

R—R-cobalt(II)-salen complex (Jacobsen's ligand, 26.0 mg, 0.04 mmol) was dissolved in dichloromethane (5 mL), mixed with acetic acid (29 μL, 0.08 mmol, 2 eq.) and stirred in an open flask for 30 min. The batch was then concentrated to low volume in a vacuum and the excess acetic acid was azeotropically removed with toluol. The cobalt(III) catalyst produced was provided in abs. ethanol (5 mL) in argon. After 2 min the title compound of the previous step (0.860, 3.99 mmol) dissolved in ethanol (8 mL), p-toluol sulphonyl cyanide (714 mg, 5.58 mmol) were added followed by phenyl silane (0.49 mL, 3.99 mmol). Ethanol (5 mL) was then added once again and the reaction solution was stirred for 3 d at room temperature. The batch was concentrated in a vacuum until dry and the residue purified by flash chromatography (2× on normal silica gel and 1× on ultrafine silica gel) with ethyl acetate. Further studies have shown that a single purification by column chromatography on ultrafine silica gel with chloroform/methanol (20:1) was sufficient.

Yield: 0.130 g, (13%)

1H-NMR (DMSO-d6): 1.09 (2 H, m); 1.16 (3 H, s); 1.78 (2 H, m); 1.87 (2 H, m); 1.92 (6 H, s); 2.56 (2 H, m); 7.32 (5 H, m).

13C-NMR (DMSO-d6): 25.4; 29.8; 33.1; 33.7; 37.8; 60.3; 124.5; 126.5; 127.5; 127.7; 135.4.

c) (4-aminomethyl-4-methyl-1-phenyl-cyclohexyl)-dimethylamine $LiAlH_4$ (38.0 mg, 0.81 mmol) was provided in abs. THF (5 mL) in argon, slowly mixed with the title compound of the previous step (0.130 g, 0.54 mmol) dissolved in abs. THF (5 mL) and the reaction mixture stirred for 3 h with reflux. THF (10 mL) and water (4 mL) were then added with ice cooling and the mixture stirred again for 30 min. The precipitate was filtered off over celite and washed with dichloromethane (50 mL). The filtrate was concentrated in a vacuum until dry.

Yield: 0.12 g (90%)

1H-NMR (DMSO-d6): 0.72 (3 H, s); 0.99 (2 H, m); 1.13 (2 H, t, NH2); 1.50 (2 H, m); 1.84 (2 H, m); 1.90 (6 H, s); 2.04 (2 H, m); 2.39 (2 H, t); 7.24 (5 H, m).

d) N-(4-dimethylamino-1-methyl-4-phenyl-cyclohexylmethyl)-acetamide

The title compound of the previous step (0.120 g, 0.48 mmol) was dissolved in abs. THF (2.5 mL) and mixed with triethylamine (72.0 μL, 0.53 mmol) and acetyl chloride (42.0 mg, 38.0 μl, 0.53 mmol). The reaction mixture was stirred for 16 h at room temperature. The batch was concentrated in a vacuum until dry, the residue taken up in ethyl acetate (10 mL) and washed with saturated NaHCO$_3$ solution (2×10 mL) and with saturated NaCl solution. The organic phase was dried over Na$_2$SO$_4$, filtered and concentrated to low volume in a vacuum.

Yield: 109 mg (77%)

1H-NMR (DMSO-d6): 0.71 (3 H, s); 0.96 (2 H, m); 1.17 (2 H, m); 1.47 (2 H, m); 1.84 (3 H, s); 1.91 (6H, s); 2.11 (2 H, m); 3.02 (2 H, d) 7.30 (5 H, m); 7.69 (1 H, t).

e) N-((-4-(dimethylamino)-1-methyl-4-phenylcyclohexyl)methyl)acetamide 2-hydroxypropane-1,2,3-tricarboxylate The title compound of the previous step (102 mg, 0.35 mmol) was dissolved in hot ethanol (4 mL). Citric acid (67.0 mg, 0.35 mmol) was dissolved in hot ethanol (1.0 mL) and added. The batch was subsequently stirred for 2 h at room temperature. Since no precipitate separated out, the solution was concentrated to low volume in a vacuum. The residue had ether stirred through it, was concentrated once again in a vacuum and then dried in a vacuum. The desired citrate was obtained as a porous solid.

Yield: 167 mg (98%)

1H-NMR (DMSO-d6): 0.62 (3 H, s); 0.92 (2 H, m); 1.45 (2 H, m); 1.83 (3 H, s); 2.07-2.60 (14 H, m); 3.07 (2 H, d) 7.46 (5 H, m); 7.72 (1 H, t).

Example 18

4-chloro-N-((-4-(dimethylamino)-1-methyl-4-phenylcyclohexyl)methyl)benzol sulphonamide 2-hydroxypropane-1,2,3-tricarboxylate a) 4-chloro-N-(4-dimethylamino-1-methyl-4-phenyl-cyclohexylmethyl)-benzol sulphonamide The title compound from Example 17, step c) (0.160 g, 0.65 mmol) was dissolved in abs. THF (3.4 mL), mixed with triethylamine (97 mL, 0.714 mmol) and 4-chlorobenzol sulphonic acid chloride (151 mg, 0.71 mmol) and stirred for 1 d at room temperature. The batch was concentrated in a vacuum until dry and the residue purified by flash chromatography: 1st column with ethyl acetate/ethanol (9:1) and 2nd column with ethyl acetate.

Yield: 70 mg (26%)

1H-NMR (DMSO-d6): very poor spectrum resolution b) 4-chloro-N-((-4-(dimethylamino)-1-methyl-4-phenylcyclohexyl)methyl)benzol sulphonamide 2-hydroxypropane-1,2,3-tricarboxylate The title compound of the previous step (0.070 g, 0.17 mmol) was dissolved in hot isopropanol (4 mL). Citric acid (32.0 mg, 0.17 mmol) was dissolved in hot isopropanol (1.0 mL) and added. The batch was stirred for 2 h at room temperature. Since no precipitate separated out, the solution was concentrated to low volume in a vacuum. The residue had ether stirred through it, was concentrated once again in a vacuum and then dried in a vacuum. The desired citrate was obtained as a porous solid.

Yield: 58 mg (57%)

1H-NMR (DMSO-d6): 0.64 (3 H, m); 0.90-1.04 (6 H, m); 1.54 (2 H, m); 1.92 (2 H, m); 2.31 (6 H, s); 2.73 (4 H, m); 7.47-7.84 (5 H, m); 10.8 (2 H, wide).

Example 19

N-((1-butyl-4-(dimethylamino)-4-phenylcyclohexyl)methyl)-4-chlorobenzol sulphonamide 2-hydroxypropane-1,2,3-tricarboxylate a) (4-butylidene-1-phenyl-cyclohexyl)-dimethylamine Potassium tert-butylate (2.75 g, 23.7 mmol) was provided in abs. ether (50 mL) in argon and mixed with butyl-triphenyl phosphonium bromide (9.45 g, 23.7 mmol). The batch was heated for 30 min to 40° C. 4-dimethylamino-4-phenyl cyclohexanone (5.00 g, 23.0 mmol) dissolved in abs. THF (50 mL) was then added carefully in drops (exothermic reaction). The batch was heated for 6.5 h to 50° C. and stirred overnight at room temperature. The batch was then concentrated in a vacuum until dry, taken up in dioxan (20 mL) and mixed with HCl/dioxan (5 mL). A precipitate separated out during this. This was filtered off, washed with ether (10 mL), then basified with 2N NaOH and extracted with dichloromethane (2×40 mL). The organic phase was dried over Na$_2$SO$_4$, filtered and concentrated in a vacuum until dry.

Yield: 4.60 g (77%)

1H-NMR (DMSO-d6): 0.83 (3 H, t); 1.27 (2 H, m); 1.94 (9 H, m); 2.09 (5 H, m); 2.29 (2 H, m); 5.04 (1 H, t); 7.23 (1 H, m); 7.36 (4 H, m).

b) 1-butyl-4-dimethylamino-4-phenyl-cyclohexane carbonitrile

The cobalt(III) catalyst (297 mg, 0.456 mmol) was provided in abs. ethanol (100 mL) in argon. The title compound of the previous step (11.6 g, 45.3 mmol) dissolved in ethanol (40 mL) was then added and p-toluol sulphonyl cyanide (13.0 g, 68.0 mmol), phenyl silane (5.6 mL, 45.3 mmol) and ethanol (10 mL) were then added. The temperature rose to 35° C. and therefore the mixture was cooled with ice water. The batch was stirred for 72 h at room temperature and then concentrated in a vacuum until dry. The residue was purified by flash chromatography with chloroform/methanol (20:1). The pre-purified substance was purified again by MPLC column chromatography with chloroform/methanol (50:1, 20:1).

Yield: 0.233 g (1.8%)

1H-NMR (DMSO-d6): 0.83 (3 H, t); 1.08 (2 H, m); 1.27 (6 H, m); 1.75 (2 H, m); 1.93 (8 H, m); 2.63 (2 H, m); 7.36 (5 H, m).

c) (4-aminomethyl-4-butyl-1-phenyl-cyclohexyl)-dimethylamine

The title compound of the previous step (247 mg, 0.856 mmol) was dissolved in abs. THF (5 mL). LiAlH$_4$ (64 mg, 1.71 mmol) was then added in argon and the batch heated to boiling for 5.5 h. For work up THF (12 mL) and H$_2$O (5 mL) were added to the batch and this was subsequently stirred for 30 min. The batch was filtered via a fritted glass filter with diatomaceous earth (2 cm), rinsed with dichloromethane (50 mL) and chloroform (50 mL) and concentrated to low volume in a vacuum. The residue was purified by flash chromatography with chloroform/methanol (20:1, 9:1, methanol).

Yield: 70 mg (28%)

1H-NMR (DMSO-d6): 0.80 (3 H, t); 1.08 (9 H, m); 1.45 (2 H, m); 1.93 (10 H, m); 2.45 (2 H, m); 7.31 (5 H, m).

d) N-(1-butyl-4-dimethylamino-4-phenyl-cyclohexylmethyl)-4-chlorobenzol sulphonamide The title compound of the previous step (65.0 mg, 0.225 mmol) was dissolved in abs. THF (5 mL) in argon and mixed with triethylamine (33.5 µL, 0.247 mmol). 4-chlorobenzol sulphonic acid chloride (52.0 mg, 0.247 mmol) was then added to the batch. The batch was stirred overnight at room temperature. It was then concentrated in a vacuum until dry. The residue was taken up in ethyl acetate (10 mL) and washed with saturated NaHCO$_3$ solution (2×10 mL) and with saturated NaCl solution (2×10 mL) solution. The organic phase was dried over Na$_2$SO$_4$, filtered and concentrated in a vacuum until dry.

Yield: 103 mg (98%)

1H-NMR (DMSO-d6): 0.76 (3 H, t); 0.97 (8 H, m); 1.44 (2 H, m); 1.87 (10 H, m); 2.63 (2 H, m); 7.35 (5H, m); 7.52 (1 H, t); 7.68 (2 H, m); 7.85 (2 H, m).

e) N-((1-butyl-4-(dimethylamino)-4-phenylcyclohexyl)methyl)-4-chlorobenzol sulphonamide 2-hydroxypropane-1,2,3-tricarboxylate The title compound of the previous step (103 mg, 0.22 mmol) was dissolved in hot ethanol (3 mL). Citric acid (42 mg, 0.22 mmol) was dissolved in hot ethanol (1 mL) and added. The batch was cooled to room temperature and then concentrated in a vacuum until dry.

Yield: 128 mg (88%)

Melting point: porous solid?

1H-NMR (DMSO-d6): 0.86 (3 H, t); 0.94 (6 H, m); 1.10 (2 H, m); 1.50 (2 H, m); 1.86 (2 H, m); 2.28 (6 H, s); 2.51-2.64 (6 H, m); 7.52 (6 H, m); 7.72 (2 H, t); 7.87 (2 H, m).

Example 20

(-4-(dimethylamino)-4-phenyl-1-(4-phenylbutyl) cyclohexyl)methanol (Non-polar Diastereoisomer)

a) 1,4-dioxaspiro[4,5]decane-8-carboxylic acid ethyl ester

A solution of ethyl-4-oxocyclohexane carboxylate (28.9 g, 169 mmol), ethylene glycol (36.7 g, 33.0 mL, 592 mmol) and p-toluol sulphonic acid (380 mg, 2.0 mmol) in toluol (90 mL) was stirred overnight at room temperature. The reaction solution was poured into ether (150 mL) and washed with water and 5% sodium hydrogencarbonate solution (150 mL each). The organic phase was dried with sodium sulphate and concentrated to low volume in a vacuum. Since the raw product (26.8 g) was obtained in pure form, it could be directly converted further.

Yield: 26.8 g (74%), colourless oil b) 8-(4-phenylbutyl)-1,4-dioxaspiro[4,5]decane-8-carboxylic acid ethyl ester A 2.5 M solution of n-butyl lithium (2.5 g, 15.7 mL, 39.2 mmol) was slowly added in drops to a solution of diisopropylamine (3.96 g, 5.50 mL, 39.2 mmol) in absolute tetrahydrofuran (50 mL) at −78° C. in argon. 1,3-dimethyl-3,4,5,6-tetrahydro-2(1H)pyrimidone (DMPU, 10.0 g, 9.42 mL, 78.2 mmol) and a solution of the title compound of the previous step (8.40 g, 39.2 mmol) in absolute tetrahydrofuran (30 mL) were added in drops one after the other to this mixture. The reaction solution was further stirred for 2 h at this temperature before a solution of 1-bromo-4-phenylbutane (10.0 g, 47.0 mmol) in absolute tetrahydrofuran (50 mL) was added in drops. The resulting solution was stirred overnight at room temperature. Saturated ammonium chloride solution (50 mL) was then added and extracted with ether (2×50 mL). The combined organic phases were washed with saturated sodium chloride solution (50 mL), dried with sodium sulphate and concentrated to low volume in a vacuum. The raw product (17.7 g) was purified by means of flash chromatography (400 g, 20×7.5 cm) with cyclohexane/ethyl acetate (9:1).

Yield: 10.3 g (76%), colourless oil

1H-NMR (DMSO-d6): 1.12 (t, 3H, J=7.1 Hz); 1.39-1.62 (m, 12H); 1.91-2.03 (m, 2H); 2.54 (t, 2H, J=7.4 Hz); 3.82 (s, 4H); 4.05 (q, 2H, J=7.1 Hz); 7.12-7.17 (m, 3H); 7.22-7.28 (m, 2H).

c) [8-(4-phenylbutyl)-1,4-dioxaspiro[4.5]dec-8-yl] methanol

A solution of the title compound of the previous step (10.2 g, 33.5 mmol) in absolute tetrahydrofuran (50 mL) was added in drops to a suspension of lithium aluminium hydride (2.50 g, 67.0 mmol) in absolute tetrahydrofuran (100 mL) in argon at 65° and stirred for 3 h at this temperature, after which the conversion was complete. After cooling the reaction mixture was mixed with water (4.5 mL) and 4N sodium hydroxide solution (1.1 mL) and filtered from the precipitate formed. The residue was washed with tetrahydrofuran (2×60 mL) and the filtrate concentrated to low volume in a vacuum. Since the product was obtained in pure form, it could be directly converted further.

Yield: 9.44 g (93%), light yellow oil

1H-NMR (DMSO-d6): 1.14-1.32 (m, 6H); 1.34-1.39 (m, 2H); 1.40-1.57 (m, 6H); 2.57 (t, 2H, J=7.4 Hz); 3.17 (d, 2H, J=5.2 Hz); 3.82 (s, 4H); 4.36 (t, 1H, J=5.2 Hz); 7.13-7.19 (m, 3H); 7.24-7.29 (m, 2H).

d) 4-hydroxymethyl-4-(4-phenylbutyl)cyclohexanone

A solution of the title compound from the previous step (9.40 g, 30.9 mmol) in acetone (150 mL) was mixed with 1 N hydrochloric acid (32 mL) and stirred overnight at room temperature. The reaction solution was adjusted to pH 8 with 1N sodium hydroxide solution and concentrated to low volume in a vacuum. The residue was mixed with water (50 mL) and then extracted with dichloromethane (3×50 mL). The combined organic phases were washed with saturated sodium chloride solution (30 mL), dried with sodium sulphate and concentrated to low volume in a vacuum. Since the product was obtained in pure state, it could be directly converted further.

Yield: 7.96 g (99%), light yellow oil

1H-NMR (DMSO-d6): 1.19-1.67 (m, 10H); 2.22 (t, 4H, J=6.8 Hz); 2.59 (t, 2H, J=7.5 Hz); 3.30 (d, 2H, J=5.2 Hz); 4.54 (t, 1H, J=5.1 Hz); 7.13-7.21 (m, 3H); 7.24-7.29 (m, 2H).

e) 4-(1-ethoxy-ethoxymethyl)-4-(4-phenylbutyl)cyclohexanone

A solution of the title compound of the previous step (7.95 g, 30.5 mmol) in absolute dichloromethane (100 mL) was mixed with pyridinium tosylate (100 mg) and ethyl vinyl ether (2.64 g, 3.51 mL, 36.6 mmol) and stirred overnight at room temperature. The reaction solution was then washed with 5% sodium hydrogencarbonate solution, water (2×50 mL each) and saturated sodium chloride solution (50 mL) one after the other, dried with sodium sulphate and concentrated to low volume in a vacuum. The raw product (8.87 g) was purified by means of flash chromatography (400 g, 20×7.5 cm) with cyclohexane/ethyl acetate (9:1).

Yield: 6.97 g (69%), colourless oil

1H-NMR (DMSO-d6): 1.09 (t, 3H, J=7.0 Hz); 1.17 (d, 3H, J=5.3 Hz); 1.21-1.32 (m, 2H); 1.43-1.50 (m, 2H); 1.52-1.70 (m, 6H); 2.20-2.26 (m, 4H); 2.59 (t, 2H, J=7.5 Hz); 3.24 (d, 1H, J=9.4 Hz); 3.34-3.42 (m, 2H); 3.49-3.59 (m, 1H); 4.62 (q, 1H, J=5.3 Hz); 7.14-7.29 (m, 5H).

f) 1-dimethylamino-4-(1-ethoxyethoxymethyl)-4-(4-phenylbutyl)cyclohexane carbonitrile Firstly 40% dimethylamine solution (3.74 mL, 24.2 mmol) and then the title compound of the previous step (2.04 g, 6.1 mmol) and potassium cyanide (953 mg, 14.6 mmol) were added to an ice-cooled mixture of 4N hydrochloric acid (1.52 mL, 6.1 mmol) and methanol (1.7 mL). The suspension formed was stirred for 4 h at room temperature. The suspension was mixed with water (100 mL) and then extracted with diethyl ether (3×100 mL). The combined organic phases were dried with sodium sulphate and concentrated to low volume in a vacuum.

Yield: 2.30 g (97%), light yellow oil

1H-NMR (DMSO-d6): 1.08 (dt, 3H, J=2.5, 7.0 Hz, 1.075 (t, 1.5H, J=7.0 Hz); 1.085 (t, 1.5H, J=7.0 Hz); 1.14-1.18 (m, 3H); 1.19-1.39 (m, 6H); 1.41-1.68 (m, 6H); 1.89-2.00 (m, 2H); 2.22 (s, 2.6H); 2.23 (s, 3.4H); 2.53-2.62 (m, 2H); 3.10 (d, 0.5H, J=9.3 Hz); 3.13 (d, 0.5H, J=9.2 Hz); 3.22-3.29 (m, 1H); 3.33-3.39 (m, 1H); 3.47-3.59 (m, 1H); 4.56-4.63 (m, 1H); 7.13-7.29 (m, 5H).

g) [4-(1-ethoxyethoxymethyl)-1-phenyl-4-(4-phenylbutyl)cyclohexyl]dimethylamine A solution of the title compound of the previous step (diastereoisomer mixture, 2.30 g, 5.9 mmol) in absolute tetrahydrofuran (30 mL) was slowly added in drops to an ice-cooled 2M solution of phenylmagnesium chloride (2.03 g, 7.4 mL, 14.8 mmol) in tetrahydrofuran in argon and then stirred overnight at room temperature. The reaction solution was mixed with saturated ammonium chloride solution and water (20 mL each), the phases separated and the aqueous phase extracted with diethyl ether (3×30 mL). The combined organic phases were washed with saturated sodium chloride solution (30 mL), dried with sodium sulphate and concentrated to low volume in a vacuum. 2.73 g of raw product were formed as diastereoisomer mixture, which was completely separated by means of MPLC (LiChroprep Si60 15-25 μm, 230 g, 3.6×46 cm) with ethyl acetate/methanol (9:1).

Non-polar Diastereoisomer:

Yield: 918 mg (35%), light yellow oil

1H-NMR (DMSO-d6): 1.00 (t, 3H, J=7.1 Hz); 1.06 (d, 3H, J=5.3 Hz); 1.10-1.20 (m, 2H); 1.21-1.29 (m, 2H); 1.32-1.48 (m, 2H); 1.51-1.62 (m, 2H); 1.90 (s, 6H); 1.92-1.99 (m, 4H); 2.59 (t, 2H, J=7.6 Hz); 2.98 (d, 1H, J=9.3 Hz); 3.11 (d, 1H, J=9.3 Hz); 3.21-3.29 (m, 2H); 3.39-3.50 (m, 2H); 4.48 (q, 1H, J=5.3 Hz); 7.13-7.37 (m, 10H).

h) (-4-(dimethylamino)-4-phenyl-1-(4-phenylbutyl)cyclohexyl)methanol (Non-polar Diastereoisomer)

A solution of the title compound (non-polar diastereoisomer) of the previous step (469 mg, 1.1 mmol) in acetone (50 mL) was mixed with 2N hydrochloric acid (2 mL) and stirred for 18 h at room temperature. The reaction solution was adjusted to pH 8 with 1N sodium hydroxide solution, concentrated to low volume in a vacuum, the residue taken up in water (50 mL) and extracted with dichloromethane (3×30 mL). The combined organic phases were washed with saturated sodium chloride solution (30 mL), dried with sodium sulphate and concentrated to low volume in a vacuum. The raw product (381 mg) was purified by means of flash chromatography (18 g, 20×2.0 cm) with ethyl acetate/methanol (4:1).

Yield: 325 mg (81%), white solid

Melting point: 105-106° C.

1H-NMR (DMSO-d6): 1.00-1.14 (m, 2H); 1.18-1.28 (m, 2H); 1.29-1.41 (m, 4H); 1.49-1.60 (m, 2H); 1.81-1.85 (m, 1H); 1.90 (s, 6H); 1.94-2.06 (m, 3H); 2.59 (t, 2H, J=7.7 Hz); 3.02 (d, 2H, J=5.2 Hz); 4.21 (t, 1H, J=5.2 Hz); 7.13-7.37 (m, 10H).

13C-NMR (DMSO-d6): 22.4; 28.1; 28.2; 32.2; 34.1; 34.3; 35.9; 36.7; 37.9; 60.1; 66.2; 125.5; 125.7; 126.0; 127.2; 127.3; 128.1; 128.2; 137.4; 142.4.

LC-MS (Method: ASCA-7MIN-80 degrees.M): m/z: [M+1]+=366.6, Rt 2.38 min.

Example 21

(-4-(dimethylamino)-4-phenyl-1-(4-phenylbutyl)cyclohexyl)methanol (Polar Diastereoisomer)

a) [4-(1-ethoxyethoxymethyl)-1-phenyl-4-(4-phenylbutyl)cyclohexyl]dimethylamine In the synthesis step of Example 20, step g), the polar diastereoisomer was also obtained in pure state during the chromatographic separation.

Polar Diastereoisomer: 700 mg (27%), light yellow oil

1H-NMR (DMSO-d6): 0.96-1.23 (m, 14H); 1.36-1.57 (m, 4H); 1.90 (s, 6H); 1.92-2.00 (m, 4H); 2.45-2.47 (m, 1H); 3.16-3.21 (m, 1H); 3.35-3.43 (m, 1H); 3.51-3.61 (m, 1H); 4.61 (q, 1H, J=5.2 Hz); 7.09-7.38 (m, 10H).

b) (-4-(dimethylamino)-4-phenyl-1-(4-phenylbutyl)cyclohexyl)methanol (Polar Diastereoisomer)

A solution of the title compound of the previous step (622 mg, 1.42 mmol) in tetrahydrofuran (5 mL) was mixed with glacial acetic acid (3.0 mL) and water (1.5 mL) and firstly stirred with reflux for 8 h. Since the reaction was not yet complete, the mixture was stirred overnight at 50° C. and then once again for 8 h with reflux. Although the conversion was still not quite complete, the reaction solution was concentrated to low volume in a vacuum and the residue taken up multiple times in toluol (3×10 mL) and each time concentrated again to low volume in a vacuum. The residue was taken up in 5% sodium hydrogencarbonate solution (30 mL) and extracted with ethyl acetate (3×20 mL). The combined organic phases were washed with saturated sodium chloride solution (30 mL), dried with sodium sulphate and concentrated to low volume in a vacuum. Since the raw product still contained starting substance, this was separated by means of flash chromatography (400 g, 20×7.5 cm) with ethyl acetate/methanol (4:1) (77 mg). Only 245 mg of the very polar target compound were obtained at first. Further product (220 mg) was isolated by washing the column with methanol (500 mL).

Yield: 465 mg (86%), white solid
Melting point: 123° C.
1H-NMR (DMSO-d6): 0.90-1.03 (m, 2H); 1.11 (br s, 4H); 1.35-1.53 (m, 4H); 1.92 (br s, 10H); 2.47 (d, 2H, J=8.2 Hz); 3.25 (d, 2H, J=4.9 Hz); 4.35 (t, 1H, J=4.7 Hz); 7.09-7.15 (m, 3H); 7.18-7.24 (m, 3H); 7.28-7.39 (m, 4H).
13C-NMR (DMSO-d6): 22.3; 28.1; 28.2; 35.2; 35.7; 37.6; 38.9; 59.9; 65.3; 125.4; 126.1; 127.4; 128.0; 128.1; 142.3.

Example 22

[4-benzyl-4-(dimethylaminomethyl)-1-phenyl-cyclohexyl]-dimethylamine

Step 1:

4-benzyl-1-(dimethylamino)-4-((dimethylamino)methyl)cyclohexane carbonitrile

40% aqueous dimethylamine solution (2.8 mL, 22.1 mmol), 4-benzyl-4-((dimethylamino)methyl)cyclohexanone (1.13 g, 4.60 mmol) and potassium cyanide (0.70 g, 11.0 mmol) were added to a mixture of 4N hydrochloric acid (3 mL) and methanol (1.05 mL) with ice cooling. The mixture was stirred for 2 d at room temperature and then after adding water (200 mL) was extracted with ether (4×150 mL). After the solution was concentrated, the residue was taken up in dichloromethane (200 mL) and dried overnight with magnesium sulphate, filtered and the solvent was removed in a vacuum. The nitrile was obtained as an oil which was crystallised through.

Yield: 1.06 g (77%)
$^1$H-NMR (DMSO-d$_6$): 1.23 (2 H, m); 1.74 (2 H, m); 2.16 (6 H, s); 2.24 (6 H, s); 2.32 (2 H, m); 2.68 (2 H, s); 7.16 (5 H, m).

Step 2:

[4-benzyl-4-(dimethylaminomethyl)-1-phenyl-cyclohexyl]-dimethylamine

The title compound of step 1 (0.88 g, 2.94 mmol) was dissolved in THF (35 mL) and mixed in drops with 2M phenylmagnesium chloride solution (5.1 mL, 10.2 mmol) with ice cooling. The reaction solution was heated to boiling for 8 h. For work up the solution was mixed with 20% NH$_4$Cl solution (0.6 mL) and water (0.4 mL) with ice cooling, extracted with ether (3×25 mL), the ether solution was washed with water, dried (Na$_2$SO$_4$) and concentrated to low volume in a vacuum. The residue was purified by column chromatography with EtOH/EE (1:20). 2 fractions were obtained, wherein according to LCMS, inter alia, the more polar fraction (300 mg) contained the desired substance.

Yield: 90 mg (9%)
$^1$H-NMR (DMSO-d$_6$): 1.23 (4 H, m); 1.39 (2 H, m); 1.82 (2H, s); 1.89 (6 H, s); 2.09 (6 H, s); 2.10 (2 H, m); 2.73 (2 H, s); 7.25 (10 H, m).

Example 23

(4-dimethylamino-1,4-diphenyl-cyclohexyl)-methyl-dimethylamine

Step 1:

5-cyano-2-oxo-5-phenyl-cyclohexane carboxylic acid ethyl ester

NaNH$_2$ (100 g, 2560 mmol) was added in portions to a solution of benzyl cyanide (35.6 g, 304 mmol) and bromopropionic acid ethyl ester (126 g, 694 mmol) in dry toluol (1070 mL) with stirring over 3 h at 0 to 5° C. The mixture was then heated to boiling for 6 h (the reaction was firstly exothermic and therefore the heating bath had to be removed intermittently). The mixture was then cooled to 0° C. and quenched with a mixture of acetic acid (240 mL) and water (120 mL). The toluol phase was separated, the aqueous phase extracted with toluol (2×200 mL) and the combined organic phase washed with NaHCO$_3$ solution (2×200 mL) and water (2×200 mL) and dried with Na$_2$SO$_4$. The solvent was then removed in a vacuum.

Yield: 70.8 mg (86%), brown solid
$^1$H-NMR (DMSO-d$_6$): 1.25 (3 H, t); 2.24-2.88 (6 H, m); 4.19 (2 H, q); 7.50 (5 H, m).

Step 2:

4-oxo-1-phenyl-cyclohexane carbonitrile

The title compound of step 1 (70.8 g, 261 mmol) in a mixture of acetic acid (810 mL) and concentrated hydrochloric acid (354 mL) was heated to boiling for 3.5 h under DC control. The mixture was then cooled to 0 to 5° C., diluted with water (1 L), saturated with NaCl and extracted cold with ethyl acetate (3×300 mL). The ethyl acetate phase was washed with water and concentrated to low volume in a vacuum. The solid residue was dissolved once again in ethyl acetate, washed with NaHCO$_3$ solution and concentrated until dry.

Yield 43.3 g (83%), yellow solid
The residue was used for the conversion with ethylene glycol without further purification
$^1$H-NMR (DMSO-d$_6$): 2.41 (6 H, m); 2.71 (2 H, m); 7.40 (3 H, m); 7.60 (2 H, m).
$^{13}$C-NMR (DMSO-d$_6$): 35.3; 38.1; 42.3; 121.7; 125.6; 128.2; 129.0; 139.2; 206.7.

Step 3:

8-phenyl-1,4-dioxa-spiro[4.5]decane-8-carbonitrile

The title compound of step 2 (43.3 g, 217 mmol) and ethylene glycol (27.4 g, 435 mmol) were boiled in toluol (430 mL) with the addition of p-toluol sulphonic acid (1.87 g, 10.9 mmol) at a water separator for 3 h with reflux. After the reaction had ended, the mixture was cooled, washed with NaHCO$_3$ solution and saturated NaCl solution, dried with Na$_2$SO$_4$ and concentrated to low volume in a vacuum.

Yield: 48.8 g (96%), solid
$^1$H-NMR (DMSO-d$_6$): 1.85 (4 H, m); 2.13 (4 H, m); 3.92 (4 H, s); 7.44 (5 H, m).
$^{13}$C-NMR (DMSO-d$_6$): 32.1; 34.0; 42.5; 63.8; 106.1; 122.1; 125.5; 128.0; 128.9; 139.9.

Step 4:

C-(8-phenyl-1,4-dioxa-spiro[4.5]dec-8-yl)-methylamine

A solution of the title compound of step 3 (10.0 g, 41.1 mmol) in dry THF (70 mL) was slowly added to a mixture of LiAlH$_4$ (1.87 g, 49.3 mmol) in dry THF (25 mL) in a protective gas. The mixture was then stirred for 3 h with reflux. After the reaction mixture had cooled, a solution of water (1.87 mL, 104 mmol) diluted with a little THF was added in drops with ice cooling and subsequently stirred for 10 min. 15% aqueous NaOH (1.87 mL, 8.17 mmol) diluted with a little THF was then added in drops and water (5.6 mL) was then added again. The precipitate formed was filtered over diatomaceous earth and the solvent removed in a vacuum. The amine remained as residue.

Yield: 7.96 g, (78%), yellow oil $^{13}$C-NMR (DMSO-d$_6$): 29.9; 31.0; 42.7; 53.9; 63.5; 108.3; 125.5; 126.8; 128.2; 143.8.

Step 5:

Dimethyl-(8-phenyl-1,4-dioxa-spiro[4.5]dec-8-ylmethyl)-amine

The title compound of step 4 (5.40 g, 21.8 mmol) was dissolved in acetonitrile (150 mL), and a cloudy solution was formed. Aqueous 37% formalin solution (30.6 mL, 407 mmol) was added. The batch was stirred for 20 min at RT and then mixed with sodium cyanoboron hydride (5.76 g, 91.7 mmol). The reaction was followed by DC in chloroform/methanol (9:1). After 4 h the solution was adjusted to pH 7 with acetic acid and concentrated to low volume in a vacuum. The residue was taken up in chloroform, washed with NaHCO$_3$ solution and the aqueous phase extracted with ether. The combined organic phases were dried over Na$_2$SO$_4$ and concentrated to low volume in a vacuum. The raw product was purified by flash chromatography with chloroform/methanol (50:1→20:1→9:1).

Yield: 5.40 g (67%)

$^1$H-NMR (DMSO-d$_6$): 1.32 (2 H, m); 1.56 (2 H, m); 1.77 (2 H, m); 1.91 (6 H, s); 2.14 (2 H, m); 2.28 (2 H, s); 3.80 (4 H, m); 7.16-7.39 (5 H, m).

Step 6:

4-dimethylaminomethyl-4-phenylcyclohexanone

The title compound of step 5 (5.40 g, 19.6 mmol) was dissolved in 5% H$_2$SO$_4$ (300 mL) and stirred for 1 d at RT. The solution was then washed with ether three times and the ether phase discarded. The aqueous phase was made alkaline with 5N NaOH with ice cooling and extracted with dichloromethane three times. The organic phase was washed with a little water, dried over Na$_2$SO$_4$ and concentrated to low volume in a vacuum.

Yield: 4.89 g (100%)

$^1$H-NMR (DMSO-d$_6$): 1.92 (6 H, s); 1.94-2.00 (2 H, m); 2.07-2.25 (4 H, m); 2.39-2.46 (4 H, m); 7.23 (1 H, m); 7.37 (2 H, m); 7.48 (2 H, m).

Step 7:

1-dimethylamino-4-dimethylaminomethyl-4-phenyl-cyclohexane carbonitrile

40% aqueous dimethylamine solution (12.8 mL, 21.1 mmol) was added in drops to a mixture of 4N hydrochloric acid (5 mL) and methanol (3 mL) with ice cooling. The title compound of step 6 (4.89 g, 21.1 mmol) and KCN (3.30 g, 50.7 mmol) were then added one after the other. The mixture was stirred for 3 d at RT. For work up the batch was mixed with water (10 mL) and extracted with diethyl ether (3×20 mL). The ether phase was concentrated to low volume in a vacuum, the residue was taken up in CH$_2$Cl$_2$, dried over Na$_2$SO$_4$ and concentrated to low volume in a vacuum.

Yield: 5.16 g (86%)

$^1$H-NMR (DMSO-d$_6$): 1.28 (2 H, m); 1.69 (2 H, m); 1.94 (6 H, s); 2.05 (2 H, m); 2.15 (6 H, s); 2.26 (2 H, m); 2.37 (2 H, s); 7.19 (1 H, m); 7.35 (4 H, m).

Step 8:

(4-dimethylaminomethyl-1,4-diphenyl-cyclohexyl)-dimethylamine 2M phenylmagnesium chloride solution in THF (3.5 mL, 7.0 mmol) was slowly added in drops to a solution of the title compound of step 7 (1.00 g, 3.5 mmol) in abs. THF (10 mL) in a nitrogen atmosphere and with ice cooling at 10° C. The solution was stirred for 20 h at RT. Then 20% NH$_4$Cl solution (5 mL) and water (2 mL) were added and the solution was extracted with ether (3×5 mL). The combined organic phases were washed with water (2 mL) and saturated NaCl solution (2 mL), dried over Na$_2$SO$_4$ and concentrated to low volume in a vacuum. By flash chromatography of the residue with chloroform/methanol (20:1) a salt of the product was obtained that was released with 1N NaOH, extracted with chloroform, dried over Na$_2$SO$_4$, and the solvent removed from it in a vacuum.

Yield: 336 mg (28%) non-polar diastereoisomer, porous solid $^1$H-NMR (CDCl$_3$): 1.39 (2 H, m); 1.65-1.78 (2 H, m); 1.82 (6 H, s); 1.96 (6 H, s); 2.20 (2 H, s); 2.28-2.41 (4 H, m); 7.15-7.44 (10 H, m).

Example 24

(E)-N-(4-dimethylamino-1,4-diphenyl-cyclohexyl)-N-methyl-3-phenyl-acrylamide (Non-polar Diastereomer)

The title compound from Example 8 (202 mg, 0.656 mmol) was provided in dry THF (20 mL) and mixed with TEA (97 μL, 0.702 mmol). Cinnamic acid chloride (116 mg, 0.702 mmol) was then added. The batch was stirred for 20 h at room temperature. After this reaction time the batch was concentrated until dry in a vacuum. The residue was taken up in ethyl acetate (20 mL) and washed with saturated NaHCO$_3$ solution (2×20 mL) and saturated NaCl solution (2×20 mL). The organic phase was dried over Na$_2$SO$_4$ and concentrated to low volume in a vacuum. The residue was purified by flash chromatography with chloroform/methanol (20:1).

Yield: 95 mg (33%)

$^1$H-NMR (DMSO-d$_6$): 1.61 (2 H, bs); 1.97 (5 H, bs); 2.45 (1 H, m); 2.49 (4 H, m); 2.94 (3 H, bs); 3.23 (1 H, s); 3.35 (1 H, s); 3.35 (2 H, m); 7.02 (1 H, m); 7.25 (2 H, m); 7.34 (9 H, m); 7.46 (2 H, m); 7.57 (2 H, m).

Example 33

(4-benzyl-4-((dimethylamino)methyl)-N-methyl-1-phenylcyclohexanamine (Polar Diastereomer)

Step 1:

4-benzyl-4-dimethylaminomethyl-1-methylamino-cyclohexane carbonitrile

40% aqueous methylamine solution (15.3 mL, 121 mmol) and 4-benzyl-4-((dimethylamino)methyl)cyclohexanone (6.20 g, 25.3 mmol) dissolved in methanol (25 mL) were added to a solution of 4N hydrochloric acid (6.6 mL) and methanol (4.00 mL) cooled to 0° C. The reaction mixture was then mixed with potassium cyanide (4.00 g, 60 mmol) and stirred for 5 d at room temperature. For work up the mixture was diluted with water (180 mL) and extracted with ether (3×100 mL). The combined organic phases were dried over $Na_2SO_4$, filtered and concentrated until dry in a vacuum.

Yield: 5.80 g (81%)

$^1$H-NMR (DMSO-$d_6$): 1.35 (5 H, m); 1.58 (8 H, m); 2.25 (6 H, m); 2.65 (4 H, m); 4.35 (1 H, m); 7.14 (3 H, m); 7.28 (2 H, m).

Step 2:

(4-benzyl-4-((dimethylamino)methyl)-N-methyl-1-phenylcyclohexanamine (Polar Diastereomer)

Phenyl lithium (33 mL, 60 mmol, 1.8 M solution in dibutyl ether) was mixed in drops with a solution of the title compound from step 1 (5.70 g, 20 mmol) in diethyl ether (60 mL) in argon and at room temperature. During this, the temperature of the reaction solution rose to 35° C. and a solid separated out. The reaction mixture was stirred with reflux for 30 min, then hydrolysed in an ice bath with 20% $NH_4Cl$ solution (40 mL) and the organic phase was separated. The aqueous phase was extracted with ether (3×100 mL). The combined organic phases were dried over $Na_2SO_4$, filtered and concentrated to low volume in a vacuum. The residue was purified by flash chromatography with chloroform/methanol (20:1→9:1→1:1→1% TEA). The polar diastereomer was obtained in clean form. The non-polar diastereomer was isolated in impure state.

Yield: 1.40 g (21%), polar diastereomer $^1$H-NMR (DMSO-$d_6$): 1.13 (2 H, m); 1.74 (4 H, m); 1.89 (3 H, m); 1.96 (4 H, m); 2.23 (6 H, s); 2.68 (2 H, s); 7.15 (4 H, m); 7.26 (2 H, m); 7.33 (2 H, m); 7.48 (2 H, m).

Example 34

(1-benzyl-4-dimethylamino-4-phenyl-cyclohexyl)-methyl-dimethylamine (Polar Diastereomer)

A solution of the title compound from Example 33 (1.40 g, 4.16 mmol) and formalin (5.8 mL, 37% aqueous solution) in acetonitrile (40 mL) was mixed in portions with sodium cyanoboron hydride (1.03 g, 16.6 mmol) and stirred for 45 min at room temperature. Concentrated acetic acid was then added until a neutral reaction occurred and the mixture stirred for 45 min at room temperature. For work up the solvent was removed in a vacuum, the residue taken up in 2N NaOH (40 mL) and then extracted with ether (3×40 mL). The organic phase was dried over $Na_2SO_4$, filtered and concentrated to low volume in a vacuum. The remaining residue was purified by flash chromatography with ethyl acetate (methanol→methanol+2% TEA).

Yield: 200 mg (14%)

$^1$H-NMR (DMSO-$d_6$): 1.10 (2 H, m); 1.56 (2 H, m); 1.89 (6 H, s); 2.00 (2 H, m); 2.04 (2 H, s); 2.11 (2 H, m); 2.25 (6 H, s); 2.58 (2 H, m); 7.19 (10 H, m).

Example 37

[4-(dimethylaminomethyl)-1,4-diphenyl-cyclohexyl]-dimethylamine (Polar Diastereomer)

2M phenylmagnesium chloride solution in THF (3.5 mL, 7.0 mmol) was slowly added in drops to a solution of the title compound of Example 23, step 7 (1.00 g, 3.5 mmol) in abs. THF (10 mL) in a nitrogen atmosphere and with ice cooling at 0-10° C. The solution was stirred for 20 h at RT. 20% $NH_4Cl$ solution (5 mL) and water (2 mL) were then added and the solution extracted with ether (3×5 mL). The combined organic phases were washed with water (2 mL) and saturated NaCl solution (2 mL), dried over $Na_2SO_4$, filtered and concentrated to low volume in a vacuum. Flash chromatography with chloroform/methanol (20:1→9:1→4:1→1:1→1:1+1% $NH_3$→MeOH+1% $NH_3$) gave the hydrochloride of the non-polar diastereoisomer at 20:1, and this was released with 1N NaOH, extracted with chloroform, dried over $Na_2SO_4$ and concentrated to low volume in a vacuum. The polar diastereoisomer was obtained with MeOH+1% $NH_3$. Since the first spectrum also indicated a salt here, the polar diastereoisomer was also released with 1N NaOH, extracted with chloroform, dried over $Na_2SO_4$ and concentrated to low volume in a vacuum.

Yield: 81 mg (7%), polar diastereoisomer, porous solid $^1$H-NMR (DMSO-$d_6$): 1.59 (2 H, breit); 1.77-1.86 (2 H, m); 1.89 (6 H, s); 1.95 (6 H, s); 1.97-2.05 (2 H, m); 2.25 (2 H, m); 2.39 (2 H, s); 7.07-7.37 (10 H, m).

Example 42

(E)-N-[[4-dimethylamino-4-(3-fluorophenyl)-1-methyl-cyclohexyl]-methyl]-3-phenyl-acrylamide (Polar Diastereomer)

Step 1:

4-dimethylamino-4-(3-fluorophenyl)-cyclohexane carbaldehyde

KOtBu (2.15 g, 19.2 mmol) dissolved in abs. THF (25 mL) was added in drops to a solution of (methoxymethyl)triphenylphosphonium chloride (6.58 g, 19.2 mmol) in abs. THF (25 mL) at 0° C. in argon. The resulting red solution was mixed after 30 min at 0° C. with a solution of 4-dimethylamino-4-(3-fluorophenyl)cyclohexanone (3.0 g, 12.76 mmol) in abs. THF (25 mL) and stirred overnight at RT. The solvent was removed in a vacuum, the residue mixed with 1M sulphuric acid (50 mL) and stirred for 2 h. The precipitate precipitated out during this was separated and the filtrate (pH 1) washed with ether (6×30 mL). The aqueous solution was adjusted to pH 11 with 5N NaOH and extracted with ethyl acetate (3×50 mL). The combined organic phases were dried over $Na_2SO_4$ and concentrated to low volume in a vacuum.

Yield: 3.20 g (100%), brown oil

Diastereomer mixture 1:1

$^1$H-NMR (DMSO-$d_6$): 1.20 (1 H, m); 1.62 (2 H, m); 1.75 (3 H, m); 1.93 (6 H, s); 2.37 (3 H, m); 7.12 (3 H, m); 7.40 (1 H, m); 9.50 (0.5 H, s); 9.62 (0.5; H, s).

Step 2:

4-dimethylamino-4-(3-fluorophenyl)-1-methyl-cyclohexane carbaldehyde

A solution of the title compound of step 1 (2.73 g, 10.95 mmol) in abs. dichloromethane (50 mL) was mixed with tert-BuOK (1.47 g, 13.14 mmol) and methyl iodide (747 µl, 12 mmol) at 0° C. in argon. After 30 min the batch was heated to RT and then stirred overnight (solid separated out). The reaction mixture was mixed with saturated NaCl solution (50 mL) and extracted with dichloromethane (3×30 mL). The combined organic phases were dried over $Na_2SO_4$, concentrated to low volume in a vacuum and the remaining residue was purified by flash chromatography with ethyl acetate/MeOH 20:1.

Yield: 1.39 g (51%)

¹H-NMR (DMSO-d₆): 0.85 (1.5 H, s); 1.00 (1.5 H, s); 1.50 (1H, m); 1.54-1.77 (4 H, m); 1.89-1.95 (7 H, m); 2.11-2.31 (2 H, m); 7.11 (3 H, m); 7.38 (1 H, m); 9.36 (0.5 H, s); 9.44 (0.5 H, s).

Step 3:

4-dimethylamino-4-(3-fluorophenyl)-1-methyl-cyclohexane carbaldehyde oxime

A solution of the title compound of step 2 (1.38 g, 5.53 mmol) and hydroxylamine hydrochloride (576 mg, 8.3 mmol) in abs. ethanol (20 mL) were mixed with Amberlyst A 21 (3.9 g) and stirred for 16 h at RT. The ion exchanger was filtered off, the solution concentrated to low volume and the residue made alkaline with 1N NaOH. The aqueous phase was extracted with ethyl acetate, dried over Na₂SO₄ and concentrated to low volume in a vacuum.

Yield: 1.54 g (100%)

Step 4:

[4-aminomethyl-1-(3-fluorophenyl)-4-methyl-cyclohexyl]-dimethylamine

Lithium aluminium hydride (440 mg, 11.6 mmol) was suspended in abs. THF (50 mL) in argon, mixed in drops with a solution of the title compound of step 3 (1.54 g, 5.53 mmol) in abs. THF (20 mL) and boiled for 4 h with reflux. The batch was then hydrolysed with water (10 mL) at 10° C. and filtered off over diatomaceous earth. The THF was removed in a vacuum, the residue adjusted to pH 11 with 1N NaOH and extracted with ethyl acetate. The combined organic phases were dried over Na₂SO₄, concentrated to low volume in a vacuum and the remaining residue was purified by flash chromatography with MeOH+2% NH₃.

Yield: 435 mg (30%, non-polar diastereomer)

¹H-NMR (DMSO-d₆): 0.85 (3 H, s); 1.03 (2 H, m); 1.29 (2 H, m); 1.83 (2 H, m); 1.91 (6 H, s); 2.08 (2 H, m); 2.17 (2 H, s); 7.09 (3 H, m); 7.38 (1 H, m).

Yield: 510 mg (35%, polar diastereomer)

¹H-NMR (DMSO-d₆): 0.72 (3 H, s); 1.00 (2 H, m); 1.49 (2 H, m); 1.78 (2 H, m); 1.91 (6 H, s); 2.07 (2 H, m); 2.38 (2 H, s); 7.09 (3 H, m); 7.39 (1 H, m).

Step 5:

(E)-N-[[4-dimethylamino-4-(3-fluorophenyl)-1-methyl-cyclohexyl]-methyl]-3-phenyl-acrylamide (Polar Diastereomer)

A solution of the title compound of step 4 (polar diastereomer) (250 mg, 0.94 mmol) and Hünig's base (169 µl, 1.0 mmol) in abs. dichloromethane (10 mL) was mixed with cinnamic acid chloride (166 mg 1.0 mmol) and stirred for 24 h at RT. The organic solution was washed with saturated NaHCO₃ solution and saturated NaCl solution, dried over Na₂SO₄, concentrated to low volume in a vacuum and the remaining residue was purified by flash chromatography with ethyl acetate/MeOH 4:1.

Yield: 295 mg (80%), porous solid

¹H-NMR (DMSO-d₆): 0.77 (3 H, s); 1.03 (2 H, m); 1.53 (2 H, m); 1.87 (2 H, m); 1.93 (6 H, s); 2.12 (2 H, m); 3.17 (2 H, d); 6.76 (1 H, d); 7.07 (3 H, m); 7.37 (5 H, m); 7.56 (2 H, m); 7.96 (1 H, t).

Example 48

[4-(butyl-methyl-amino)-1,4-diphenyl-cyclohexyl]-dimethylamine (Non-polar Diastereomer)

Step 1:

N-(4-dimethylamino-1,4-diphenyl-cyclohexyl)-N-methyl-butyramide

The title compound from Example 8 (308 mg, 1.0 mmol) was provided in abs. THF (15 mL) and mixed with TEA (165 µL, 1.2 mmol) and butyryl chloride (103 mg, 1.2 mmol, V=124 µL). The batch was stirred for 20 h at room temperature and then concentrated until dry in a vacuum. The residue was taken up in ethyl acetate (20 mL) and washed with saturated NaHCO₃ solution (2×20 mL) and saturated NaCl solution (2×20 mL). The organic phase was dried over Na₂SO₄ and concentrated to low volume in a vacuum. The residue was purified by flash chromatography with chloroform/methanol (50:1).

Yield: 206 mg (53%)

¹H-NMR (DMSO-d₆): 0.76 (3 H, t); 1.41 (2 H, q); 1.60 (2 H, m); 1.95 (6 H, s); 2.22 (4 H, t); 2.33 (2 H, m); 2.82 (3 H, s); 7.20-7.39 (10 H, m).

Step 2:

[4-(butyl-methyl-amino)-1,4-diphenyl-cyclohexyl]-dimethylamine (Non-polar Diastereomer)

The title compound from step 1 (200 mg, 0.528 mmol) was dissolved in abs. THF (15 mL). LiAlH₄ (39 mg, 1.06 mmol) was added in argon. The batch was boiled for 7 h with reflux. The batch was then cooled to room temperature, mixed with THF (12 mL) and H₂O (5 mL) with ice cooling and subsequently stirred for 30 min. The batch was filtered over a fritted glass filter with diatomaceous earth and subsequently rinsed with dichloromethane (50 mL). The combined filtrates were concentrated to low volume in a vacuum.

Yield: 194 mg (100%), oil

¹H-NMR (DMSO-d₆): 0.74 (3 H, t); 1.12 (4 H, m); 1.73 (4 H, wide); 1.83 (6 H, s); 1.90 (3 H, s); 1.92 (1 H, s); 1.96 (2 H, wide); 2.25 (4 H, wide); 7.25 (2 H, m); 7.38 (8 H, m).

Example 49

[4-(butyl-methyl-amino)-1,4-diphenyl-cyclohexyl]-dimethylamine (Polar Diastereomer)

The title compound from Example 9 (308 mg, 1.0 mmol) and butyric aldehyde (72 mg, 1.0 mmol, V=89 µL) were provided in abs. acetonitrile (30 mL) and mixed with sodium cyanoboron hydride (250 mg, 4.0 mmol). The batch was stirred for 45 min at room temperature, then mixed with conc. acetic acid (approx. 500 µL) and stirred a further 45 min at room temperature. For work up the batch was concentrated until dry in a vacuum. The residue was mixed with 2N NaOH and extracted with ether (3×20 mL). The combined organic phases were dried over Na₂SO₄ and concentrated to low volume in a vacuum. The residue was purified by flash chromatography with chloroform/methanol (9:1).

Yield: 111 mg (30%), oil

¹H-NMR (DMSO-d₆): 0.86 (3 H, t); 1.30 (6 H, m); 2.05 (12 H, m); 2.35 (5 H, m); 7.29 (10 H, m).

Example 50

[40-(benzyl-methyl-amino)-1,4-diphenyl-cyclohexyl]-dimethylamine (Non-polar Diastereomer)

Step 1:

N-(4-dimethylamino-1,4-diphenyl-cyclohexyl)-N-methyl-benzamide

The title compound from Example 8 (308 mg, 1.0 mmol) was provided in abs. THF (15 mL) and mixed with TEA (165 µL, 1.2 mmol) and benzoyl chloride (168 mg, 1.2 mmol, V=147 µL). The batch was stirred for 16 h at room temperature and then concentrated until dry in a vacuum. The residue was taken up in ethyl acetate (20 mL), washed with saturated $NaHCO_3$ solution (2×20 mL) and saturated NaCl solution (2×20 mL). The organic phase was dried over $Na_2SO_4$ and concentrated to low volume in a vacuum. The residue was purified by flash chromatography with chloroform/methanol (20:1).

Yield: 169 mg (41%)

$^1$H-NMR (DMSO-$d_6$): 1.75 (2H, m); 1.98 (6H, s); 2.38 (3H, m); 2.55 (2H, m); 2.69 (4H, s); 7.24-7.41 (13H, m); 7.54 (2H, d).

Step 2:

[4-(benzyl-methyl-amino)-1,4-diphenyl-cyclohexyl]-dimethylamine (Non-polar Diastereomer)

The title compound from step 1 (160 mg, 0.387 mmol) was dissolved in abs. THF (15 mL) and mixed with $LiAlH_4$ (29 mg, 0.775 mmol) in argon. The batch was boiled for 7 h with reflux and then cooled to room temperature. THF (5 mL) and $H_2O$ (5 mL) were added to the batch with ice cooling and subsequently stirred for 30 min. The batch was filtered over a fritted glass filter with diatomaceous earth and subsequently rinsed with dichloromethane (50 mL). The combined filtrates were concentrated to low volume in vacuum.

Yield: 149 mg (97%)

$^1$H-NMR (DMSO-$d_6$): 1.78 (3 H, s); 1.85 (10 H, s); 2.33 (4 H, m); 3.14 (2 H, bs); 7.04-7.20 (4 H, m); 7.31 (2 H, m); 7.40 (9 H, m).

Example 51

[4-(benzyl-methyl-amino)-1,4-diphenyl-cyclohexyl]-dimethylamine (Polar Diastereomer)

Step 1:

N-(4-dimethylamino-1,4-diphenyl-cyclohexyl)-N-methyl-benzamide

The title compound from Example 9 (308 mg, 1.0 mmol) was provided in abs. THF (15 mL) and mixed with TEA (165 µL, 1.2 mmol) and benzoyl chloride (168 mg, 1.2 mmol, V=147 up. The batch was stirred for 16 h at room temperature and then concentrated until dry in a vacuum. The residue was taken up in ethyl acetate (20 mL), washed with saturated $NaHCO_3$ solution (2×20 mL) and saturated NaCl solution (2×20 mL). The organic phase was dried over $Na_2SO_4$ and concentrated to low volume in a vacuum. The residue was purified by flash chromatography with chloroform/methanol (20:1).

Yield: 304 mg (74%)

$^1$H-NMR (DMSO-$d_6$): 1.63 (2 H, m); 1.92-2.00 (10 H, m); 2.52 (1 H, m); 2.76 (3 H, s); 7.16 (1 H, m); 7.28 (4 H, m); 7.39-7.49 (10 H, m).

Step 2:

[4-(benzyl-methyl-amino)-1,4-diphenyl-cyclohexyl]-dimethylamine (Polar Diastereomer)

The title compound from step 1 (290 mg, 0.702 mmol) was dissolved in abs. THF (15 mL) and mixed with $LiAlH_4$ (52 mg, 1.40 mmol) in argon. The batch was boiled for 7 h with reflux and then cooled to room temperature. The batch was filtered over a fritted glass filter with diatomaceous earth and subsequently rinsed with dichloromethane (50 mL). The combined filtrates were concentrated to low volume in vacuum.

Yield: 250 mg (89%)

$^1$H-NMR (DMSO-$d_6$): 1.43 (1 H, m); 1.72-1.76 (1 H, m); 1.89 (3 H, s); 1.99 (6 H, s); 2.42 (3H, wide); 3.25 (2 H, bs); 7.16-7.39 (15 H, m).

Example 66

2-[(4-dimethylamino-1,4-diphenyl-cyclohexyl)-methyl-amino]acetic acid (Polar Diastereomer)

Step 1:

[(4-dimethylamino-1,4-diphenyl-cyclohexyl)-methyl-amino]acetic acid tert-butyl ester A solution of the title compound from Example 9 (246 mg, 0.8 mmol) and bromoacetic acid tert-butyl ester (132 µl, 0.9 mmol) in abs. DMF (10 mL) was mixed with potassium carbonate (124 mg, 0.9 mmol) and stirred for 20 h at RT. The solvent was then removed in a vacuum, the residue dissolved in dichloromethane (20 mL), washed with water (2×10 mL) and saturated NaCl solution (2×10 mL) and dried over $Na_2SO_4$. The organic solution was concentrated to low volume in a vacuum and the remaining residue was purified by flash chromatography with chloroform/MeOH 20:1.

Yield: 133 mg (39%)

$^1$H-NMR (CDCl$_3$): 1.44 (9 H, s); 1.78 (2 H, bs); 1.95 (2 H, bs); 2.09 (6 H, s); 2.21 (3 H, s); 2.43 (4 H, m); 2.92 (2 H, s); 7.16-7.31 (10 H, m).

Step 2:

2-[(4-dimethylamino-1,4-diphenyl-cyclohexyl)-methyl-amino]acetic acid (Polar Diastereomer)

The title compound from step 1 (130 mg, 0.3 mmol) was dissolved in anisole (0.5 mL) and trifluoroacetic acid (2.5 mL) and stirred for 20 h at RT. The mixture was then concentrated until dry in a vacuum, 1N NaOH stirred through the solid residue, the solid filtered, washed with water and dried in a vacuum.

Yield: 69 mg (63%)

Melting point: 270-273° C.

$^1$H-NMR (DMSO-$d_6$): 1.70 (3 H, br); 1.96 (6 H, s); 2.00 (3 H, s); 2.25 (2 H, m); 2.45 (4 H, m); 3.32 (2 H, s); 7.14 (2 H, m); 7.25 (8 H, m).

The following compound was obtained following a specification such as described in Example 66 except that the educts listed in Table 1-1 were used.

TABLE 1-1

| Ex. No. | Educt | Product | Cy (%)/MS (m/z) |
|---|---|---|---|
| 67 | Ex. 8 | 2-[(4-dimethylamino-1,4-diphenyl-cyclohexyl)-methylamino]acetic acid (non-polar diastereomer) | 63 (367) |

Example 68

[1-(4-methoxyphenyl)-4-methylamino-4-phenyl-cyclohexyl]-dimethylamine (Non-polar Diastereomer)

Step 1:

[8-(4-methoxy-phenyl)-1,4-dioxa-spiro[4.5]dec-8-yl]-dimethylamine

Magnesium (3.65 g, 150 mmol) and an iodine crystal were provided in a nitrogen atmosphere and heated. Abs. ether (10 mL) was then added and a solution of 4-bromoanisole (18.8 mL, 150 mmol) in abs. ether (150 mL) was added in drops so that the ether lightly boiled. The solution formed was subsequently stirred for 1 h at RT and then mixed in drops with a solution of 8-dimethylamino-1,4-dioxa-spiro[4.5]decane-8-carbonitrile (10.5 g, 50.0 mmol) in abs. THF (100 mL), and the solution heated to 37-40° C. until boiling during the addition. A precipitate separated out and the batch was stirred overnight at RT. The solution was mixed with NH₄Cl solution with ice cooling, the phases were separated, the aqueous phase extracted three times with ether, the combined organic phases washed with saturated NaCl solution and water, dried over Na₂SO₄ and concentrated to low volume in a vacuum. Flash chromatography of the residue with ethyl acetate/methanol (20:1→9:1→4:1→1:4→MeOH) gave the desired product.

Yield: 6.80 g (47%)

Step 2:

4-dimethylamino-4-(4-methoxy-phenyl)-cyclohexanone

The title compound from step 1 (6.80 g, 23 mmol) was dissolved in ether (100 mL), mixed with 5% H₂SO₄ (100 mL) and the solution vigorously stirred for 2 d at RT. The phases were separated and the ether phase discarded. The aqueous phase was made alkaline with 5N NaOH with ice cooling and extracted three times with ether, the combined organic phases were then washed with water, dried over Na₂SO₄ and concentrated to low volume in a vacuum.

Yield: 4.20 g (73%)

¹H-NMR (DMSO-d₆): 2.00 (6 H, s); 2.01-2.14 (4 H, m); 2.42-2.48 (2 H, m); 2.53-2.63 (2 H, m); 3.76 (3 H, s); 6.93 (2 H, d); 7.34 (2 H, d).

Step 3:

4-dimethylamino-4-(4-methoxy-phenyl)-1-methyl-amino-cyclohexane carbonitrile

40% aqueous methylamine solution (3.50 mL, 40.1 mmol) was added in drops to a mixture of 4N hydrochloric acid (1.98 mL) and methanol (2.3 mL) with ice cooling. A solution of the title compound from step 2 (2.00 mg, 8.09 mmol) in methanol (30 mL) and potassium cyanide (1.32 g, 20.3 mmol) were then added. The mixture was stirred for 3 d at RT and then after adding water (10 mL) was extracted 4× with ether. The combined organic phases were dried over Na₂SO₄ and concentrated to low volume in a vacuum.

Yield: 2.23 g (96%), impure product, was converted further in raw state

¹H-NMR (DMSO-d₆): 1.29 (1 H, m); 1.61 (1 H, m); 1.69-1.86 (4 H, m); 1.90 (6 H, d); 1.93-2.04 (2 H, m); 2.28 (3 H, dd); 2.75 (1 H, dq); 3.75 (3H, d); 6.90 (2 H, d); 7.23 (2 H, dd).

Step 4:

[1-(4-methoxyphenyl)-4-methylamino-4-phenyl-cyclohexyl]-dimethylamine (Non-polar Diastereomer)

Phenyl lithium (12.9 mL, 23.3 mmol, 1.8 M solution in dibutyl ether) was provided in argon and mixed in drops with a solution of the title compound from step 3 (2.23 g, 7.76 mmol) in abs. diethyl ether (30 mL) at RT. During this, the reaction solution heated to 35° C. and a solid separated out. The reaction mixture was stirred for 1 h with reflux (bath 50° C.), then hydrolysed in the ice bath (0-10° C.) with 20% NH₄Cl solution (20 mL) and the organic phase was separated. The aqueous phase was extracted with ether (3×50 mL). The combined organic solutions were dried over Na₂SO₄ and concentrated to low volume in a vacuum. By means of flash chromatography (100 g silica gel) with ethyl acetate/methanol (20:1→9:1→MeOH→MeOH+2% NH₃) the non-polar diastereoisomer was obtained in a mixed fraction with starting substance and ketone and lastly the polar diastereoisomer. The mixed fraction with non-polar diastereoisomer was purified again by flash chromatography with dichloromethane/methanol (50:1→20:1→9:1→4:1).

Yield: 232 mg (9%), non-polar diastereoisomer

¹H-NMR (CDCl₃): 1.71 (2 H, m); 1.98 (4 H, m); 1.99 (6 H, s); 2.11 (1 H, m); 2.19-2.41 (5 H, m); 3.81 (3 H, s); 6.91 (2 H, m); 7.27 (3 H, m); 7.37 (2 H, m); 7.48 (2 H, m).

Example 69

[1-(4-methoxyphenyl)-4-methylamino-4-phenyl-cyclohexyl]-dimethylamine (Polar Diastereomer)

The polar diastereomer could also be isolated during the synthesis of the title compound from Example 68 as part of step 4.

Yield: 177 mg (7%), polar diastereoisomer

¹H-NMR (CDCl₃): 1.58-1.92 (4H, m); 2.03 (4 H, m); 2.07 (6 H, s); 2.10-2.18 (2 H, m); 2.29 (2 H, m); 3.80 (3 H, s); 6.87 (2 H, d); 7.14 (1 H, m); 7.20-7.33 (6 H, m).

The following compounds were obtained following a specification such as described in Examples 68 and 69 except that the bromides or corresponding Grignard reagents as well as the carbonitriles as listed in Table 1-2 were used.

TABLE 1-2

| Ex. No. | R-Br/MgX | Carbonitrile | Product | Cy (%)/MS (m/z) |
|---|---|---|---|---|
| 38 |  | (CN-A) | dimethyl-(4-methylamino-4-phenyl-1-thiophen-2-yl-cyclohexyl)-amine (non-polar diastereomer) | 20 (315) |
| 39 |  | (CN-A) | dimethyl-(4-methylamino-4-phenyl-1-thiophen-2-yl-cyclohexyl)-amine (polar diastereomer) | 33 (315) |

TABLE 1-2-continued

| Ex. No. | R-Br/MgX | Carbonitrile | Product | Cy (%)/MS (m/z) |
|---|---|---|---|---|
| 46 | | (CN-A) | (1-butyl-4-methylamino-4-phenyl-cyclohexyl)-dimethylamine (non-polar diastereomer) | 2 (289) |
| 47 | | (CN-A) | (1-butyl-4-methylamino-4-phenyl-cyclohexyl)-dimethylamine (polar diastereomer) | 28 (289) |
| 60 | | (CN-A) | [4-(cyclopentyl-methyl)-4-dimethylamino-1-phenyl-cyclohexyl]-methylamine (non-polar diastereomer) | 8 (315) |
| 61 | | (CN-A) | [4-(cyclopentyl-methyl)-4-dimethylamino-1-phenyl-cyclohexyl]-methylamine (polar diastereomer) | 36 (315) |
| 70 | | (CN-A) | dimethyl-[4-methylamino-4-phenyl-1-[4-(trifluoromethyl)-phenyl]-cyclohexyl]-amine (non-polar diastereomer) | 8 (377) |
| 71 | | (CN-A) | dimethyl-[4-methylamino-4-phenyl-1-[4-(trifluoromethyl)-phenyl]-cyclohexyl)-amine (polar diastereomer) | 7 (377) |
| 147 | | (CN-B) | (1,4-diphenyl-4-pyrrolidin-1-yl-cyclohexyl)-methylamine (polar diastereomer) | 8 (335) |
| 148 | | (CN-B) | (1,4-diphenyl-4-pyrrolidin-1-yl-cyclohexyl)-methylamine (non-polar diastereomer) | 3 (335) |

Carbonitriles:
8-dimethylamino-1,4-dioxaspiro[4.5]decane-8-carbonitrile (CN-A)
8-(pyrrolidin-1-yl)-1,4-dioxaspiro[4.5]decane-8-carbonitrile (CN-B)

Example 74

[4-dimethylamino-1-(4-methoxyphenyl)-4-phenyl-cyclohexyl]-dimethylamine (Polar Diastereomer)

A solution of the title compound from Example 69 (111 mg, 0.33 mmol) and formalin (0.45 mL, 37% aqueous solution) in acetonitrile (3 mL) was mixed with sodium cyanoboron hydride (83 mg, 1.32 mmol) and stirred for 45 min at RT. Conc. acetic acid was then added until a neutral reaction occurred and the mixture stirred for 45 min at RT. For work up the solvent was removed in a vacuum, the residue taken up with 2N NaCl (5 mL) and then extracted with ether (3×10 mL). The organic solution was dried over $Na_2SO_4$ and concentrated to low volume in a vacuum. The remaining residue was purified by means of flash chromatography with ethyl acetate/methanol (1:2-*MeOH).

Yield: 82 mg (71%)

$^1$H-NMR (CDCl$_3$): 1.62-2.05 (4 H, m); 2.07 (12 H, s); 2.37 (4 H, m); 3.79 (3 H, s); (6.77 (3H, s); 6.83 (2 H, d); 7.20 (3 H, m); 7.28 (4 H, m).

Example 75

[4-dimethylamino-1-(4-methoxyphenyl)-4-phenyl-cyclohexyl]-dimethylamine (Non-polar Diastereomer)

A solution of the title compound from Example 68 (96 mg, 0.28 mmol) and formalin (0.39 mL, 37% aqueous solution) in acetonitrile (3 mL) was mixed with sodium cyanoboron hydride (72 mg, 1.15 mmol) and stirred for 45 min at RT. Conc. acetic acid was then added until a neutral reaction occurred and the mixture stirred for 45 min at RT. For work up the solvent was removed in a vacuum, the residue taken up in 2N NaCl (5 mL) and then extracted with ether (3×10 mL). The organic solution was dried over $Na_2SO_4$ and concentrated to low volume in a vacuum. The remaining residue was purified by means of flash chromatography with ethyl acetate/methanol (2:1→1:1→1:1+2% $NH_3$).

Yield: 62 mg (62%)

$^1$H-NMR (CDCl$_3$): 1.59 (4 H, m); 1.92 (6 H, s); 1.93 (6 H, s); 2.48 (4 H, m); 3.81 (3 H, s); 6.90 (2 H, m); 7.20-7.41 (7 H, m).

The following compounds were obtained following a specification such as described in Examples 74 and 75 except that the educts listed in Table 1-3 were used.

TABLE 1-3

| Ex. No. | Educt (Ex. No.) | Product | Cy (%)/MS (m/z) |
|---|---|---|---|
| 40 | 39 | [4-(dimethylamino)-4-phenyl-1-thiophen-2-yl-cyclohexyl]-dimethylamine (polar diastereomer) | 73 (329) |
| 41 | 38 | (4-dimethylamino-4-phenyl-1-thiophen-2-yl-cyclohexyl)-dimethylamine (non-polar diastereomer) | 69 (329) |
| 58 | 46 | (4-butyl-4-dimethylamino-1-phenyl-cyclohexyl)-dimethylamine (non-polar diastereomer) | 27 (303) |
| 59 | 47 | (4-butyl-4-dimethylamino-1-phenyl-cyclohexyl)-dimethylamine (polar diastereomer) | 79 (303) |
| 62 | 60 | [4-(cyclopentyl-methyl)-4-dimethylamino-1-phenyl-cyclohexyl]-dimethylamine (non-polar diastereomer) | 51 (329) |

TABLE 1-3-continued

| Ex. No. | Educt (Ex. No.) | Product | Cy (%)/MS (m/z) |
|---|---|---|---|
| 63 | 61 | [4-(cyclopentyl-methyl)-4-dimethylamino-1-phenyl-cyclohexyl]-dimethylamine (polar diastereomer) | 86 (329) |
| 72 | 71 | [4-(dimethylamino)-4-phenyl-1-[4-(trifluoromethyl)-phenyl]-cyclohexyl]-dimethylamine (polar diastereomer) | 36 (391) |
| 73 | 70 | [4-dimethylamino-4-phenyl-1-[4-(trifluoromethyl)-phenyl]-cyclohexyl]-dimethylamine (non-polar diastereomer) | 68 (391) |
| 151 | 147 | (1,4-diphenyl-4-pyrrolidin-1-yl-cyclohexyl)-dimethylamine (polar diastereomer) | 34 (349) |
| 152 | 148 | (1,4-diphenyl-4-pyrrolidin-1-yl-cyclohexyl)-dimethylamine (non-polar diastereomer) | 45 (349) |

Example 76

[4-[(1H-indol-3-yl-methylamino)-methyl]-4-methyl-1-phenyl-cyclohexyl]-dimethylamine (Non-polar Diastereomer)

Step 1:

4-dimethylamino-4-phenyl-cyclohexane carbaldehyde

Tert-BuOK (8.41 g, 75 mmol) dissolved in abs. THF (100 mL) was added in drops to a solution of (methoxymethyl) triphenyl phosphonium chloride (25.7 g, 75.0 mmol) in abs. THF (100 mL) at 0° C. in argon. The resulting red solution was mixed after 30 min at 0° C. with a solution of 4-dimethylamino-4-phenyl cyclohexanone (10.9 g, 50.0 mmol) in abs. THF (100 mL) and stirred overnight at RT. The solvent was removed in a vacuum, the residue mixed with 1N sulphuric acid (150 mL) and stirred for 2 h. The precipitate precipitated out during this was separated and the filtrate (pH 1) washed with ether (6×100 mL). The aqueous solution was adjusted to pH 11 with 5N NaOH and extracted with ethyl acetate (3×100 mL). The combined organic phases were dried over $Na_2SO_4$ and concentrated to low volume in a vacuum.

Yield: 11.6 g (100%), brown oil
Diastereomer mixture 1:1
$^1$H-NMR (DMSO-$d_6$): 1.18 (1H, m); 1.59-1.91 (5H, m); 1.92 (6H, s); 2.36 (3H, m); 7.23-7.38 (5H, m); 9.48 (0.5H, s); 9.62 (0.5H, s).

Step 2:

4-dimethylamino-1-methyl-4-phenyl-cyclohexane carbaldehyde

A solution of the title compound from step 1 (11.6 g, 50.0 mmol) in abs. dichloromethane (200 mL) was mixed with tert-BuOK (6.50 g, 58.0 mmol) and methyl iodide (3.42 mL, 55.0 mmol) at 0° C. in argon. After 30 min the batch was heated to RT and then stirred overnight (solid separated out). The reaction mixture was washed with water and saturated NaCl solution (50 mL), dried over $Na_2SO_4$, concentrated to low volume in a vacuum and the remaining residue purified by flash chromatography with ethyl acetate/MeOH 20:1.

Yield: 5.90 g (48%)

$^1$H-NMR (DMSO-$d_6$): 0.83 (1.5 H, s); 1.00 (1.5 H, s); 1.08 (1 H, m); 1.55-1.82 (5 H, m); 1.88 (3 H, s); 1.92 (3 H, s); 2.14-2.32 (2 H, m); 7.27 (5 H, m); 9.36 (0.5 H, s); 9.45 (0.5 H, s).

Step 3:

4-dimethylamino-1-methyl-4-phenyl-cyclohexane carbaldehyde oxime

A solution of the title compound of step 2 (5.90 g, 24.0 mmol) and hydroxylamine hydrochloride (2.50 mg, 36.0 mmol) in abs. ethanol (100 mL) were mixed with Amberlyst A 21 (17.0 g) and stirred for 20 h at RT. The ion exchanger was filtered off, the solution concentrated to low volume and the residue made alkaline with 1N NaOH. The aqueous phase was extracted with ethyl acetate, dried over $Na_2SO_4$ and concentrated to low volume in a vacuum.

Yield: 6.25 g (100%)

Step 4:

[4-aminomethyl-4-methyl-1-phenylcyclohexyl]-dimethylamine

Lithium aluminium hydride (1.82 g, 48.0 mmol) was suspended in abs. THF (200 mL) in argon, mixed in drops with a solution of the title compound from step 3 (6.25 g, 24.0 mmol) in abs. THF (20 mL) and boiled for 4 h with reflux. The batch was then hydrolysed with water (20 mL) at 10° C. and filtered off over diatomaceous earth. The THF was removed in a vacuum, the residue adjusted to pH 11 with 1N NaOH and extracted with ethyl acetate. The combined organic phases were dried over $Na_2SO_4$, concentrated to low volume in a vacuum and the remaining residue separated by flash chromatography with MeOH+1% $NH_3$.

Yield: 1.44 g (24%, non-polar diastereomer)

$^1$H-NMR (DMSO-$d_6$): 0.86 (3 H, s); 1.03 (2 H, m); 1.29 (2 H, m); 1.84 (2 H, m); 1.91 (6 H, s); 2.10 (2 H, m); 2.16 (2 H, s); 7.24 (1 H, m); 7.32 (4 H, m).

Yield: 1.53 g (26%, polar diastereomer)

$^1$H-NMR (DMSO-$d_6$): 0.72 (3 H, s); 1.00 (2 H, m); 1.49 (2 H, m); 1.83 (2 H, m); 1.90 (6 H, s); 2.05 (2 H, m); 2.39 (2 H, s); 7.23 (1 H, m); 7.34 (4 H, m).

Step 5:

[4-[(1H-indol-3-yl-methylamino)-methyl]-4-methyl-1-phenyl-cyclohexyl]-dimethylamine (Non-polar Diastereomer)

Indole-3 aldehyde (203 mg, 1.4 mmol) and the non-polar diastereomer from step 4 (345 mg, 1.4 mmol) were dissolved in abs. THF (10 mL), mixed with $Na_2SO_4$ (2.0 g) and stirred for 24 h at RT. Dichloroethane (10 mL) and sodium triacetoxyboron hydride (423 g, 2.0 mmol) were then added and stirred a further 24 h at RT. For work up the solvent was removed in a vacuum, the residue mixed with EE (20 mL), water (20 mL) and 10% sulphuric acid (to pH 1) and the phases separated. The aqueous phase was adjusted to pH 11 with 5N NaOH and extracted three times with ethyl acetate. The combined organic phases were dried over $Na_2SO_4$, concentrated to low volume in a vacuum and the remaining residue purified by flash chromatography with ethyl acetate/MeOH 1:1+1% $NH_3$.

Yield: 397 mg (76%), porous solid $^1$H-NMR (DMSO-$d_6$): 0.92 (3 H, s); 1.14 (2 H, m); 1.32 (2 H, m); 1.89 (8 H, bs); 2.05 (2 H, m); 2.22 (2 H, s); 3.75 (2 H, s); 6.9-7.54 (10 H, m); 10.75 (1 H, s).

Example 77

[4-[(1H-indol-3-yl-methylamino)-methyl]-4-methyl-1-phenyl-cyclohexyl]-dimethylamine (Polar Diastereomer)

Indole-3 aldehyde (203 mg, 1.4 mmol) and the polar diastereomer from Example 76, step 4 (345 mg, 1.4 mmol) were dissolved in abs. THF (10 mL), mixed with $Na_2SO_4$ (2.0 g) and stirred for 24 h at RT. Dichloroethane (10 mL) and sodium triacetoxyboron hydride (423 g, 2.0 mmol) were then added and stirred a further 24 h at RT. For work up the solvent was removed in a vacuum, the residue mixed with ethyl acetate (20 mL), water (20 mL) and 10% sulphuric acid (to pH 1) and the phases separated. The aqueous phase was adjusted to pH 11 with 5N NaOH and extracted three times with ethyl acetate. The combined organic phases were dried over $Na_2SO_4$, concentrated to low volume in a vacuum and the remaining residue purified by flash chromatography with ethyl acetate/MeOH (1:1+1% $NH_3$).

Yield: 370 mg (70%)
Melting point: 55-56° C.
$^1$H-NMR (DMSO-$d_6$): 0.78 (3 H, s); 1.02 (2 H, m); 1.57 (3 H, m); 1.79 (2 H, m) 1.86 (6 H, s); 2.02 (2 H, m); 2.44 (2 H, s); 3.89 (2 H, s); 6.97 (1 H, t); 7.06 (1 H, t); 7.22-7.32 (7 H, m); 7.64 (1 H, d); 10.82 (1 H, s).

Example 78

[4-[(1H-indol-3-yl-methyl-methyl-amino)-methyl]-4-methyl-1-phenyl-cyclohexyl]-dimethylamine (Non-polar Diastereomer)

A solution of the title compound from Example 76 (300 mg, 0.8 mmol) and formalin (1.2 mL, 37% aqueous solution) in acetonitrile (10 mL) was mixed in portions with sodium cyanoboron hydride (201 mg, 3.2 mmol) and stirred for 2 h at RT. Conc. acetic acid was then added until a neutral reaction occurred and the mixture stirred for 45 h at RT. For work up the solvent was removed in a vacuum, the residue taken up in 2N NaOH (10 mL) and then extracted with ether (3×20 mL). The organic solution was dried over $Na_2SO_4$ and concentrated to low volume in a vacuum. The remaining residue was purified by flash chromatography with ethyl acetate/MeOH (1:1).

Yield: 189 mg (56%)
According to LMR and LCMS this was a hydroxymethyl compound that was dissolved in 1N NaOH (2 mL) and THF (2 mL) and boiled for 2 h with reflux. The mixture was then extracted with ether (2×20 mL). The organic solution was dried over $Na_2SO_4$ and concentrated to low volume in a vacuum. The remaining residue was purified by flash chromatography with EE/MeOH (1:1+1% $NH_3$).

Yield: 119 mg (38%)
$^1$H-NMR (CDCl$_3$): 1.04 (3 H, s); 1.32 (4 H, m); 1.87 (2 H, m); 2.05 (6 H, s) 2.14 (2 H, s); 2.15 (3 H, s); 2.34 (2 H, m); 3.63 (2 H, s); 6.78 (1 H, s); 7.08 (1 H, t); 7.17 (1 H, t); 7.30-7.41 (6 H, m); 7.62 (1 H, d); 7.99 (1 H, s).

Example 79

[4-[(1H-indol-3-yl-methyl-methyl-amino)-methyl]-4-methyl-1-phenyl-cyclohexyl]-dimethylamine (Polar Diastereomer)

A solution of the title compound from Example 77 (300 mg, 0.8 mmol) and formalin (1.2 mL, 37% aqueous solution) in acetonitrile (10 mL) was mixed in portions with sodium cyanoboron hydride (201 mg, 3.2 mmol) and stirred for 2 h at RT. Conc. acetic acid was then added until a neutral reaction occurred and stirred for 45 h at RT. For work up the solvent was removed in a vacuum, the residue taken up in 2N NaOH (10 mL) and then extracted with ether (3×20 mL). The organic solution was dried over $Na_2SO_4$ and concentrated to low volume in a vacuum. The remaining residue was purified by flash chromatography with EE/MeOH (1:1.5 mL), a colourless solid precipitated out and this was separated. According to NMR and LCMS this was the hydroxymethyl compound.

The mother liquor was concentrated to low volume (240 mg), this was also the hydroxymethyl compound.
Yield: 299 mg (89%)
The hydroxymethyl compound (240 mg, 0.57 mmol) was dissolved in 1N NaOH (2 mL) and THF (2 mL) and boiled for 2 h with reflux. The mixture was then extracted with ether (2×20 mL). The organic solution was dried over $Na_2SO_4$ and concentrated to low volume in a vacuum. The remaining residue was purified by flash chromatography with EE/MeOH (1:1+1% $NH_3$).

Yield: 181 mg (82%)
$^1$H-NMR (CDCl$_3$): 0.88 (3 H, s); 1.13 (2 H, m); 1.74 (2 H, m); 1.80 (4 H, m) 2.10 (6 H, s); 2.29 (3 H, s); 2.44 (2 H, s); 3.78 (2 H, s); 7.10-7.40 (9 H, m); 7.85 (1 H, d); 8.24 (1 H, s).

Example 80

[3-[[[4-(dimethylamino)-1-methyl-4-phenyl-cyclohexyl]-methyl-methyl-amino]-methyl]-1H-indol-1-yl]-methanol (Polar Diastereomer)

The hydroxymethyl compound was formed as intermediate product as part of the synthesis of Example 79.
Yield: 299 mg (89%)
$^1$H-NMR (CDCl$_3$): 0.41 (2 H, m); 0.62 (2 H, m); 0.65 (3 H, s); 1.27 (2 H, m) 1.61 (2 H, m); 1.75 (6 H, s); 2.28 (2 H, s); 2.47 (3 H, s); 3.64 (2 H, s); 5.63 (2 H, s); 7.01 (2 H, m); 7.14-7.40 (7 H, m); 7.76 (1 H, d)

Example 86

[4-[[4,6-bis(methylamino)-[1,3,5]triazin-2-yl]-methyl-amino]-1,4-diphenyl-cyclohexyl]-dimethylamine (Non-polar Diastereomer)

The title compound of Example 103 (200 mg, 0.31 mmol) was dissolved in a 33% methylamine solution in ethanol (2 mL) and stirred in the microwave for 30 min at 100° C. and 60 min at 120° C. The precipitated precipitate was aspirated and dried in a vacuum.

Yield: 89 mg (64%)
Melting point: 250-252° C.
$^1$H-NMR (DMSO): 1.65 (2 H, m); 1.96 (6 H, s); 2.41 (4 H, m); 2.60 (6 H, s); 3.06 (5 H, m); 6.21 (2 H, m); 7.16-7.43 (10 H, m).

Example 87

[4-[[4-(4-methoxy-phenoxy)-6-methylamino-[1,3,5]triazin-2-yl]-methyl-amino]-1,4-diphenyl-cyclohexyl]-dimethylamine (Non-polar Diastereomer)

As part of the synthesis of the title compound of Example 86 the mother liquor was concentrated to low volume in a vacuum and the remaining residue was purified by flash chromatography with ethyl acetate.

Yield: 25 mg (15%)

Melting point: 181-182° C.

$^1$H-NMR (DMSO), temp: 100° C.: 1.70 (2 H, m); 1.99 (6 H, s); 2.24 (2 H, m); 2.38 (2 H, m); 2.56 (2 H, m); 2.67 (3 H, d); 2.96 (3 H, s); 3.76 (3 H, s); 6.71 (1 H, m); 6.98 (3 H, m); 7.15-7.38 (10 H, m).

The following compounds were obtained following a specification such as described in Examples 86 and 87 except that the educts listed in Table 1-4 were used.

TABLE 1-4

| Ex. No. | Educt | Method according to | Product | Cy (%)/ MS (m/z) |
|---|---|---|---|---|
| 90 | Ex. 100 | Ex. 86 | [4-[[4,6-bis(methylamino)-[1,3,5]triazin-2-yl]-methyl-amino]-1,4-diphenyl-cyclohexyl]-dimethylamine (polar diastereomer) | 13 (446) |
| 91 | Ex. 100 | Ex. 87 | [4-[[4-(4-methoxy-phenoxy)-6-methylamino-[1,3,5]triazin-2-yl]-methyl-amino]-1,4-diphenyl-cyclohexyl]-dimethylamine (polar diastereomer) | 59 (539) |

Example 94

[4-(dimethylamino)-1-(3-fluorophenyl)-4-(3-methyl-1H-indol-2-yl)-cyclohexyl]-dimethylamine (Polar Diastereomer)

Step 1:

4-(dimethylamino)-4-(3-fluorophenyl)-1-(3-methyl-1H-indol-2-yl)cyclohexanol (non-polar and polar diastereomer)

n-butyl lithium (8.39 mmol, 3.35 ml, 2.5M in hexane) was slowly added to a solution of skatole (1.00 g, 7.62 mmol) in absolute tetrahydrofuran (25 ml) in an argon atmosphere at −78° C. A colourless precipitate was formed. After 10 min the solution was heated to room temperature. Carbon dioxide was then introduced into the reaction mixture for approx. 3 min. A colourless solution was formed. After 5 min the volatile constituents were completely removed in a vacuum at room temperature (water bath temperature≤30° C.). The colourless solid residue was again dissolved in absolute tetrahydrofuran (20 ml). The light yellow reaction mixture was cooled to −78° C. and tert-butyl lithium (8.39 mmol, 5.59 ml, 1.5M in pentane) was added in drops. An orange solution was formed. This was stirred for 1 h at −20° C. and then cooled to −78° C. 4-(dimethylamino)-4-(3-fluorophenyl)cyclohexanone [1.97 g, 8.39 mmol, in absolute tetrahydrofuran (20 ml)] was then added in drops and the resulting solution stirred for 2 h. Saturated aqueous ammonium chloride solution (50 ml) was then added in drops to the reaction mixture, stirred for 10 min, the mixture heated to 0° C. and stirred for 20 min. 2N aqueous hydrogen chloride solution (50 ml) was added thereto and stirred for 10 min (light gas development). The pH value of the milky suspension was then basified with saturated sodium hydrogencarbonate solution (50 ml) and 5N sodium hydroxide solution (20 ml). After 10 min the phases were separated. The organic phase contained a colourless solid. The phases were separated. The aqueous phase was extracted with dichloromethane/methanol 20:1 (3×50 ml). The organic solutions were combined. The volatile constituents were completely removed in a vacuum. The remaining light brown powder was extracted with methanol (5×75 ml). The residue was exclusively composed of the non-polar diastereoisomer 6b/7b (450 mg, 1.23 mmol, 16%). The extracts were concentrated until dry in a vacuum. The residue was taken up in methanol (approx. 30 ml). A light-coloured solid did not dissolve. This was separated by means of a fritted glass filter and then dried in a vacuum. 980 mg (2.67 mmol, 35%) of a colourless powder were obtained. This was composed of the two diastereoisomers.

The mother liquor was separated by chromatography [silica gel 60 (150 g); trichloromethane/ethanol 50:1 (500 ml), 19:1 (500 ml), 9:1 (300 ml), 5:1 (300 ml), 1:1 (300 ml), 0.5% triethylamine in each case, better begin with trichloromethane/ethanol 100:1]. The obtained fractions of the two diastereoisomers had to be recrystallised from methanol. 93 mg (0.25 mmol, 3%) of the more non-polar diastereoisomer (mp 197-202° C.) and 146 mg (0.40 mmol, 5%) of the more polar diastereoisomer (179-188° C.) were obtained.

13C{1H}-NMR (101 MHz, DMSO-D6, δ ppm, more non-polar diastereoisomer): 9.5 (1 C), 28.4 (2 C), 32.5 (2 C), 37.8 (2 C), 58.2 (1 C, br), 69.4 (1 C), 102.7 (1 C), 111.0 (1 C), 113.0 (1 C, d, J=21 Hz), 113.4 (1 C, d, J=21 Hz), 117.3 (1 C), 117.8 (1 C) 119.9 (1 C), 122.6 (1C, d, J=2 Hz), 128.9 (1 C, J=8 Hz), 129.8 (1 C), 133.9 (1 C), 142.1 (1 C, br), 142.7 (1 C, d, J=5 Hz), 161.9 (1 C, d, J=242 Hz)

13C{1H}-NMR (101 MHz, DMSO-D6, δ ppm, more polar diastereoisomer): 9.0 (1 C), 26.9 (2 C, br), 33.5 (2 C), 37.6 (2 C), 55.9 (1 C, br), 68.5 (1 C), 102.3 (1 C), 110.9 (1 C), 113.5 (1C, sbr), 115.8 (1 C, sbr), 117.2 (1 C), 117.8 (1 C) 120.0 (1 C), 125.0 (1 C, sbr), 126.6 (1 C), 130.0 (1 C, br), 133.7 (1 C), 141.1 (1 C, br), 162.4 (1 C, d, J=244 Hz), n.b. (1 C)

Step 2:

1-(3-fluorophenyl)-4-(1H-indol-2-yl)-7,7-dimethyl-7-azoniabicyclo[2.2.1]heptane fluoride The alcohol from step 1 (both diastereoisomers, 2.20 g, 6.00 mmol) was suspended in absolute dichloromethane (50 ml) at −78° C. Triethylamine (3.65 g, 36.02 mmol, 4.99, 0.73 g/ml), DMAP (16 mg, 0.12 mmol) and DAST (2.90 g, 18.01 mmol, 2.36 ml, 1.23 g/ml) were added one after the other. The solution was stirred for 1 h at −78° C. The reaction mixture was then heated to room temperature within 10 h (overnight). Saturated sodium hydrogencarbonate solution (50 ml) was then added and stirred for 15 min (until the gas development was finished). Sodium hydroxide solution (5N, 20 ml) was then added and stirred for 10 min. The phases were separated.

The red-brown organic phase was concentrated until dry in a vacuum. The brown solid obtained was then dissolved in methanol (50 ml). The aqueous phase was also concentrated until dry in a vacuum. The light-coloured residue was extracted with methanol (5×75 ml). The combined methanol solutions were concentrated until dry in a vacuum. The residue was extracted firstly with dichloromethane (2×30 ml) and then with methanol (5×75 ml). A light-coloured solid remained. The methanol extracts were concentrated until dry in a vacuum. There remained 1.20 g (3.26 mmol, 54%) of the product as light-coloured solid. The dichloromethane extracts were concentrated until dry in a vacuum. The residue was taken up in methanol (5 ml) and left to stand. A white solid separated out. A further 0.43 g (1.16 mmol, 19%) of the product (mp 175° C.) was thus obtained.

$^{13}C\{^1H\}$-NMR (101 MHz, DMSO-D$_6$, δ ppm): 11.2 (1 C), 29.8 (2 C), 30.3 (2 C), 40.6 (2 C), 81.2 (1 C, d, J=2 Hz), 83.2 (1 C), 111.5 (1 C), 114.4 (1 C), 116.7 (1 C, d, J=23 Hz), 117.6 (1 C, d, J=21 Hz), 119.11 (1 C), 119.13 (1 C) 121.7 (1 C), 123.4 (1 C), 125.6 (1 C, J=3 Hz), 128.8 (1 C), 131.0 (1 C, d, J=8 Hz), 132.2 (1 C, d, J=7 Hz), 135.8 (1 C), 162.3 (1 C, d, J=244 Hz)

Step 3:

[4-(dimethylamino)-1-(3-fluorophenyl)-4-(3-methyl-1H-indol-2-yl)-cyclohexyl]-dimethylamine (Polar Diastereomer)

The title compound from step 2 (500 mg, 1.36 mmol) was suspended in acetonitrile/methanol (1:1.20 ml). Dimethylamine (2M in tetrahydrofuran, 14 ml, 27.15 mmol) was then added and stirred for 2 d at room temperature. The solution was stirred for 6 h at 80° C. (oil bath temperature), then applied to coarse silica gel and separated by flash chromatography [silica gel 60 (150 g); trichloromethane/ethanol 50:1 (1000 ml), 19:1 (500 ml), 9:1 (1000 ml), 0.5% triethylamine in each case]. The more non-polar diastereoisomer was firstly isolated. In addition, 250 mg of a solid mixture were isolated. The solid mixture was dissolved in methanol (10 ml), 50 mg of potassium hydroxide added and stirred for 10 min. The volatile constituents were removed completely in a vacuum. The light-coloured residue was extracted with ethyl acetate (3×20 ml). The volatile constituents were released from the extracts in a vacuum. 135 mg (0.34 mmol, 25%) of the more polar diastereoisomer (mp 65-73° C.) were isolated.

$^{13}C\{^1H\}$-NMR (101 MHz, DMSO-D$_6$, δ ppm, more polar diastereoisomer): 10.7 (1 C), 28.8 (2 C, br), 29.3 (2 C, br), 37.7 (2 C), 38.7 (2 C), 58.7 (1 C, br), 60.5 (1 C, br), 107.0 (1 C, br), 110.5 (1 C), 112.9 (1 C, d, J=21 Hz), 113.7 (1 C, d, J=21 Hz), 117.5 (1 C), 117.7 (1 C), 120.4 (1 C), 122.9 (1 C, br), 128.9 (1 C, d, J=8 Hz), 129.0 (1 C), 132.5 (1 C, sbr), 134.5 (1C), 141.4 (1 C, br), 161.9 (1 C, d, J=243 Hz)

Example 97

[4-(dimethylamino)-1-(3-fluorophenyl)-4-(3-methyl-1H-indol-2-yl)-cyclohexyl]-dimethylamine (Non-polar Diastereomer)

The non-polar diastereomer was also formed during the synthesis of the title compound of Example 94, step 3. 152 mg (0.39 mmol, 29%) (mp 126-132° C.) were isolated.

$^{13}C\{^1H\}$-NMR (101 MHz, DMSO-D$_6$, δ ppm, more non-polar diastereoisomer): 10.7 (1 C), 29.6 (2 C, br), 29.7 (2 C, br), 37.8 (2 C), 38.7 (2 C), 60.0 (1 C, br), 60.6 (1 C, br), 107.0 (1 C, br), 110.5 (1 C), 113.0 (1 C, d, J=21 Hz), 114.2 (1 C, d, J=21 Hz), 117.5 (1 C), 117.8 (1 C), 120.4 (1 C), 123.5 (1 C, br), 129.1 (1 C), 129.1 (1 C, d, J=6 Hz), 132.2 (1 C, br), 134.6 (1C), 140.4 (1 C, br), 162.2 (1 C, d, J=242 Hz)

The following compounds were obtained following a specification such as described in Examples 94 and 97 except that the educts listed in Table 1-5 were used.

TABLE 1-5

| Ex. No. | Indole | Ketone | Amine | Product | Cy* (%)/ MS (m/z) |
| --- | --- | --- | --- | --- | --- |
| 35 | Skatole | BB-A | Dimethylamine | [4-(dimethylamino)-4-(3-methyl-1H-indol-2-yl)-1-phenyl-cyclohexyl]-dimethylamine (polar diastereomer) | 27 (376) |
| 36 | Skatole | BB-A | Dimethylamine | [4-(dimethylamino)-4-(3-methyl-1H-indol-2-yl)-1-phenyl-cyclohexyl]-dimethylamine (non-polar diastereomer) | 25 (376) |
| 53 | Skatole | BB-A | Pyrrolidine | dimethyl-[4-(3-methyl-1H-indol-2-yl)-1-phenyl-4-pyrrolidin-1-yl-cyclohexyl]-amine dihydrochloride (polar diastereomer) | 17 (402) |
| 54 | Skatole | BB-A | Pyrrolidine | dimethyl-[4-(3-methyl-1H-indol-2-yl)-1-phenyl-4-pyrrolidin-1-yl-cyclohexyl]-amine (non-polar diastereomer) | 48 (402) |
| 56 | Skatole | BB-A | Acetidine | [4-(acetidin-1-yl)-4-(3-methyl-1H-indol-2-yl)-1-phenyl-cyclohexyl]-dimethylamine (non-polar diastereomer) | 19 (388) |
| 82 | Skatole | BB-A | Methylamine | [4-dimethylamino-1-(3-methyl-1H-indol-2-yl)-4-phenyl-cyclohexyl]-methylamine (polar diastereomer) | 26 (362) |
| 83 | Skatole | BB-A | Methylamine | [4-dimethylamino-1-(3-methyl-1H-indol-2-yl)-4-phenyl-cyclohexyl]-methylamin (non-polar diastereomer) | 22 (362) |
| 84 | Skatole | BB-A | Benzylamine | benzyl-[4-dimethylamino-1-(3-methyl-1H-indol-2-yl)-4-phenyl-cyclohexyl]-amine; 2-hydroxy-propane-1,2,3-tricarboxylic acid | 12 (438) |

TABLE 1-5-continued

| Ex. No. | Indole | Ketone | Amine | Product | Cy* (%)/ MS (m/z) |
|---|---|---|---|---|---|
| 95 | Skatole | BB-B | Acetidine | 4-(acetidin-1-yl)-1-(3-fluorophenyl)-N,N-dimethyl-4-(3-methyl-1H-indol-2-yl)cyclohexanamine (non-polar diastereomer) | 33 (406) |
| 96 | Skatole | BB-B | Acetidine | 4-(acetidin-1-yl)-1-(3-fluorophenyl)-N,N-dimethyl-4-(3-methyl-1H-indol-2-yl)cyclohexanamine (polar diastereomer) | 4 (406) |
| 108 | Skatole | BB-B | Pyrrolidine | [1-(3-fluorophenyl)-4-(3-methyl-1H-indol-2-yl)-4-pyrrolidin-1-yl-cyclohexyl]-dimethylamine (non-polar diastereomer) | 36 (420) |
| 109 | Skatole | BB-B | Pyrrolidine | [1-(3-fluorophenyl)-4-(3-methyl-1H-indol-2-yl)-4-pyrrolidin-1-yl-cyclohexyl]-dimethylamine (polar diastereomer) | 29 (420) |
| 110 | Skatole | BB-B | Methylamine | [1-(3-fluorophenyl)-4-methylamino-4-(3-methyl-1H-indol-2-yl)-cyclohexyl]-dimethyl-amine | 10 (380) |
| 111 | Skatole | BB-A | Piperidine | dimethyl-[4-(3-methyl-1H-indol-2-yl)-1-phenyl-4-piperidin-1-yl-cyclohexyl]-amine (non-polar diastereomer) | 23 (416) |
| 112 | Skatole | BB-B | Piperidine | [1-(3-fluorophenyl)-4-(3-methyl-1H-indol-2-yl)-4-piperidin-1-yl-cyclohexyl]-dimethylamine (polar diastereomer) | 4 (434) |
| 133 | Skatole | BB-B | Piperidine | [1-(3-fluorophenyl)-4-(3-methyl-1H-indol-2-yl)-4-piperidin-1-yl-cyclohexyl]-dimethylamine (non-polar diastereomer) | 35 (434) |
| 113 | IN-A | BB-A | Dimethylamine | [4-(dimethylamino)-4-(5-fluoro-3-methyl-1H-indol-2-yl)-1-phenyl-cyclohexyl]-dimethyl-amine (polar diastereomer) | 41 (394) |
| 125 | IN-A | BB-A | Dimethylamine | [4-(dimethylamino)-4-(5-fluoro-3-methyl-1H-indol-2-yl)-1-phenyl-cyclohexyl]-dimethyl-amine (non-polar diastereomer) | 27 (394) |
| 126 | IN-A | BB-A | Pyrrolidine | [4-(5-fluoro-3-methyl-1H-indol-2-yl)-1-phenyl-4-pyrrolidin-1-yl-cyclohexyl]-dimethylamine (non-polar diastereomer) | 42 (420) |
| 132 | IN-A | BB-A | Pyrrolidine | [4-(5-fluoro-3-methyl-1H-indol-2-yl)-1-phenyl-4-pyrrolidin-1-yl-cyclohexyl]-dimethylamine (polar diastereomer) | 38 (420) |
| 134 | IN-A | BB-B | Acetidine | [4-(acetidin-1-yl)-4-(5-fluoro-3-methyl-1H-indol-2-yl)-1-(3-fluorophenyl)-cyclohexyl]-dimethylamine (polar diastereomer) | 55 (406) |
| 135 | IN-A | BB-B | Acetidine | [4-(acetidin-1-yl)-4-(5-fluoro-3-methyl-1H-indol-2-yl)-1-(3-fluorophenyl)-cyclohexyl]-dimethylamine (non-polar diastereomer) | 28 (406) |
| 136 | IN-A | BB-A | Morpholine | [4-(5-fluoro-3-methyl-1H-indol-2-yl)-4-morpholin-4-yl-1-phenyl-cyclohexyl]-dimethylamine (polar diastereomer) | 30 (436) |
| 140 | IN-A | BB-A | Morpholine | [4-(5-fluoro-3-methyl-1H-indol-2-yl)-4-morpholin-4-yl-1-phenyl-cyclohexyl]-dimethylamine (non-polar diastereomer) | 15 (436) |
| 137 | IN-A | BB-A | Methylamine | [4-(5-fluoro-3-methyl-1H-indol-2-yl)-4-methylamino-1-phenyl-cyclohexyl]-dimethylamine (non-polar diastereomer) | 11 (380) |

TABLE 1-5-continued

| Ex. No. | Indole | Ketone | Amine | Product | Cy* (%)/ MS (m/z) |
|---|---|---|---|---|---|
| 138 | IN-A | BB-A | Methylamine | [4-(5-fluoro-3-methyl-1H-indol-2-yl)-4-methylamino-1-phenyl-cyclohexyl]-dimethylamine (polar diastereomer) | 11 (380) |
| 139 | IN-A | BB-C | Methylamine | dimethyl-[4-methylamino-4-(3-methyl-1H-indol-2-yl)-1-thiophen-2-yl-cyclohexyl]-amine (polar diastereomer) | 21 (368) |
| 150 | IN-A | BB-C | Methylamine | dimethyl-[4-methylamino-4-(3-methyl-1H-indol-2-yl)-1-thiophen-2-yl-cyclohexyl]-amine (non-polar diastereomer) | 46 (368) |
| 159 | IN-A | BB-B | Cyclohexylmethylamine | [4-(cyclohexyl-methylamino)-1-(3-fluorophenyl)-4-(3-methyl-1H-indol-2-yl)-cyclohexyl]-dimethylamine (non-polar diastereomer) | 43 (462) |
| 160 | IN-A | BB-B | Cyclopentylamine | [4-(cyclopentylamino)-1-(3-fluorophenyl)-4-(3-methyl-1H-indol-2-yl)-cyclohexyl]-dimethyl-amine (non-polar diastereomer) | 36 (434) |
| 161 | IN-A | BB-B | Aniline | [4-anilino-1-(3-fluorophenyl)-4-(3-methyl-1H-indol-2-yl)-cyclohexyl]-dimethylamine | 28 (381; M + 1 − NMe$_2$ − Me) |
| 162 | IN-A | BB-B | 4-Aminopyridine | [1-(3-fluorophenyl)-4-(3-methyl-1H-indol-2-yl)-4-(pyridin-4-ylamino)-cyclohexyl]-dimethyl-amine | 5 (443) |

*for the last step.

The following compounds were obtained following a specification such as described in Example 86 except that amines and educts such as listed in Table 1-6 were used, and also in the case of high-boiling amines the operation was conducted without solvent.

TABLE 1-6

| Ex. No. | Educt | Amine | Product | Cy (%)/ MS (m/z) |
|---|---|---|---|---|
| 129 | Ex. 91 | Piperidine | dimethyl-[4-[methyl-(4-methylamino-6-piperidin-1-yl-[1,3,5]triazin-2-yl)-amino]-1,4-diphenyl-cyclohexyl]-amine (polar diastereomer) | 89 (500) |
| 141 | Ex. 87 | Aniline | [4-[(4-anilino-6-methylamino-[1,3,5]triazin-2-yl)-methyl-amino]-1,4-diphenyl-cyclohexyl]-dimethyl-amine (non-polar diastereomer) | 38 (508) |
| 142 | Ex. 91 | N-Isopropylmethylamine | [4-[[4-(isopropyl-methyl-amino)-6-methylamino-[1,3,5]triazin-2-yl]-methyl-amino]-1,4-diphenyl-cyclohexyl]-dimethylamine (polar diastereomer) | 44 (488) |
| 143 | Ex. 91 | Aniline | [4-[(4-anilino-6-methylamino-[1,3,5]triazin-2-yl)-methyl-amino]-1,4-diphenyl-cyclohexyl]-dimethyl-amine (polar diastereomer) | 84 (508) |
| 144 | Ex. 91 | Benzylamine | [4-[[4-(benzylamino)-6-methylamino-[1,3,5]triazin-2-yl]-methyl-amino]-1,4-diphenyl-cyclohexyl]-dimethylamine (polar diastereomer) | 90 (522) |
| 145 | Ex. 91 | Butylamine | [4-[(4-butylamino-6-methylamino-[1,3,5]triazin-2-yl)-methyl-amino]-1,4-diphenyl-cyclohexyl]-dimethyl-amine (polar diastereomer) | 86 (488) |

Example 100

[4-[[4,6-bis(4-methoxy-phenoxy)-[1,3,5]-triazin-2-yl]-methyl-amino]-1,4-diphenyl-cyclohexyl]-dimethylamine (Polar Diastereomer)

A solution of the title compound from Example 9 (616 mg, 2.0 mmol) and 4-methoxyphenyl cyanate (895 mg, 6.0 mmol) in abs. acetone (20 mL) was stirred for 3 d at RT. The solvent was then removed in a vacuum and the remaining residue purified by flash chromatography with ethyl acetate/MeOH (20:1).

Yield: 1.16 g (92%)

$^1$H-NMR (CDCl$_3$): 1.77 (4 H, m); 1.89 (6 H, s); 2.50 (4 H, m); 3.07 (3 H, s); 3.76 (6 H, s); 6.84-7.36 (18 H, m).

Example 103

[4-[[4,6-bis(4-methoxy-phenoxy)-[1,3,5]triazin-2-yl]-methyl-amino]-1,4-diphenyl-cyclohexyl]-dimethylamine (Non-polar Diastereomer)

A solution of the title compound from Example 8 (154 mg, 0.5 mmol) and 4-methoxyphenyl cyanate (224 mg, 1.5 mmol) in abs. acetone (10 mL) was stirred for 3 d at RT. The solvent was then removed in a vacuum and the remaining residue purified by flash chromatography with ethyl acetate/cyclohexane (1:1).

Yield: 226 mg (72%)

$^1$H-NMR (CDCl$_3$): 1.80 (4 H, m); 1.96 (6 H, s); 2.28 (2 H, m); 2.43 (2 H, m); 3.04 (3 H, s); 3.80 (6 H, s); 6.89-7.40 (18 H, m).

The following compounds were obtained following a specification such as described in Example 24 except that acylation and sulphonylation reagents and amines such as listed in Table 1-7 were used.

TABLE 1-7

| Ex. No. | Amine | Reagent | Product | Cy (%)/ MS (m/z) |
|---|---|---|---|---|
| 25 | Ex. 8 | Acetyl chloride | N-(4-dimethylamino-1,4-diphenyl-cyclohexyl)-N-methyl-acetamide (non-polar diastereomer) | 68 (351) |
| 26 | Ex. 9 | Methane sulphonyl chloride | N-(4-dimethylamino-1,4-diphenyl-cyclohexyl)-N-methyl-methanesulphonic acid amide (polar diastereomer) | 36 (387) |
| 27 | Ex. 9 | Cinnamic acid chloride | (E)—N-(4-dimethylamino-1,4-diphenyl-cyclohexyl)-N-methyl-3-phenyl-acrylamide (polar diastereomer) | 90 (439) |
| 28 | Ex. 9 | Acetyl chloride | N-(4-dimethylamino-1,4-diphenyl-cyclohexyl)-N-methyl-acetamide (polar diastereomer) | 65 (351) |
| 29 | Ex. 8 | Benzyl isocyanate | 3-benzyl-1-(4-dimethylamino-1,4-diphenyl-cyclohexyl)-1-methyl-urea (non-polar diastereomer) | 79 (442) |
| 30 | Ex. 9 | Benzyl isocyanate | 3-benzyl-1-(4-dimethylamino-1,4-diphenyl-cyclohexyl)-1-methyl-urea (polar diastereomer) | 88 (442) |
| 31 | Ex. 8 | Ethyl isocyanate | 1-(4-dimethylamino-1,4-diphenyl-cyclohexyl)-3-ethyl-1-methylurea (non-polar diastereomer) | 60 (380) |
| 32 | Ex. 9 | Ethyl isocyanate | 1-(4-dimethylamino-1,4-diphenyl-cyclohexyl)-3-ethyl-1-methylurea (polar diastereomer) | 100 (380) |
| 43 | Ex. 42, step 4 (non-polar) | Cinnamic acid chloride | (E)—N-[[4-dimethylamino-4-(3-fluorophenyl)-1-methyl-cyclohexyl]-methyl]-3-phenyl-acrylamide (non-polar diastereomer) | 96 (395) |
| 44 | Ex. 42, step 4 (non-polar) | (E)-2-phenylethene sulphonyl chloride | (E)—N-[[4-dimethylamino-4-(3-fluorophenyl)-1-methyl-cyclohexyl]-methyl]-2-phenylethene sulphonamide (non-polar diastereomer) | 68 (431) |
| 45 | Ex. 42, step 4 (polar) | (E)-2-phenylethene sulphonyl chloride | (E)—N-[[4-dimethylamino-4-(3-fluorophenyl)-1-methyl-cyclohexyl]-methyl]-2-phenylethene sulphonamide (polar diastereomer) | 66 (431) |
| 52 | Ex. 9 | Diphenyl acetyl chloride | N-[4-(dimethyl-amino)-1,4-diphenyl-cyclohexyl]-N-methyl-2,2-diphenyl-acetamide (polar diastereomer) | 23 (337) |

TABLE 1-7-continued

| Ex. No. | Amine | Reagent | Product | Cy (%)/ MS (m/z) |
|---|---|---|---|---|
| 57 | Ex. 8 | Methane sulphonyl chloride | N-(4-dimethylamino-1,4-diphenyl-cyclohexyl)-N-methyl-methane sulphonamide (non-polar diastereomer) | 15 (387) |
| 64 | Ex. 60 | Cinnamic acid chloride | (E)—N-[4-(cyclopentyl-methyl)-4-dimethylamino-1-phenyl-cyclohexyl]-N-methyl-3-phenyl-acrylamide (non-polar diastereomer) | 75 (445) |
| 65 | Ex. 61 | Cinnamic acid chloride | (E)—N-[4-(cyclopentyl-methyl)-4-dimethylamino-1-phenyl-cyclohexyl]-N-methyl-3-phenyl-acrylamide (polar diastereomer) | 63 (445) |
| 81 | Ex. 82 | Cinnamic acid chloride | (E)—N-[4-dimethylamino-1-(3-methyl-1H-indol-2-yl)-4-phenyl-cyclohexyl]-N-methyl-3-phenyl-acrylamide (polar diastereomer) | 17 (492) |
| 88 | Ex. 8 | Nicotinic acid chloride hydrochloride | N-[4-(dimethyl-amino)-1,4-diphenyl-cyclohexyl]-N-methyl-pyridine-3-carboxylic acid amide (non-polar diastereomer) | 58 (414) |
| 92 | Ex. 9 | 1-methyl-1H-pyrazole-3-carboxylic acid chloride | N-[4-(dimethyl-amino)-1,4-diphenyl-cyclohexyl]-N,1-dimethyl-1H-pyrazole-3-carboxylic acid amide (polar diastereomer) | 93 (417) |
| 98 | Ex. 8 | 3-trifluoromethyl-benzoyl chloride | N-(4-dimethylamino-1,4-diphenyl-cyclohexyl)-N-methyl-3-(trifluoromethyl)-benzamide (non-polar diastereomer) | 43 (481) |
| 99 | Ex. 9 | 3-(trifluoromethyl)benzoyl chloride | N-(4-dimethylamino-1,4-diphenyl-cyclohexyl)-N-methyl-3-(trifluoromethyl)-benzamide (polar diastereomer) | 67 (481) |
| 104 | Ex. 8 | 4-methoxy-phenyl-carboxylic acid chloride | N-(4-dimethylamino-1,4-diphenyl-cyclohexyl)-4-methoxy-N-methyl-benzamide (non-polar diastereomer) | 59 (443) |
| 105 | Ex. 9 | 4-methoxy-phenyl-carboxylic acid chloride | N-(4-dimethylamino-1,4-diphenyl-cyclohexyl)-4-methoxy-N-methyl-benzamide (polar diastereomer) | 90 (443) |
| 116 | Ex. 8 | 3-fluorobenzoyl chloride | N-(4-dimethylamino-1,4-diphenyl-cyclohexyl)-3-fluoro-N-methyl-benzamide (non-polar diastereomer) | 49 (431) |
| 117 | Ex. 9 | 3-fluorobenzoyl chloride | N-(4-dimethylamino-1,4-diphenyl-cyclohexyl)-3-fluoro-N-methyl-benzamide (polar diastereomer) | 84 (431) |
| 165 | Ex. 9 | Cyclohexane carboxylic acid chloride | N-(4-dimethylamino-1,4-diphenyl-cyclohexyl)-N-methyl-cyclohexane carboxylic acid amide (polar diastereomer) | 50 (419) |
| 166 | Ex. 9 | Tetrahydro-pyrane-4-carboxylic acid chloride | N-(4-dimethylamino-1,4-diphenyl-cyclohexyl)-N-methyl-tetrahydro-pyrane-4-carboxylic acid amide (polar diastereomer) | 30 (421) |
| 169 | Ex. 9 | 1-methyl-piperidine-4-carboxylic acid chloride | N-(4-dimethylamino-1,4-diphenyl-cyclohexyl)-N,1-dimethyl-piperidine-4-carboxylic acid amide (polar diastereomer) | 79 (434) |

The following compounds were obtained following a specification such as described in Example 48, step 2 except that the amides such as listed in Table 1-8 were used.

TABLE 1-8

| Ex. No. | Amide | Product | Cy (%)/MS (m/z) |
|---|---|---|---|
| 85 | BB-1 | dimethyl-[4-[methyl-(pyridin-3-yl-methyl)-amino]-1,4-diphenyl-cyclohexyl]-amine (polar diastereomer) | 37 (400) |
| 89 | Ex. 89 | dimethyl-[4-[methyl-(pyridin-3-yl-methyl)-amino]-1,4-diphenyl-cyclohexyl]-amine (non-polar diastereomer) | 73 (400) |
| 101 | Ex. 92 | (4-dimethylamino-1,4-diphenyl-cyclohexyl)-methyl-[(1-methyl-1H-pyrazol-3-yl)-methyl]-amine (polar diastereomer) | 71 (403) |
| 102 | Ex. 93 | (4-dimethylamino-1,4-diphenyl-cyclohexyl)-methyl-[(1-methyl-1H-pyrazol-3-yl)-methyl]-amine (non-polar diastereomer) | 67 (403) |
| 106 | Ex. 105 | (4-dimethylamino-1,4-diphenyl-cyclohexyl)-[(4-methoxyphenyl)-methyl]-methylamine (polar diastereomer) | 85 (429) |
| 107 | Ex. 104 | (4-dimethylamino-1,4-diphenyl-cyclohexyl)-[(4-methoxyphenyl)-methyl]-methylamine (non-polar diastereomer) | 77 (429) |
| 114 | Ex. 99 | (4-dimethylamino-1,4-diphenyl-cyclohexyl)-methyl-[[3-(trifluoromethyl)phenyl]-methyl]-amine (polar diastereomer) | 81 (467) |
| 115 | Ex. 98 | (4-dimethylamino-1,4-diphenyl-cyclohexyl)-methyl-[[3-(trifluoromethyl)phenyl]-methyl]-amine (non-polar diastereomer) | 42 (467) |
| 118 | Ex. 116 | (4-dimethylamino-1,4-diphenyl-cyclohexyl)-[(3-fluorophenyl)-methyl]-methyl-amine (non-polar diastereomer) | 98 (417) |
| 119 | Ex. 117 | (4-dimethylamino-1,4-diphenyl-cyclohexyl)-[(3-fluorophenyl)-methyl]-methyl-amine (polar diastereomer) | 99 (417) |
| 167 | Ex. 165 | cyclohexyl-methyl-(4-dimethylamino-1,4-diphenyl-cyclohexyl)-methylamine (polar diastereomer) | 84 (405) |
| 168 | Ex. 166 | (4-dimethylamino-1,4-diphenyl-cyclohexyl)-methyl-(tetrahydro-pyran-4-yl-methyl)-amine (polar diastereomer) | 44 (407) |
| 170 | Ex. 169 | (4-dimethylamino-1,4-diphenyl-cyclohexyl)-methyl-[(1-methyl-piperidin-4-yl)-methyl]-amine (polar diastereomer) | 93 (420) |

Example 120

2-[(4-dimethylamino-1,4-diphenyl-cyclohexyl)-methyl-amino]-ethanol (Polar Diastereomer)

Step 1:

[(4-dimethylamino-1,4-diphenyl-cyclohexyl)-methyl-amino]-methyl acetate

The title compound from Example 9 (463 mg, 1.50 mmol) was provided in abs. DMF (10 mL) and mixed with potassium carbonate (347 mg, 1.65 mmol) and methyl bromoacetate (157 µL, 1.65 mmol). The batch was stirred for 3 d at room temperature and then concentrated until dry in a vacuum. The residue was taken up in dichloromethane (50 mL) and washed with water (2×50 mL) and saturated NaCl solution (50 mL), the organic phase was then dried over $Na_2SO_4$ and concentrated to low volume in a vacuum. The residue was purified by means of flash chromatography with ethyl acetate/methanol (9:1).

Yield: 338 mg (59%)

$^1$H-NMR (DMSO-$d_6$): 1.73 (4 H, m); 1.96 (6 H, s); 2.04 (3 H, s); 2.31 (4 H, m); 2.96 (2 H, m); 3.58 (3 H, s); 7.17 (2 H, m); 7.28 (8 H, m).

Step 2:

2-[(4-dimethylamino-1,4-diphenyl-cyclohexyl)-methyl-amino]-ethanol (Polar Diastereomer)

The title compound from step 1 (322 mg, 0.85 mmol) was dissolved in abs. THF (15 mL), mixed with LiAlH$_4$ (64 mg, 1.69 mmol) in argon and boiled for 3 h with reflux. The batch was then cooled to room temperature, mixed with THF (10 mL) and H$_2$O (5 mL) with ice cooling and subsequently stirred for 30 min. The batch was filtered via a fritted glass filter with diatomaceous earth and the diatomaceous earth was subsequently washed with dichloromethane (50 mL). The combined filtrates were concentrated to low volume in a vacuum. The raw product was mixed with water (10 mL) and extracted with dichloromethane (3×20 mL). The organic phase was dried over Na$_2$SO$_4$ and concentrated to low volume in a vacuum. The residue was purified by means of flash chromatography with ethyl acetate/methanol (1:1).

Yield: 213 mg (71%)

$^1$H-NMR (DMSO-$d_6$): 1.72 (4 H, m); 1.95 (6 H, s); 2.06 (3 H, s); 2.19 (2 H, m); 2.29 (4 H, m); 3.39 (2 H, m); 4.25 (1 H, m); 7.17 (2 H, m); 7.27 (8 H, m).

Example 122

2-[(4-dimethylamino-1,4-diphenyl-cyclohexyl)-methyl-amino]-N-methyl-acetamide (Polar Diastereomer)

The title compound from Example 66 (293 mg, 0.8 mmol) was dissolved in abs. DMF (10 mL) and mixed with N-hydroxybenzotriazole hydrate (135 mg, 0.88 mmol) and TEA (1.11 mL, 8.0 mmol). After 30 min N-(3-dimethylaminopropyl)-N'-ethyl-carbodiimide hydrochloride (460 mg, 2.4 mmol) and methylamine (440 µL, 0.88 mmol, 2M solution in THF) were added and stirred overnight at RT. The solution was filtered and concentrated to low volume in a vacuum. By flash chromatography with ethyl acetate/MeOH (4:1→1:1), a salt of the product was obtained, which was released with 1N NaOH, extracted with CH$_2$Cl$_2$, dried over Na$_2$SO$_4$ and the solvent removed in a vacuum.

Yield: 182 mg (60%)

$^1$H-NMR (DMSO): 1.47 (2 H, m); 1.96 (7 H, s); 1.99 (3 H, s); 2.24 (3 H, m); 2.42 (2 H, m); 2.64 (6 H, m); 7.24 (9 H, m); 7.60 (1 H, m).

The following compounds were obtained following a specification such as described in Example 122 except that the acids and amines listed in Table 1-9 were used.

TABLE 1-9

| Ex. No. | Educt | Amine | Product | Cy (%)/ MS (m/z) |
|---|---|---|---|---|
| 121 | Ex. 66 | Dimethylamine | 2-[(4-dimethylamino-1,4-diphenyl-cyclohexyl)-methyl-amino]-N,N-dimethyl-acetamide (polar diastereomer) | 17 (394) |
| 123 | Ex. 67 | Dimethylamine | 2-[(4-dimethylamino-1,4-diphenyl-cyclohexyl)-methyl-amino]-N,N-dimethyl-acetamide (non-polar diastereomer) | 55 (380) |
| 124 | Ex. 67 | Methylamine | 2-[(4-dimethylamino-1,4-diphenyl-cyclohexyl)-methyl-amino]-N-methyl-acetamide (non-polar diastereomer) | 55 (394) |

Example 127

2-[[4-(dimethyl-amino)-1,4-diphenyl-cyclohexyl]-methyl-amino]-ethanol (Non-polar Diastereomer)

Step 1:

4[(4-dimethylamino-1,4-diphenyl-cyclohexyl)-methyl-amino]-methyl acetate

The title compound from Example 8 (463 mg, 1.50 mmol) was provided in abs. DMF (10 mL) and mixed with potassium carbonate (347 mg, 1.65 mmol) and methyl bromoacetate (157 μL, 1.65 mmol). The batch was stirred for 3 d at room temperature and then concentrated until dry in a vacuum. The residue was taken up in dichloromethane (50 mL) and washed with water (2×50 mL) and saturated NaCl solution (50 mL), the organic phase was dried over Na$_2$SO$_4$ and concentrated to low volume in a vacuum. The residue was purified by flash chromatography with ethyl acetate/methanol (9:1).

Yield: 234 mg (41%)

$^1$H-NMR (DMSO-d$_6$): 1.72 (4 H, m); 1.84 (6 H, s); 1.93 (3 H, s); 2.27 (4 H, m); 2.87 (2 H, m); 3.48 (3 H, s); 7.26 (2 H, m); 7.38 (8 H, m).

Step 2:

2-[[4-(dimethyl-amino)-1,4-diphenyl-cyclohexyl]-methyl-amino]-ethanol (Non-polar Diastereomer)

The title compound from step 1 (228 mg, 0.60 mmol) was dissolved in abs. THF (10 mL), mixed with LiAlH$_4$ (45 mg, 1.20 mmol) in argon and boiled for 3 h with reflux. The batch was then cooled to room temperature, mixed with THF (10 mL) and H$_2$O (5 mL) with ice cooling and subsequently stirred for 30 min. The batch was filtered via a fritted glass filter with diatomaceous earth and the diatomaceous earth subsequently washed with dichloromethane (50 mL). The combined filtrates were concentrated to low volume in a vacuum. The raw product was mixed with water (10 mL) and extracted with dichloromethane (3×20 mL), the organic phase was then dried over Na$_2$SO$_4$ and concentrated to low volume in a vacuum. The residue was purified by flash chromatography with ethyl acetate/methanol (9:1→4:1).

Yield: 174 mg (82%)

Melting point: 144-149° C.

$^1$H-NMR (DMSO-d$_6$): 1.73 (4 H, m); 1.84 (6 H, s); 1.96 (3 H, s); 2.09 (2 H, m); 2.27 (4 H, m); 3.23 (2 H, m); 4.14 (1 H, m); 7.25 (2 H, m); 7.38 (8 H, m).

Example 128

[4-[[4,6-bis(dimethylamino)-[1,3,5]triazin-2-yl]-methyl-amino]-1,4-diphenyl-cyclohexyl]-dimethyl-amine (Non-polar Diastereomer)

Step 1:

N-(4,6-dichloro-[1,3,5]triazin-2-yl)-N,N',N'-trimethyl-1,4-diphenyl-cyclohexane-1,4-diamine Cyanuric chloride (86 mg, 0.49 mmol) was provided in abs. THF (3 mL), mixed with a solution of the title compound from Example 8 (150 mg, 0.49 mmol) in abs. THF (6 mL) and N-ethyl diisopropylamine (80 μL, 0.49 mmol) and stirred for 16 h at RT. The solution was concentrated to low volume in a vacuum, the residue taken up in ethyl acetate (20 mL) and washed with saturated NaHCO$_3$ solution (2×10 mL) and saturated NaCl solution (10 mL). The organic phase was dried over Na$_2$SO$_4$ and concentrated to low volume in a vacuum. The raw product was purified by flash chromatography with ethyl acetate/methanol (20:1).

Yield: 67 mg (30%)

$^{13}$C-NMR (CDCl$_3$): 30.4, 31.4, 33.6, 38.0, 59.3, 66.4, 126.4, 126.7, 127.0, 127.1, 127.7, 128.2, 137.6, 143.1, 165.4, 168.0, 169.1

Step 2:

[4-[[4,6-bis(dimethylamino)-[1,3,5]triazin-2-yl]-methyl-amino]-1,4-diphenyl-cyclohexyl]-dimethyl-amine (Non-polar Diastereomer)

The title compound from step 1 (57 mg, 0.12 mmol) was dissolved in a 2M dimethylamine solution in THF (2.0 mL, 4 mmol) and stirred in the microwave for 2 h at 120° C. The reaction solution was concentrated to low volume in a vacuum, the remaining residue taken up in ethyl acetate (10 mL) and washed with saturated NaHCO$_3$ solution (2×5 mL) and saturated NaCl solution (5 mL). The organic phase was dried over Na$_2$SO$_4$ and concentrated to low volume in a vacuum. The raw product was purified by flash chromatography with ethyl acetate/MeOH (20:1).

Melting point: 195-197° C.

Yield: 45 mg (76%)

$^1$H-NMR (DMSO-d$_6$): 1.62 (2 H, m); 1.98 (6 H, s); 2.39 (2 H, m); 2.46 (2 H, m); 2.91 (12 H, s); 3.13 (3 H, s); 7.15 (1 H, m); 7.22-7.38 (9 H, m).

Example 130

4-[[4-(dimethylamino)-1,4-diphenyl-cyclohexyl]-methyl-amino]-butan-1-ol (Polar Diastereomer)

Step 1:

N-(4-dimethylamino-1,4-diphenyl-cyclohexyl)-N-methyl-tert-butyl succinate

The title compound from Example 131 (100 mg, 0.244 mmol) was provided in abs. dichloromethane (5 mL), mixed with trifluoroacetic anhydride (135 ml, 0.976 mmol) and stirred for 10 min. Tert-butyl alcohol (2 mL) was added to the batch and subsequently stirred for 30 min. The batch was then mixed with 10% NaOH and the phases separated. The organic phase was washed with $H_2O$ (1×10 mL), dried over $Na_2SO_4$ and concentrated to low volume in a vacuum.

Yield: 80 mg (70%)

$^1$H-NMR (DMSO-$d_6$): 1.38 (9 H, s); 1.53 (2 H, m); 1.78 (2 H, m); 1.92 (6 H, s); 2.37 (3 H, m); 2.62 (2 H, m); 2.93 (3 H, s), 7.11-7.27 (6 H, m); 7.36 (4 H, m).

Step 2:

4-[[4-(dimethylamino)-1,4-diphenyl-cyclohexyl]-methyl-amino]-butan-1-ol (Polar Diastereomer)

The title compound from step 1 (836 mg, 1.8 mmol) was dissolved in abs. THF (15 mL). LiAlH$_4$ (136 mg, 3.6 mmol) was added in argon, boiled for 2 h with reflux, cooled to room temperature and stirred overnight. THF (2 mL) and $H_2O$ (2 mL) were added to the batch with ice cooling and stirred for 30 min. The batch was passed through a fritted glass filter with diatomaceous earth, the diatomaceous earth washed with dichloromethane (50 mL), the organic phases purified and concentrated to low volume in a vacuum. The residue was purified by flash chromatography with chloroform/methanol (9:1).

Yield: 405 mg (59%)

$^1$H-NMR (DMSO-$d_6$): 1.39 (4 H, m); 1.74 (3 H, m); 1.96 (6 H, s); 2.01 (3 H, s); 2.11 (2 H, m); 2.30 (3 H, m); 3.36 (2 H, m); 4.41 (1 H, m); 7.18 (2 H, m); 7.28 (8 H, m).

Example 131

3-[[4-(dimethylamino)-1,4-diphenyl-cyclohexyl]-methyl-carbamoyl]-propionic acid (Polar Diastereomer)

Succinic acid anhydride (0.97 g, 9.27 mmol) was heated to 130° C. and melted. The title compound from Example 9 (1.00 g, 3.24 mmol) was then added and the mixture heated further at this temperature for 7 h. The batch was purified by flash chromatography with chloroform/methanol (9:1→4:1→1:1→1:2→methanol).

Yield: 1.08 g (81%)

$^1$H-NMR (DMSO-$d_6$): 1.55 (2 H, m); 1.81 (2 H, m); 1.94 (6 H, s); 2.37 (4 H, m); 2.62 (2 H, m); 2.76 (1 H, m); 2.94 (3 H, s); 7.14 (3 H, m); 7.17 (2 H, m); 7.26 (1 H, m); 7.38 (4 H, m).

Example 146

[4-[[4-(4-methoxy-phenoxy)-[1,3,5]triazin-2-yl]-methyl-amino]-1,4-diphenyl-cyclohexyl]-dimethyl-amine (Polar Diastereomer)

Step 1:

N-(4-chloro-[1,3,5]triazin-2-yl)-N,N',N'-trimethyl-1,4-diphenyl-cyclohexane-1,4-diamine A solution of the title compound from Example 9 (462 mg, 1.5 mmol), 2,4-dichloro-1,3,5-triazine (225 mg, 1.5 mmol) and diisopropyl ethylamine (248 µL, 1.5 mmol) in abs. THF (10 mL) was stirred overnight at RT. The solvent was then removed in a vacuum, the remaining residue dissolved in ethyl acetate, washed with saturated $NaHCO_3$ solution and saturated NaCl solution, dried over $Na_2SO_4$ and purified by flash chromatography with ethyl acetate/MeOH (9:1).

Yield: 166 mg (26%)

$^1$H-NMR (CDCl$_3$): 1.97 (4 H, m); 2.06 (6 H, s); 2.47 (4 H, bs); 3.01 (2 H, breit); 3.34 (3 H, s); 7.14-7.40 (10 H, m); 8.29 (1 H, s).

Step 2:

[4-[[4-(4-methoxy-phenoxy)-[1,3,5]triazin-2-yl]-methyl-amino]-1,4-diphenyl-cyclohexyl]-dimethyl-amine (Polar Diastereomer)

The title compound of step 1 (166 mg, 0.39 mmol), 4-methoxyphenol (56 mg, 0.45 mmol) and sodium hydride (18 mg, 0.45 mmol, 60% dispersion in mineral oil) were stirred in abs. dioxan (10 mL) for 4 h at RT. The solvent was then removed in a vacuum, the remaining residue dissolved in ethyl acetate, washed with saturated $NaHCO_3$ solution and saturated NaCl solution, dried over $Na_2SO_4$ and purified by flash chromatography with ethyl acetate/MeOH (4:1).

Yield: 126 mg (63%), porous solid $^1$H-NMR (CDCl$_3$): 1.84 (4 H, m); 2.03 (6 H, s); 2.60 (4 H, breit); 3.23 (3 H, s); 3.80 (3 H, s); 6.87-7.38 (14 H, m); 8.37 (1 H, s).

Example 149

[4-[(benzyl-methyl-amino)-methyl]-1,4-diphenyl-cyclohexyl]-dimethylamine

Step 1:

4-cyano-4-phenyl-heptane dicarboxylic acid-dimethyl ester

Phenyl acetonitrile (11.7 g, 100 mmol) and methylacrylate (47 mL, 500 mmol) were provided in tert-butyl alcohol (60 mL) and heated to boiling. The heat source was then removed. Triton B (benzyl trimethyl ammonium hydroxide, 40% in methanol, 15.2 mL) dissolved in tert-butyl alcohol (23 mL) was firstly added slowly in drops and then quickly. After the addition in drops, the batch was heated to boiling for 4 h. The reaction mixture was cooled to room temperature overnight. For work up the batch was mixed with toluol (100 mL) and water (70 mL), the organic phase separated and washed with water (70 mL) and saturated NaCl solution (50 mL). After drying with $Na_2SO_4$ the solvent was distilled. Purification occurred by bulb tube distillation at a temperature of approx. 235° C. The product could be isolated as a colourless, viscous substance.

Yield: 22.5 g (75%)

$^1$H-NMR (DMSO-$d_6$): 2.32 (8 H, m); 3.51 (6H; s); 7.40 (5 H, m).

$^{13}$C-NMR (DMSO-$d_6$): 22.47; 27.16; 39.28; 44.11; 113.82; 118.55; 120.83; 121.78; 129.10; 164.44.

Step 2:

5-cyano-2-oxo-5-phenyl-cyclohexane carboxylic acid methyl ester 4-cyano-4-phenyl heptane dicarboxylic acid dimethylester (19.8 g, 68 mmol) was dissolved in dry tetrahydrofuran (480 mL). Potassium tert-butylate (13.2 g, 120 mmol) was then added in portions. During this addition the reaction mixture changed colour to orange. The batch was then boiled for 5 h with reflux. A brown solution was formed during boiling. The reaction mixture was cooled to room temperature overnight. 2.5N acetic acid (230 mL) was slowly added in drops to the reaction mixture with ice cooling. The batch was then mixed with toluol (100 mL), the organic phase separated and washed with saturated NaHCO$_3$ solution (3×100 mL), H$_2$O (3×50 mL) and NaCl solution (1×100 mL). After drying with Na$_2$SO$_4$ the solvent was distilled off in a vacuum. A yellowish solid remained.

Yield: 16.1 g (92%)
Melting point: 75-77° C.
$^1$H-NMR (DMSO-d$_6$): 2.23-2.74 (6 H, m); 3.74 (3H; s); 7.35-7.60 (5 H, m); 12.08 (1 H, bs).
$^{13}$C-NMR (DMSO-d$_6$): 26.95; 30.18; 34.04; 51.90; 94.79; 121.90; 125.46; 128.05; 128.85; 138.92; 169.95; 171.09.

Step 3:

4-oxo-1-phenyl-cyclohexane carbonitrile 5-cyano-2-oxo-5-phenyl cyclohexane carboxylic acid methyl ester (16.1 g, 63 mmol) was dissolved in 10% sulphuric acid (218 mL) and conc. acetic acid (502 mL) and stirred for 21 h at 100° C. For work up the batch was carefully diluted with water (400 mL) with ice cooling, extracted with ethyl acetate (3×100 mL), the organic phase washed thoroughly with water (6×100 mL), saturated NaHCO$_3$ solution (10×100 mL) and saturated NaCl solution (1×100 mL). After drying with Na$_2$SO$_4$ the solvent was distilled off in a vacuum.

Yield: 8.91 g (72%)
Melting point: 106-107° C.
$^1$H-NMR (DMSO-d$_6$): 2.38-2.48 (6 H, m); 2.70 (2H; m); 7.36 (1 H, m); 7.44 (2 H, m); 7.62 (2 H, m).
$^{13}$C-NMR (DMSO-d$_6$): 35.31; 38.10; 42.33; 121.73; 125.65; 128.19; 129.02; 139.17; 208.79.

Step 4:

8-phenyl-1,4-dioxa-spiro[4.5]decane-8-carbonitrile

The title compound from step 3 (8.91 g, 44.73 mmol) was taken up in toluol (300 mL) and mixed with ethylene glycol (6 mL, 106.8 mmol). After adding p-toluol sulphonic acid (0.128 g, 0.745 mmol), the batch was heated to boiling in the water separator for 3.5 h. The course of the reaction was followed by DC. After the reaction batch cooled, the toluol solution was extracted with water (5×60 mL) and saturated NaCl solution (3×40 mL) and dried over Na$_2$SO$_4$. After removal of the solvent in a vacuum, the ketone acetal was obtained as yellow solid.

Yield: 11.6 g (100%)
Melting point: 108-110° C.
$^1$H-NMR (DMSO-d$_6$): 1.86 (4 H, m); 2.01-2.30 (4H; m); 3.92 (4 H, s); 7.38-7.53 (5 H, m).
$^{13}$C-NMR (DMSO-d$_6$): 32.10; 34.07; 42.49; 63.86: 106.11; 122.14; 125.51; 128.16; 129.02; 139.90.

Step 5:

8-phenyl-1,4-dioxa-spiro[4.5]decane-8-carboxylic acid

The title compound from step 4 (10.9 g, 46.9 mmol) was dissolved in ethylene glycol (92 mL), mixed with NaOH (4.00 g, 100 mmol) and then heated to boiling with reflux. No further nitrile could be detected after 20 h. For work up the batch was mixed with ice (approx. 250 g), coated with ether (90 mL) and acidified by slowly adding semiconcentrated HCl (118 mL). The aqueous phase was extracted with ether (3×70 mL), the combined organic extracts were washed with saturated NH$_4$Cl solution (2×70 mL), dried over Na$_2$SO$_4$ and concentrated to low volume in a vacuum. By recrystallising the remaining residue from toluol the desired carboxylic acid was obtained as crystalline solid.

Yield: 7.42 g (59%)
Melting point: 134-139° C.
$^1$H-NMR (DMSO-d$_6$): 1.64 (4 H, m); 1.91 (2H; m); 2.41 (2 H, m); 3.86 (4 H, s); 7.36 (5 H, m); 12.52 (1 H, bs).
$^{13}$C-NMR (DMSO-d$_6$): 31.51; 32.05; 49.19; 63.65: 107.23; 125.70; 126.94; 128.39; 142.82; 175.53.

Step 6:

8-phenyl-1,4-dioxa-spiro[4.5]decane-8-carboxylic acid-benzyl-methylamide

The title compound from step 5 (8.00 g, 30.48 mmol) was dissolved in dichloromethane (240 mL) and mixed with 1,3-diisopropyl carbodiimide (4.44 g, 5.44 mL, 35.52 mmol) and 1-hydroxy-1H-benzotriazole hydrate (5.44 g, 35.5 mmol) at 0° C. The reaction mixture was stirred for 5 min with ice cooling and then N-benzyl methylamine (3.87 g, 4.12 mL, 32.0 mmol) was added. The reaction mixture was stirred for 3 d at room temperature. For work up the batch was concentrated until dry in a vacuum. The residue was purified by flash chromatography with cyclohexane/ethyl acetate (1:1).

Yield: 7.31 g (66%)
$^1$H-NMR (DMSO-d$_6$): 1.61 (4 H, m); 1.68 (4 H, m); 2.35 (3 H, m); 3.85 (6 H, s); 7.28 (10 H, br, m).

Step 7:

Benzyl-methyl-(8-phenyl-1,4-dioxa-spiro[4.5]dec-8-ylmethyl)-amine

The title compound from step 6 (1.20 g, 3.28 mmol) was dissolved in abs. tetrahydrofuran (160 mL), LiAlH$_4$ (0.25 g, 6.59 mmol) added in argon and stirred for 5 h with reflux. The batch was then cooled to room temperature and stirred overnight. The batch was hydrolysed with THF (20 mL) and H$_2$O (20 mL) with ice cooling and subsequently stirred for 30 min. The batch was filtered via a fritted glass filter with diatomaceous earth, subsequently washed with THF and dichloromethane (50 mL) and concentrated to low volume in a vacuum. The residue was purified by means of flash chromatography and cyclohexane/ethyl acetate (1:1).

Yield: 0.50 g (43%)
$^1$H-NMR (DMSO-d$_6$): 1.35 (2 H, m); 1.38 (2 H, m); 1.72 (5 H, m); 2.20 (2 H, d); 2.48 (2 H, m); 3.22 (2 H, s); 3.84 (4 H, m); 7.25 (8 H, m), 7.44 (2H d).

Step 8:

4-[(benzyl-methyl-amino)-methyl]-4-phenylcyclohexanone

The title compound from step 7 (3.40 g, 9.67 mmol) was mixed with 5% sulphuric acid (300 mL) and stirred for 48 h at room temperature. For work up the reaction mixture was mixed with ether (100 mL), the phases separated and the aqueous phase extracted with ether (2×100 mL). The aqueous phase was then basified with 5N NaOH and extracted with dichloromethane (3×100 mL). The organic phase was dried over Na$_2$SO$_4$, filtered and concentrated until dry in a vacuum.

Yield: 2.74 g (92%)
$^1$H-NMR (DMSO-d$_6$): 1.79 (3 H, s); 2.07 (2 H, m); 2.16 (5 H, m); 2.22 (1 H, m); 3.26 (2 H, s); 7.22 (6 H, m); 7.37 (2 H, t), 7.55 (2 H, d).

Step 9:

4-[(benzyl-methyl-amino)-methyl]-1-methylamino-4-phenyl-cyclohexane carbonitrile 40% aqueous methylamine solution (5.40 mL, 42.7 mmol) and the title compound from step 8 (2.74 g, 8.91 mmol) dissolved in methanol (10 mL) were added to a solution of 4N hydrochloric acid (2.33 mL) and methanol (1.40 mL) cooled to 0° C. The reaction mixture was then mixed with potassium cyanide (1.40 g, 21.1 mmol) and stirred for 1 d at room temperature. For work up the mixture was mixed with water (30 mL) and extracted with ether (3×50 mL). The combined organic phases were dried with $Na_2SO_4$, filtered and concentrated to low volume in a vacuum.

Yield: 2.69 g (90%)

$^1$H-NMR (DMSO-$d_6$): 1.11 (2 H, m); 1.68 (1 H, m); 1.72 (2 H, m); 1.78 (1 H, m); 1.86 (2 H, s); 1.92 (2 H, m); 2.22 (2 H, d). 2.28 (1 H, m); 2.38 (2 H, m); 2.67 (1 H, m); 3.17 (1 H, m); 3.29 (2 H, m); 7.25 (10 H, m).

Step 10:

{4-[(benzyl-methyl-amino)-methyl]-1,4-diphenyl-cyclohexyl}-methylamine

Phenyl lithium (12.9 mL, 23.2 mmol, 1.8 M in dibutyl ether) was provided in argon, mixed in drops with the title compound from step 9 (2.69 g, 7.74 mmol) in THF (15 mL), and the reaction solution was stirred for 1 h with reflux. The reaction mixture was hydrolysed with saturated $NH_4Cl$ solution (27 mL) with ice bath cooling and the phases separated. The aqueous phase was extracted with ether (3×50 mL). The combined organic phases were dried over $Na_2SO_4$, filtered and concentrated until dry in a vacuum. The residue was separated by Chromatotron and dichloromethane→dichloromethane/methanol (9:1)→methanol. 1.20 g of ketone were isolated. The desired product was obtained as diastereomer mixture and as such was further converted.

Yield: 0.360 g (12%)

$^1$H-NMR (DMSO-$d_6$): 1.75 (1 H, m); 1.79 (3 H, s); 1.92 (1 H, m); 2.02 (3 H, m); 2.17 (6 H, m); 2.46 (1 H, m); 2.61 (2 H, m); 7.25 (13 H, m); 7.54 (2 H, m).

Step 11:

[4-[(benzyl-methyl-amino)-methyl]-1,4-diphenyl-cyclohexyl]-dimethylamine

A solution of the title compound from step 10 (diastereomer mixture) (0.350 g, 0.878 mmol) and formalin (1.23 mL, 37% aqueous solution) in acetonitrile (15 mL) was mixed in portions with sodium cyanoboron hydride (0.250 g, 3.86 mmol) and stirred for 45 min at room temperature. Conc. acetic acid was then added until a neutral reaction occurred and the mixture was subsequently stirred for 45 min at room temperature. For work up the solvent was removed in a vacuum, the residue taken up in 2N NaOH (40 mL) and then extracted with ether (3×40 mL). The organic solution was dried over $Na_2SO_4$, filtered and concentrated to low volume in a vacuum. The remaining residue was purified by Chromatotron and with cyclohexane/ethyl acetate 1:1. Separation of the diastereomers could not be achieved.

Yield: 70 mg (19%)

$^1$H-NMR (DMSO-$d_6$): 1.60 (4 H, m); 1.72 (3 H, s); 1.82 (6 H, s); 2.14 (2 H, m); 2.49 (4 H, s); 3.19 (2 H, s); 6.93 (2 H, m); 7.21 (5 H, m); 7.40 (8 H, m).

Example 153

[4-[[4-(benzylamino)-[1,3,5]triazin-2-yl]-methyl-amino]-1,4-diphenyl-cyclohexyl]-dimethylamine (Polar Diastereomer)

The title compound from Example 146, step 1 (100 mg, 0.236 mmol), benzylamine (55 μL, 0.5 mmol) and diisopropyl ethylamine (50 μL, 0.3 mmol) dissolved in abs. THF (2.0 mL) were stirred in a closed vessel for 5 h at 70° C. The solvent was then removed in a vacuum, the remaining residue dissolved in dichloromethane, washed with saturated $NaHCO_3$ solution, dried over $Na_2SO_4$ and purified by flash chromatography with ethyl acetate/MeOH (4:1→1:1). The product still contained benzylamine, which was removed in a vacuum at 90° C.

Yield: 83 mg (90%), oil $^1$H-NMR (CDCl$_3$): 1.77 (4 H, m); 2.02 (6 H, s); 2.37 (2 H, m); 2.97 (2 H, breit); 3.28 (3 H, s); 4.38 (2 H, s); 6.01 (1 H, s); 7.12-7.40 (15 H, m); 8.00 (1 H, s).

The following compounds were obtained following a specification such as described in Example 153 except that the amines listed in Table 1-10 were used.

TABLE 1-10

| Ex. No. | Amine | Product | Cy (%)/MS (m/z) |
|---|---|---|---|
| 154 | Cyclohexylamine | dimethyl-[4-[methyl-(4-piperidin-1-yl-[1,3,5]triazin-2-yl)-amino]-1,4-diphenyl-cyclohexyl]-amine (polar diastereomer) | 71 (471) |
| 155 | n-butylamine | [4-[(4-butylamino-[1,3,5]triazin-2-yl)-methyl-amino]-1,4-diphenyl-cyclohexyl]-dimethylamine (polar diastereomer) | 68 (459) |
| 156 | Aniline | [4-[(4-anilino-[1,3,5]triazin-2-yl)-methyl-amino]-1,4-diphenyl-cyclohexyl]-dimethyl-amine (polar diastereomer) | 59 (479) |
| 157 | Isopropyl methylamine | [4-[[4-(isopropyl-methyl-amino)-[1,3,5]triazin-2-yl]-methyl-amino]-1,4-diphenyl-cyclohexyl]-dimethylamine (polar diastereomer) | 75 (459) |
| 158 | t-butylamine | [4-[[4-(tert-butylamino)-[1,3,5]triazin-2-yl]-methyl-amino]-1,4-diphenyl-cyclohexyl]-dimethylamine (polar diastereomer) | 64 (459) |

Example 163

[4-[(butyl-methyl-amino)-methyl]-1,4-diphenyl-cyclohexyl]-dimethylamine (Non-polar Diastereomer)

Step 1:

8-phenyl-1,4-dioxa-spiro[4.5]decane-8-carboxylic acid-butyl-methylamide

The title compound from Example 149, step 5 (6.50 g, 24.8 mmol) was dissolved in dichloromethane (200 mL) and mixed with diisopropyl carbodiimide (3.60 g, 4.41 mL, 28.8 mmol) and 1-hydroxy-1H-benzotriazole hydrate (4.41 g, 28.8 mmol) at 0° C. The reaction mixture was stirred for 5 h with ice cooling and N-methyl butylamine (2.34 g, 3.08 mL, 26.0 mmol) was then added. The reaction mixture was stirred for 2 d at room temperature. For work up the batch was concentrated until dry in a vacuum. The residue was purified by flash chromatography with cyclohexane/ethyl acetate (2:1).

Yield: 3.50 g (45%)

$^1$H-NMR (DMSO-$d_6$): 0.95 (6 H, m); 1.39 (2 H, s); 1.80 (2 H, m); 1.85 (6 H, m); 2.24 (2 H, m); 2.51 (1 H, m); 3.10 (1 H, br m).); 3.84 (4 H, s); 7.23 (3 H, m); 7.34 (2 H, m).

Step 2:

Butyl-methyl-(8-phenyl-1,4-dioxa-spiro[4.5]dec-8-ylmethyl)-amine

The title compound from step 1 (3.50 g, 10.6 mmol) was dissolved in abs. tetrahydrofuran (400 mL), LiAlH$_4$ (0.66 g, 17.5 mmol) added in argon and stirred for 5 h with reflux. The batch was then cooled to room temperature and stirred overnight. The batch was hydrolysed with THF (20 mL) and H$_2$O (20 mL) with ice cooling and subsequently stirred for 30 min. The batch was filtered via a fritted glass filter with diatomaceous earth, rewashed with THF and dichloromethane (50 mL) and concentrated to low volume in a vacuum. The residue was purified by flash chromatography and cyclohexane/ethyl acetate (9:1→1:1).

Yield: 2.50 g (76%)

$^1$H-NMR (DMSO-$d_6$): 0.77 (3 H, t); 1.19 (6 H, m); 1.52 (2 H, m); 1.77 (2 H, m); 1.83 (3 H, s); 2.05 (2 H, m); 2.18 (2 H, m); 2.31 (2 H, s); 3.84 (4 H, br m); 7.19 (1 H, m); 7.33 (4 H, m).

Step 3:

4-[(butyl-methyl-amino)-methyl]-4-phenylcyclohexanone

The title compound from step 2 (2.50 g, 7.8 mmol) was mixed with 5% sulphuric acid (300 mL) and stirred for 48 h at room temperature. For work up the reaction mixture was mixed with ether (100 mL), the phases separated and the aqueous phase extracted with ether (2×100 mL). The aqueous phase was basified with 5N NaOH and extracted with dichloromethane (3×10 mL). The organic phase was dried over Na$_2$SO$_4$, filtered and concentrated until dry in a vacuum.

Yield: 1.53 g (73%)

$^1$H-NMR (DMSO-$d_6$): 0.78 (3 H, t); 1.15 (4 H, br, m); 1.87 (3 H, s); 1.93 (2 H, m); 2.13 (6 H, br m); 2.45 (4 H, m); 7.25 (1 H, t); 7.37 (2 H, t); 7.49 (2 H, d).

Step 4:

4-[(butyl-methyl-amino)-methyl]-1-methylamino-4-phenyl-cyclohexane carbonitrile 40% aqueous methylamine solution (3.42 mL, 27 mmol) and the title compound from step 3 (1.54 g, 5.60 mmol) dissolved in methanol (5 mL) were added to a solution of 4N hydrochloric acid (1.50 mL) and methanol (0.89 mL) cooled to 0° C. The reaction mixture was then mixed with potassium cyanide (0.901 g, 13.4 mmol) and stirred for 3 d at room temperature. For work up the mixture was mixed with water (50 mL) and extracted with ether (3×100 mL). The combined organic phases were dried over Na$_2$SO$_4$, filtered and concentrated to low volume in a vacuum.

Yield: 1.76 g (100%)

$^1$H-NMR (DMSO-$d_6$): 0.77 (3 H, m); 1.07 (5 H, m); 1.68 (3 H, m); 1.77 (1 H, s); 1.84 (1 H, m); 1.92 (2 H, m); 2.03 (1 H, m); 2.12 (2 H, m); 2.21 (2 H, m); 2.31 (3 H, m); 2.43 (1 H, m); 2.63 (1 H, m); 7.19 (1 H, m); 7.37 (4 H, m).

Step 5:

{4-[(butyl-methyl-amino)-methyl]-1,4-diphenyl-cyclohexyl}-methylamine

Phenyl lithium (9.33 mL, 16.8 mmol, 1.8 M in dibutyl ether) was provided in argon, mixed in drops with the title compound from step 4 (1.76 g, 5.61 mmol) in ether (15 mL) and the reaction solution stirred for 1 h at 50° C. The reaction mixture was hydrolysed with saturated NH$_4$Cl solution (100 mL) with ice bath cooling and the phases separated. The aqueous phase was extracted with ether (3×50 mL). The combined organic phases were dried over Na$_2$SO$_4$, filtered and concentrated until dry in a vacuum. The residue was separated by Chromatotron and dichloromethane.

Yield: 0.400 g (20%), non-polar diastereomer $^1$H-NMR (DMSO-$d_6$): 0.71 (3 H, t); 1.05 (5 H, m); 1.59 (3 H, m); 1.76 (6 H, s); 2.01 (6 H, m); 2.40 (2 H, br s); 7.19 (2 H, m); 7.34 (6 H, m); 7.47 (2 H, d).

Yield: 0.170 g (9%), polar diastereomer $^1$H-NMR (DMSO-$d_6$): 0.76 (3 H, t); 1.13 (4 H, m); 1.37 (2 H, m); 1.75 (4 H, s); 1.86 (3 H, m); 2.06 (6 H, m); 2.41 (2 H, s); 3.17 (1 H, s); 7.13 (2 H, m); 7.26 (6 H, m); 7.38 (2 H, m).

Step 6:

[4-[(butyl-methyl-amino)-methyl]-1,4-diphenyl-cyclohexyl]-dimethylamine (Non-polar Diastereomer)

A solution of the title compound from step 6 (non-polar diastereomer) (0.400 g, 1.1 mmol) and formalin (1.54 mL, 37% aqueous solution) in acetonitrile (20 mL) was mixed in portions with sodium cyanoboron hydride (0.313 g, 4.84 mmol) and stirred for 45 min at room temperature. Conc. acetic acid was then added until a neutral reaction occurred and the mixture subsequently stirred for 45 min at room temperature. For work up the solvent was removed in a vacuum, the residue taken up in 2N NaOH (40 mL) and then extracted with ether (3×40 mL). The organic phase was dried over Na$_2$SO$_4$, filtered and concentrated to a low volume in a vacuum. The residue was purified by Chromatotron and dichloromethane→methanol.

Yield: 220 mg (53%)

¹H-NMR (DMSO-d₆): 0.70 (3 H, t); 0.99 (4 H, m); 1.42 (2 H, m); 1.58 (2 H, m); 1.75 (3 H, s); 1.86 (6 H, s); 1.95 (2 H, m); 2.16 (4 H, m); 2.32 (2 H, m); 7.18 (1 H, m); 7.38 (9 H, m).

Example 164

[4-[(butyl-methyl-amino)-methyl]-1,4-diphenyl-cyclohexyl]-dimethylamine (Polar Diastereomer)

A solution of the title compound from Example 163, step 6 (polar diastereomer) (0.170 g, 0.47 mmol) and formalin (0.66 mL, 37% aqueous solution) in acetonitrile (8.2 mL) was mixed in portions with sodium cyanoboron hydride (0.134 g, 2.07 mmol) and stirred for 45 min at room temperature. Conc. acetic acid was then added until a neutral reaction occurred and the mixture stirred for 45 min at room temperature. For work up the solvent was removed in a vacuum, the residue taken up in 2N NaOH (40 mL) and then extracted with ether (3×40 mL). The organic phase was dried over Na₂SO₄, filtered and concentrated to a low volume in a vacuum. The residue was purified by Chromatotron and dichloromethane→methanol.

Yield: 75 mg (41%)

¹H-NMR (DMSO-d₆): 0.77 (3 H, t); 1.18 (5 H, m); 1.51 (2 H, m); 1.76 (5 H, m); 1.94 (6 H, s); 2.04 (3 H, m); 2.27 (2 H, m); 2.40 (2 H, s); 7.23 (10 H, m).

Nephelometric Solubility Study (Phosphate Buffer pH 7.4):

This method examines the solubility of a substance with fixed concentrations (1 µM, 3 µM, 10 µM, 30 µM and 100 µM) in 10 mM of phosphate buffer solution with pH 7.4. A 10 mM solution of the substances in DMSO will be initially required, from which 100-fold stock solutions of the above-mentioned concentration level again in DMSO are produced, the final DMSO concentration in the test batch amounting to 1% (v/v). The experiment is conducted multiple times for determination. After the DMSO stock solutions have been added to the buffer, the batch is incubated for 2 h at 37° C. before an absorption determination at 620 nm occurs. If the absorption of the samples increases above that of the pure buffer/DMSO solution, then this applies as indicator for a precipitate formation. The lower solubility limit ("lower boundary") is the concentration preceding that with the first precipitate formation (e.g. 3 µM if precipitation formation was detected at 10 µM).

Studies on the Efficacy of the Compounds According to the Invention

Measurement of the ORL 1-bond

The compounds were examined with membranes of recombinant CHO-ORL 1 cells in a receptor binding assay with ³H-nociceptin/orphanin FQ. This test system was conducted in accordance with the method outlined by Ardati et al. (Mol. Pharmacol., 51, 1997, pp. 816-824). The concentration of ³H-nociceptin/orphanin FQ amounted to 0.5 nM in these tests. The binding assays were conducted in each case on 20 µg of membrane protein per 200 µl of preparation in 50 mM of HEPES, pH 7.4, 10 nM of MgCl₂ and 1 mM of EDTA. The binding to the ORL 1-receptor was determined using 1 mg of WGA-SPA beads (Amersham-Pharmacia, Freiburg) in each case by incubating the preparation for one hour at RT and then conducting measurements in the Trilux scintillation counter (Wallac, Finland). The affinity is indicated as nanomolar K, value or in % inhibition at c=1 µM in Table 1.

Measurement of the µ-bond

The affinity to the human µ-opiate receptor was determined in a homogeneous preparation in microtiter plates. For this, dilution series of the respective compound to be tested were incubated for 90 minutes at room temperature with a receptor membrane preparation (15-40 mg of protein per 250 µl of incubation batch) of CHO-K1 cells, which express the human µ-opiate receptor (RB-HOM receptor membrane preparation of NEN, Zaventem, Belgium), in the presence of 1 nmol/l of the radioactive ligand [³H']-naloxone (NET719, NEN, Zaventem, Belgium) and of 1 mg WGA-SPA beads (wheat germ agglutinin SPA beads from Amersham/Pharmacia, Freiburg, Germany) in a total volume of 250 µl. 50 mmol/l of tris-HCl supplemented by 0.05% by wt. of sodium azide and 0.06% by wt. of bovine serum albumin was used as incubation buffer. 25 µmol/l of naloxone were additionally added to determine the non-specific bond. After the ninety-minute incubation time had ended, the microtiter plates were centrifuged for 20 minutes at 1000 g and the radioactivity measured in a β-counter (Microbeta-Trilux, PerkinElmer Wallac, Freiburg, Germany). The percentage displacement of the radioactive ligand from its binding to the human µ-opiate receptor was determined with a concentration of the test substances of 1 µmol/l and was specified as percentage inhibition (% inhibition) of the specific bond. In some instances, working from the percentage displacement by different concentrations of the compounds of the general formula I according to the invention, $IC_{50}$ inhibition concentrations were calculated that effect a 50 percent displacement of the radioactive ligand. Ki values for the test substances were obtained by conversion using the Cheng-Prusoff equation. In some cases, the determination of the Ki value was omitted and only the inhibition with a test concentration of 1 µM was determined.

Measurement of the Kappa-bond

The determination occurred in a homogeneous batch in microtiter plates. For this, dilution series of the respective substances to be tested were incubated for 90 minutes at room temperature with a receptor membrane preparation (7 mg of protein per 250 µl of incubation batch) of CHO-K1 cells, which express the human κ-opiate receptor, in the presence of 1 nmol/l of the radioactive ligand [³H']-CL-977 and 1 mg WGA-SPA beads (wheat germ agglutinin SPA beads from Amersham/Pharmacia, Freiburg, Germany) in a total volume of 250 µl, 50 mmol/l of tris-HCl supplemented by 0.05% by wt. of sodium azide and 0.06% by wt. of bovine serum albumin was used as incubation buffer. 100 µmol/l of naloxone were additionally added to determine the non-specific bond. After the ninety-minute incubation time had ended, the microtiter plates were centrifuged for 20 minutes at 500 rpm and the radioactivity measured in a β-counter (Microbeta-Trilux 1450, PerkinElmer Wallac, Freiburg, Germany). The percentage displacement of the radioactive ligand from its binding to the human κ-opiate receptor was determined with a concentration of the test substances of 1 µmol/l and was specified as percentage inhibition (% inhibition) of the specific bond. Working from the percentage displacement by different concentrations of the compounds to be tested, $IC_{50}$ inhibition concentrations can be calculated that effect a 50 percent displacement of the radioactive ligand. Ki values for the test substances can be calculated by conversion using the Cheng-Prusoff equation.

The results are collated in the following table:

| Ex. | % Inhibition (ORL1) [1 µM] | Ki (ORL1) Mean [µM] | % Inhibition (µ) [1 µM] | Ki (µ) Mean [µM] |
|---|---|---|---|---|
| 1 | 26 | n.d. | 46 | n.d. |
| 2 | 9 | n.d. | 22 | n.d. |

| Ex. | % Inhibition (ORL1) [1 µM] | Ki (ORL1) Mean [µM] | % Inhibition (µ) [1 µM] | Ki (µ) Mean [µM] |
|---|---|---|---|---|
| 3 | 81 | n.d. | 0 | n.d. |
| 4 | 33 | 0.94 | 38 | n.d. |
| 5 | 37 | 0.635 | 82 | 0.0705 |
| 6 | 51 | 0.18 | 83 | 0.049 |
| 7 | 34 | 0.99 | 48. | 1.16 |
| 8 | 14 | n.d. | 30 | n.d. |
| 9 | 80 | 0.01775 | 49 | 0.64 |
| 10 | 18 | n.d. | 34 | n.d. |
| 11 | 87 | 0.006 | 59 | 0.6 |
| 12 | 53 | 0.365 | 86 | 0.0805 |
| 13 | 36 | 1.31 | 66 | 0.155 |
| 14 | 17 | n.d. | 67 | n.d. |
| 15 | 83 | n.d. | 98 | n.d. |
| 16 | 18 | n.d. | 65 | n.d. |
| 17 | 17 | 1.17 | 61 | 0.14 |
| 18 | 95 | 0.0027 | 100 | 0.00125 |
| 19 | 94 | 0.017 | 96 | 0.0475 |
| 20 | 92 | 0.011 | 101 | 0.0011 |
| 21 | 43 | 0.49 | 57 | 0.78333 |
| 22 | 43 | n.d. | 92 | n.d. |
| 23 | 13 | n.d. | 15 | n.d. |
| 24 | 82 | 0.063 | 97 | 0.01425 |
| 25 | 60 | 0.19 | 91 | 0.0154 |
| 26 | 76 | n.d. | 69 | n.d. |
| 27 | 95 | 0.0049 | 98 | 0.00805 |
| 28 | 30 | 1.01 | 36 | 0.895 |
| 29 | 70 | 0.09 | 98 | 0.0015 |
| 30 | 93 | 0.0016 | 99.5 | 0.0022 |
| 31 | 60 | 0.0955 | 90 | 0.022 |
| 32 | 65 | 0.051 | 81 | 0.052 |
| 33 | 9 | 3.955 | 42 | 1.11 |
| 34 | 27 | 1.89 | 81 | 0.215 |
| 35 | 29 | 0.99333 | n.d. | 0.41 |
| 36 | 30 | n.d. | n.d. | n.d. |
| 37 | 66 | 0.1025 | n.d. | 2.455 |
| 38 | 35 | n.d. | 29 | n.d. |
| 39 | 73 | 0.0535 | 93 | 0.555 |
| 40 | 84 | 0.0255 | 46 | 0.445 |
| 41 | 19 | n.d. | 42 | 4.11 |
| 42 | 28 | 1.395 | 101 | 0.0018 |
| 43 | 35 | 0.755 | 58 | 0.1305 |
| 44 | 68 | 0.0775 | 96 | 0.01335 |
| 45 | 72 | 0.0485 | 99 | 0.00124 |
| 46 | 49 | 0.72 | 84 | 0.188 |
| 47 | 39 | 1.605 | 65 | 0.755 |
| 48 | 22 | 1.25 | 48 | 0.9 |
| 49 | 97 | 0.00155 | 93 | 0.0615 |
| 50 | 58 | 0.1045 | 69 | 0.12 |
| 51 | 91 | 0.00128 | 90 | 0.044 |
| 52 | 87 | 0.01 | 93 | 0.018 |
| 53 | 61 | n.d. | 18 | n.d. |
| 54 | 36 | n.d. | 61 | n.d. |
| 56 | 22 | n.d. | 56 | n.d. |
| 57 | 43 | n.d. | 80 | n.d. |
| 58 | 52 | 0.425 | 71 | 0.115 |
| 59 | 69 | 0.175 | 80 | 0.034 |
| 60 | 47 | 0.53 | 77 | 0.107 |
| 61 | 56 | 0.375 | 84 | 0.032 |
| 62 | 49 | 0.0895 | 85 | 0.0475 |
| 63 | 60 | 0.087 | 91 | 0.0066 |
| 64 | 83 | 0.0345 | 96 | 0.0053 |
| 65 | 49 | 0.435 | 74 | 0.0925 |
| 66 | 35 | 4.01 | 18 | 10.23 |
| 67 | 31 | n.d. | 38 | 5.205 |
| 68 | 15 | n.d. | 43 | n.d. |
| 69 | 50 | 0.20667 | 40 | 0.65 |
| 70 | 28 | n.d. | 77 | n.d. |
| 71 | 38 | 0.36 | 55 | 1.19 |
| 72 | 58 | 0.115 | 40 | 1.695 |
| 73 | 45 | 0.165 | 84 | 0.027 |
| 74 | 67 | 0.057 | 52 | 0.66 |
| 75 | 24 | 2.955 | 34 | 0.67 |
| 76 | 55 | 0.295 | 83 | 0.18 |
| 77 | 98 | 0.00071 | 100 | 0.0004 |
| 78 | 39 | 0.73 | 67 | 0.385 |
| 79 | 96 | n.d. | 95 | n.d. |
| 80 | 91 | n.d. | 99 | n.d. |
| 81 | 82 | n.d. | 91 | n.d. |
| 82 | 53 | n.d. | 78 | n.d. |
| 83 | 47 | n.d. | 82 | n.d. |
| 84 | 72 | n.d. | 97 | n.d. |
| 85 | 99 | 0.00081 | n.d. | 0.115 |
| 86 | 35 | n.d. | n.d. | n.d. |
| 87 | 53 | n.d. | n.d. | n.d. |
| 88 | 54 | n.d. | n.d. | n.d. |
| 89 | 24 | 1.075 | n.d. | 0.325 |
| 90 | 44 | 0.525 | n.d. | 1.055 |
| 91 | 98 | 0.00535 | n.d. | 0.74 |
| 92 | 97 | 0.015 | n.d. | 0.00635 |
| 93 | 84 | 0.235 | n.d. | 0.045 |
| 94 | 68 | n.d. | 83 | n.d. |
| 95 | 32 | n.d. | 49 | n.d. |
| 96 | 64 | 0.108 | 62 | 0.235 |
| 97 | 18 | n.d. | 32 | n.d. |
| 98 | 91 | n.d. | 101 | n.d. |
| 99 | 97.5 | 0.00054 | 100 | 0.0012 |
| 100 | 85 | 0.21 | 97 | 2.4 |
| 101 | 93 | 0.00245 | 79 | 0.063 |
| 102 | 18 | n.d. | 37 | 3.73 |
| 103 | 25 | n.d. | 64 | n.d. |
| 104 | 67 | 0.033 | 93 | 0.01 |
| 105 | 93 | 0.00065 | 101 | 0.0012 |
| 106 | 87 | 0.02 | 98 | 0.435 |
| 107 | 19 | 1.485 | 38 | 1.995 |
| 108 | 53 | n.d. | 89 | n.d. |
| 109 | 60 | n.d. | 43 | n.d. |
| 110 | 38 | 0.62 | 78 | 0.155 |
| 111 | 27 | 1.055 | 60 | 0.42 |
| 112 | 47 | n.d. | n.d. | n.d. |
| 113 | 48 | n.d. | n.d. | n.d. |
| 114 | 91 | 0.01385 | n.d. | 0.13 |
| 115 | 24 | 1.165 | n.d. | 1.66667 |
| 116 | 85 | 0.021 | n.d. | 0.014 |
| 117 | 76 | 0.00013 | n.d. | 0.00035 |
| 118 | 52 | n.d. | n.d. | n.d. |
| 119 | 89 | 0.00143 | n.d. | 0.039 |
| 120 | 36 | 0.465 | n.d. | 2.9 |
| 121 | 70 | 0.23 | n.d. | 1.425 |
| 122 | 83 | 0.0074 | n.d. | 0.17667 |
| 123 | 65 | n.d. | n.d. | 2.595 |
| 124 | 23 | n.d. | n.d. | 0.735 |
| 125 | 35 | 2.05 | n.d. | 0.255 |
| 126 | 23 | n.d. | n.d. | n.d. |
| 127 | 18 | n.d. | 28 | n.d. |
| 128 | 15 | 0.93 | 46 | 0.255 |
| 129 | 67 | n.d. | 33 | n.d. |
| 130 | 88 | 0.018 | 62 | 0.415 |
| 131 | 37 | n.d. | 22 | 9.02 |
| 132 | 52 | 0.19 | 21 | 1.58 |
| 133 | 34 | n.d. | 37 | | n.d.—not determined.

Examination of the Pharmacological Properties of the Exemplary Compounds

Chung Model: Mononeuropathic Pain after Spinal Nerve Ligature

Animals: Male Sprague Dawley rats (140-160 g) from a commercial breeder (Janvier, Genest St. Isle, France) were held under a 12:12 h light-dark rhythm. The animals were kept with a free choice of feed and tap water. A break of one week was adhered to between delivery of the animals and the operation. The animals were tested multiple times after operation over a period of 4-5 weeks, in which case a wash out time of at least one week was adhered to.

Model description: Under pentobarbital narcosis (Narcoren®, 60 mg/kg i.p., Merial GmbH, Hallbergmoos, Germany), the left L5, L6 spinal nerves were exposed by removing a piece of paravertebral muscle and a portion of the left spinal process of the L5 lumbar vertebral body. The spinal nerves L5 and L6 were carefully isolated and bound with a firm ligature (NC silk black, USP 5/0, metric 1, Braun Melsungen AG, Melsungen, Germany) (Kim and Chung 1992). After ligature the muscle and adjacent tissue were sutured and the wound closed by metal clamps.

After a one-week recovery time the animals are placed in cages with a wire base for measurement of the mechanical allodynia. The pull-away threshold was determined at the ipsi- and/or contralateral rear paw by means of an electronic von Frey filament (Somedic AB, Malmö, Sweden). The median of five stimulations gave a data point. The animals were tested 30 min before application and at various times after application of test substance or vehicle solution. The data were determined as % maximum possible effect (% MPE) from the pre-testing of individual animals (=0% MPE) and the test values of an independent sham control group (=100% MPE). Alternatively the pull-away thresholds were shown in gram.

Statistical evaluation: $ED_{50}$ values and 95% confidence intervals were determined by means of semi-logarithmic regression analysis at the time of maximum effect. The data were analysed by means of a variance analysis with repeated measurements as well as a Bonferroni post hoc analysis procedure. The group size usually amounted to n=10.

References: Kim, S. H. and Chung, J. M.: An experimental model for peripheral neuropathy produced by segmental spinal nerve ligature in the rat, Pain, 50 (1992) 355-363.

The results are collated in the following table (Chung model):

| Ex. No. | MPE (%), (Dose in μg/kg, rat, i.v.) |
|---|---|
| 11 | 25 (100) |
| 51 | 29 (100) |
| 30 | 16 (100) |

The compounds according to the invention of type E where W=—NHMe or —NMe$_2$ (Ex. 9, 11 and 13) were compared with corresponding compounds of type E where W=—OH (C-1 and C-2):

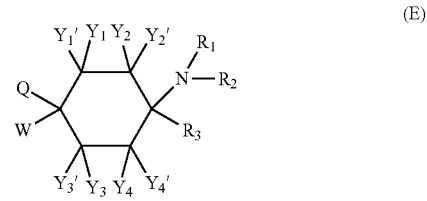

(E)

| Ex. | W | Q | R$_3$ | Ki (μ)/ Ki (ORL1) | Ki (kappa)/ Ki (ORL1) | Ki (ORL1) Mean [μM] | Ki (μ) Mean [μM] | Ki (kappa) Mean [μM] |
|---|---|---|---|---|---|---|---|---|
| 9 | HN— (NHMe) | phenyl | phenyl | 36 | 65 | 0.018 | 0.640 | 1.170 |
| 11 | —N(Me)— (NMe$_2$) | phenyl | phenyl | 100 | 193 | 0.006 | 0.600 | 1.160 |
| C-1 | HO— | phenyl | phenyl | 0.7 | 0.8 | 2.92 | 1.89 | 2.24 |
| 13 | —N(Me)— (NMe$_2$) | benzyl | phenyl | 0.1 | 2.9 | 1.310 | 0.155 | 3.745 |
| C-2 | HO— | benzyl | 4-methylphenyl | 0.003 | 1.46 | 1.000 | 0.003 | 1.460 |

As the above comparison data show, the compounds according to the invention (W=—NHMe or —NMe$_2$) have a higher selectivity with respect to the kappa-opioid receptor (defined as $1/[K_{i(ORL1)}/K_{i(kappa)}]$) compared to the structurally similar substances (W=OH). Moreover, with a favourable ORL 1/μ affinity ratio, the substances according to the invention also have a higher selectivity with respect to the μ-opioid receptor (defined as $1/[K_{i(ORL1)}/K_{i(\mu)}]$).

The compounds according to the invention of type 1 where n=0, X=—NMe and Q=phenyl (Ex. 27, 30, 31, 32, 49, 85 and 92) were compared to compounds of type F (C-3 to C-5) where Z=NMe or NCOR, R$_5$, R$_6$=H, W=NH, A$_{1-4}$=CH and R$_1$ to R$_3$, Y$_1$ to Y$_4$ and Y$_1$' to Y$_4$' corresponding to (1)

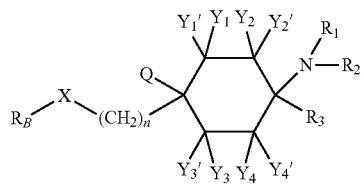
(1)

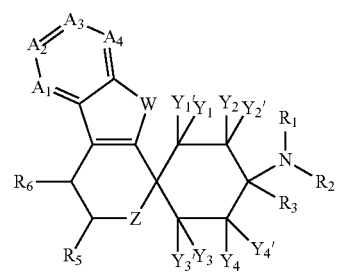
(F)

| Ex. | R$_B$ | Z | Diastereomer | Nephelometry (lower boundary) μM |
|---|---|---|---|---|
| 1 | Me | NA | polar | 100 |
| 49 | ↯ (butyl) | not applicable | polar | 100 |
| 85 | ↯ (pyridinylmethyl) | not applicable | polar | 100 |
| C-3: | not applicable | NMe | polar | 3 |
| 92 | ↯ (N-methylpyrazolyl-C(O)-) | not applicable | polar | 100 |
| 27 | ↯ (cinnamoyl) | not applicable | polar | 100 |
| c-4: | not applicable | ↯ (cinnamoyl) | polar | 12 |
| 30 | ↯ (PhCH$_2$NHC(O)-) | not applicable | polar | 100 |
| C-5: | not applicable | ↯ (PhCH$_2$NHC(O)-) | nonpolar | 12 |
| 31 | ↯ (EtNHC(O)-) | not applicable | nonpolar | 100 |
| 32 | ↯ (EtNHC(O)-) | not applicable | polar | 100 |

As the above comparison shows, the compounds according to the invention from Examples 27, 30, 31, 32, 49, 85 and 92 have a better solubility in aqueous media compared to structurally similar compounds (C-3 to C-5), which in particular should be associated with advantages with respect to the resorption properties and/or bioavailability.

The invention claimed is:

1. A compound of the formula (1):

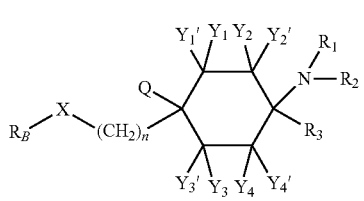
(1)

wherein $Y_1$, $Y_1'$, $Y_2$, $Y_2'$, $Y_3$, $Y_3'$, $Y_4$ and $Y_4'$ are each —H;

Q stands for -aryl or -heteroaryl;

$R_1$ and $R_2$, independently of one another, stand for —H or —CH$_3$; on condition that $R_1$ and $R_2$ do not both simultaneously stand for —H;

$R_3$ stands for —C$_{3-12}$-cycloaliphatic, -aryl, —C$_{1-8}$-aliphatic-C$_{3-12}$-cycloaliphatic, or —C$_{1-8}$-aliphatic-aryl;

n stands for 0;

X stands for —NR$_A$—;

$R_A$ stands for —H or —C$_{1-8}$-aliphatic;

$R_B$ stands for —C(=O)—C$_{1-8}$aliphatic-aryl or —C(=O)—C$_{1-8}$aliphatic-heteroaryl;

wherein

"aliphatic" respectively is a branched or unbranched, saturated or a mono- or polyunsaturated, unsubstituted or mono- or polysubstituted, aliphatic hydrocarbon residue;

"cycloaliphatic" respectively is a saturated or a mono- or polyunsaturated, unsubstituted or mono- or polysubstituted, alicyclic, mono- or multicyclic hydrocarbon residue;

wherein with respect to "aliphatic" and "cycloaliphatic", "mono- or polysubstituted" means the mono- or polysubstitution of one or more hydrogen atoms by substituents selected independently of one another from the group consisting of —F, —Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)—NHR$_0$, —NH—C(=O)N(R$_0$)$_2$, —Si(R$_0$)$_3$ and —PO(OR$_0$)$_2$;

"aryl", respectively independently, stands for a carbocyclic ring system with at least one aromatic ring, but without heteroatoms in this ring, wherein, optionally, the aryl residues can be condensed with further saturated, (partially) unsaturated or aromatic ring systems, and each aryl residue can be present in unsubstituted or mono- or polysubstituted form, wherein the aryl substituents can be the same or different and in any desired and possible position of the aryl;

"heteroaryl" stands for a 5-, 6- or 7-membered cyclic aromatic residue, which contains 1, 2, 3, 4 or 5 heteroatoms, wherein the heteroatoms, the same or different, are nitrogen, oxygen or sulphur, and the heterocycle can be unsubstituted or mono- or polysubstituted; wherein in the case of the substitution on the heterocycle the substituents can be the same or different and can be in any desired and possible position of the heteroaryl; and wherein the heterocycle can also be part of a bi- or polycyclic system;

wherein with respect to "aryl" and "heteroaryl", "mono- or polysubstituted" means the mono- or polysubstitution of one or more hydrogen atoms of the ring system by substituents selected from the group consisting of —F, —Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)—N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)R$_2$, —SH, —SR$_0$, —SO$_3$H, —S(=O)$_{1-2}$—R$_0$, —S(=O)$_{1-2}$NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NH—C(=O)NH$_2$, —NHC(=O)NHR$_0$, —NHC(=O)N(R$_0$)$_2$, —Si(R$_0$)$_3$ or —PO(OR$_0$)$_2$; wherein any N-ring atoms present can be respectively oxidised; and wherein $R_0$ respectively independently stands for —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl, —C$_{1-8}$-aliphatic -heteroaryl, -C$_{3-8}$-cycloaliphatic-C$_{1-8}$-aliphatic, —C$_{3-8}$-cycloaliphatic-aryl or —C$_{3-8}$-cycloaliphatic-heteroaryl;

said compound being in the form of a single stereoisomer or mixture thereof, the free compound and/or a physiologically compatible salt thereof.

2. Compound according to claim 1, which has the formula (2.2):

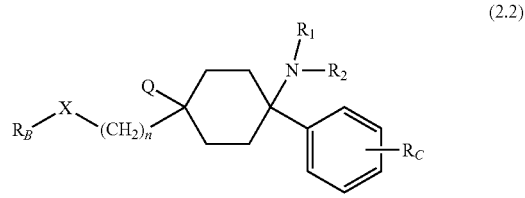

(2.2)

wherein $R_C$ stands for —H, —F, —Cl, —Br, —I, —CN, —NO$_2$, —CF$_3$, —OH or —OCH$_3$.

3. Compound according to claim 1, wherein $R_1$ stands for —CH$_3$; and $R_2$ stands for —H or —CH$_3$.

4. Compound according to claim 3, wherein

Q stands for -phenyl, or -indolyl;

$R_1$ stands for —CH$_3$;

$R_2$ stands for —H or —CH$_3$;

$R_A$ stands for —H or —C$_{1-8}$-alkyl; and $R_B$ stands for —C(=O)—C$_{1-8}$-alkyl-aryl or —C(=O)—C$_{1-8}$-alkyl-heteroaryl;

wherein aliphatic, aryl and heteroaryl are respectively unsubstituted or mono- or polysubstituted.

5. A pharmaceutical composition comprising at least one compound according to claim 1, said compound being in the form of a single stereoisomer or mixture thereof, the free compound and/or a physiologically compatible salt thereof, and optionally suitable additives and/or adjuvants and/or further active substances.

6. A method of treating pain in a patient in need of such treatment, said method comprising administering to said patient an effective amount therefor of a compound according to claim 1, said compound being in the form of a single stereoisomer or mixture thereof, the free compound and/or a physiologically compatible salt thereof.

7. A method of treating a condition in a patient in need of such treatment, said method comprising administering to said patient an effective amount therefor of a compound according to claim 1, said compound being in the form of a single stereoisomer or mixture thereof, the free compound and/or a physiologically compatible salt and/or solvate thereof, wherein said condition is selected from the group consisting of anxiety conditions, stress and stress-related syndromes, depressive illnesses, epilepsy, Alzheimer's disease, senile dementia, general cognitive dysfunctions, learning and memory disabilities (as nootropic), withdrawal symptoms, alcohol and/or drug and/or medication misuse and/or dependence, sexual dysfunctions, cardiovascular diseases, hypotension, hypertension, tinitus, pruritus, migraine, hearing impairment, deficient intestinal motility, eating disorders, anorexia, bulimia, mobility disorders, diarrhoea, cachexia, urinary incontinence, or as muscle relaxant, anticonvulsive or anaesthetic, or wherein said administering is for coadministration in the treatment with an opioid analgesic or with an anaesthetic, for diuresis or anti-natriuresis, anxiolysis, for modulating movement activity, for modulating neurotransmitter release and for treating neuro-degenerative diseases associated therewith, for treating withdrawal symptoms and/or for reducing the addiction potential of opioids.

8. Compound according to claim 1, which is selected from the group consisting of:

- N-(4-(dimethylamino)-1-(3-methyl-1H-indol-2-yl)-4-phenylcyclohexyl)-N-methyl-cinnamamide;
- (E)-N-(4-dimethylamino-1,4-diphenyl-cyclohexyl)-N-methyl-3-phenyl-acrylamide (non-polar diastereomer);
- (E)-N-(4-dimethylamino-1,4-diphenyl-cyclohexyl)-N-methyl-3-phenyl-acrylamide (polar diastereomer);
- N-[4-(dimethylamino)-1,4-diphenyl-cyclohexyl]-N-methyl-2,2-diphenyl-acetamide (polar diastereomer);
- (E)-N-[4-(cyclopentyl-methyl)-4-dimethylamino-1-phenyl-cyclohexyl]-N-methyl-3-phenyl-acrylamide (non-polar diastereomer);
- (E)-N-[4-(cyclopentyl-methyl)-4-dimethylamino-1-phenyl-cyclohexyl]-N-methyl-3-phenyl-acrylamide (polar diastereomer); and
- (E)-N-[4-dimethylamino-1-(3-methyl-1H-indol-2-yl)-4-phenyl-cyclohexyl]-N-methyl-3-phenyl-acrylamide (polar diastereomer);

and physiologically compatible salts thereof.

* * * * *